US008865907B2

(12) United States Patent
Sumino et al.

(10) Patent No.: US 8,865,907 B2
(45) Date of Patent: Oct. 21, 2014

(54) METHOD OF PRODUCING PYRONE AND PYRIDONE DERIVATIVES

(75) Inventors: Yukihito Sumino, Osaka (JP); Kazuya Okamoto, Osaka (JP); Moriyasu Masui, Osaka (JP); Toshiyuki Akiyama, Osaka (JP)

(73) Assignee: Shionogi & Co., Ltd., Osaka-Shi, Osaka (JP)

( * ) Notice: Subject to any disclaimer, the term of this patent is extended or adjusted under 35 U.S.C. 154(b) by 0 days.

(21) Appl. No.: 13/260,063

(22) PCT Filed: Mar. 26, 2010

(86) PCT No.: PCT/JP2010/055316
§ 371 (c)(1),
(2), (4) Date: Sep. 23, 2011

(87) PCT Pub. No.: WO2010/110409
PCT Pub. Date: Sep. 30, 2010

(65) Prior Publication Data
US 2012/0022251 A1    Jan. 26, 2012

(30) Foreign Application Priority Data

Mar. 26, 2009 (JP) ................. 2009-075290
Jun. 15, 2009 (JP) ................. 2009-142166

(51) Int. Cl.
| C07D 213/79 | (2006.01) |
| C07D 213/80 | (2006.01) |
| C07D 471/04 | (2006.01) |
| C07D 309/32 | (2006.01) |
| C07D 405/06 | (2006.01) |
| C07D 498/14 | (2006.01) |

(52) U.S. Cl.
CPC ............ *C07D 213/80* (2013.01); *C07D 471/04* (2013.01); *C07D 309/32* (2013.01); *C07D 405/06* (2013.01); *C07D 498/14* (2013.01)
USPC ........................................................ 546/296

(58) Field of Classification Search
None
See application file for complete search history.

(56) References Cited

U.S. PATENT DOCUMENTS

| 4,524,149 | A | 6/1985 | Lesher et al. |
| 4,603,144 | A | 7/1986 | Campbell et al. |
| 4,735,964 | A | 4/1988 | Campbell et al. |
| 4,769,380 | A | 9/1988 | Jones, Jr. et al. |
| 4,812,474 | A | 3/1989 | Campbell et al. |
| 5,688,815 | A | 11/1997 | Zbinden |
| 6,426,418 | B1 | 7/2002 | Tam et al. |
| 7,211,572 | B2 | 5/2007 | Miyazaki et al. |
| 8,217,034 | B2 | 7/2012 | Johns et al. |
| 8,552,187 | B2 | 10/2013 | Johns et al. |
| 2001/0051732 | A1 | 12/2001 | Muraoka et al. |
| 2004/0167124 | A1 | 8/2004 | Chen et al. |
| 2005/0054645 | A1 | 3/2005 | Miyazaki et al. |
| 2006/0019996 | A1 | 1/2006 | Tucci et al. |
| 2006/0116356 | A1 | 6/2006 | Cai et al. |
| 2006/0252944 | A1 | 11/2006 | Lantzsch et al. |
| 2007/0072831 | A1 | 3/2007 | Cai et al. |
| 2007/0249687 | A1 | 10/2007 | Yoshida |
| 2007/0270485 | A1 | 11/2007 | Wender et al. |
| 2008/0096886 | A1 | 4/2008 | Tam et al. |
| 2008/0161271 | A1 | 7/2008 | Yoshida et al. |
| 2008/0207562 | A1 | 8/2008 | Zander |
| 2009/0143356 | A1 | 6/2009 | Yoshida et al. |
| 2009/0318421 | A1 | 12/2009 | Johns et al. |
| 2011/0124598 | A1 | 5/2011 | Johns et al. |
| 2011/0183940 | A1 | 7/2011 | Johns et al. |
| 2011/0190236 | A1 | 8/2011 | Johns et al. |
| 2011/0282055 | A1 | 11/2011 | Yoshida et al. |

FOREIGN PATENT DOCUMENTS

| CA | 2 379 370 | 9/2003 |
| EP | 0 171 814 | 2/1986 |
| EP | 0768 302 | 4/1997 |
| EP | 1544199 A1 | 6/2005 |
| EP | 2602260 | 6/2013 |
| GB | 2280435 A | 2/1995 |
| JP | 2006-342115 A | 12/2006 |
| JP | 2007-509850 A | 4/2007 |
| JP | 2008-540343 | 11/2008 |
| WO | WO 98/54138 | 12/1998 |
| WO | WO-2004/024078 A2 | 3/2004 |
| WO | WO-2004/024078 A3 | 3/2004 |
| WO | WO-2005/016927 A1 | 2/2005 |
| WO | WO-2005/087766 A1 | 9/2005 |
| WO | WO-2005/092099 A1 | 10/2005 |
| WO | WO-2006/030807 A1 | 3/2006 |
| WO | WO 2006/053429 | 5/2006 |
| WO | WO-2006/066414 A1 | 6/2006 |
| WO | WO-2006/088173 A1 | 8/2006 |
| WO | WO-2006/116764 A1 | 11/2006 |
| WO | WO-2007/049675 A1 | 5/2007 |

(Continued)

OTHER PUBLICATIONS

West, Anthony R., Solid State Chemistry and its Applications, Wiley, New York, 1988, pp. 358 & 365.*
Al-Shaar et al, Journal of the Chemical Society, Perkin Transactions 1: Organic and Bio-Organic Chemistry (1972-1999) (1992), (21), 2789-811.*
Anderson et al., "The Selective Reaction of Aryl Halides with KOH: Synthesis of Phenols, Aromatic Ethers, and Benzofurans," Journal of American Chemical Society, vol. 128, 2006, pp. 10694-10695.
Chen et al., "Palladium-catalyzed C—O bond formation: direct synthesis of phenols and aryl/alkyl ethers from activated aryl halides," Tetrahedron Letters, vol. 48, 2007, pp. 473-476.

(Continued)

*Primary Examiner* — Zinna Northington Davis
(74) *Attorney, Agent, or Firm* — Finnegan, Henderson, Farabow, Garrett & Dunner, LLP

(57) ABSTRACT

The present invention provides a pyrone derivative and a pyridone derivative, which are novel intermediates for synthesizing an anti-influenza drug, a method of producing the same, and a method of using the same.

10 Claims, 3 Drawing Sheets

(56) References Cited

FOREIGN PATENT DOCUMENTS

| WO | WO 2008/103277 | 8/2008 |
|---|---|---|
| WO | WO 2010/011814 | 1/2010 |
| WO | WO 2010/068253 | 6/2010 |
| WO | WO 2010/068262 | 6/2010 |
| WO | WO 2011/119566 | 9/2011 |
| WO | WO 2012/018065 | 2/2012 |

OTHER PUBLICATIONS

DeJohn et al., "Functionalization of Substituted 2(1 *H*)- and 4(1 *H*)-Pyridones. III. The Preparation of Substituted 6-Vinyl-1,2-dihydro-2-oxo- and 1,4-Dihydro-4-oxo-3-pyridinecarboxylic Acids Through the Chemistry of Pyridone Dianions," Journal of Heterocyclic Chemistry, vol. 20, 1983, pp. 1295-1302.

Groundwater et al., "Synthesis and reactions of reduced flavones," Journal of Chemistry Society, Perkin Trans. 1, 1997, pp. 163-169.

Hastings et al., "Anti-Influenza Virus Activities of 4-Substituted 2,4-Dioxobutanoic Acid Inhibitors," Antimicrobial Agents and Chemotherapy, May 1996, vol. 40, No. 5, pp. 1304-1307.

Hensens et al., "Isolation and Structure of Flutimide, a Novel Endonuclease Inhibitor of Influenza Virus," Tetrahedron Letters, vol. 36, No. 12, 1995, pp. 2005-2008.

Keller, P.A., "Product Class 2: Pyridinones and Related Systems," Science of Synthesis, vol. 15, 2005, pp. 285-387.

McCleland et al., "Comparison of $N,N'$-diarylsguaramides and $N,N'$-diarylureas as antagonists of the CXCR2 chemokine receptor," Bioorganic & Medicinal Chemistry Letters, vol. 17, 2007, pp. 1713-1717.

McCombie et al., "Generation and in Situ Acylation of Enaminone Anions: A Convenient Synthesis of 3-Carbethoxy-4(1 *H*)-pyridinones and -4-pyrones and Related Compounds," Journal of Organic Chemistry, vol. 56, 1991, pp. 4963-4967.

Parkes et al., Use of a Pharmacophore Model to Discover a New Class of Influenza Endonuclease Inhibitors, J. Med. Chem. 2003, vol. 46, pp. 1153-1164.

Ross et al., "The Synthesis and Rearrangement of Epoxypyrones," Tetrahedron Letters, vol. 22, No. 23, 1981, pp. 2207-2208.

Singh, Sheo B., "Total Synthesis of Flutimide, A Novel Endonuclease Inhibitor of Influenza Virus," Tetrahedron Letters, vol. 36, No. 12, 1995, pp. 2009-2012.

Thomassini et al., "Inhibition of Cap ($m^7$GpppXm)-Dependent Endonuclease of Influenza Virus by 4-Substitited 2,4-Dioxobutanoic Acid Compounds," Antimicrobial Agents and Chemotherapy, vol. 38, No. 12, Dec. 1994, pp. 2827-2837.

Wai et al., "Dihydroxypyridopyrazine-1,6-dione HIV-1 integrase inhibitors," Bioorganic & Medicinal Chemistry Letters 17, 2007, pp. 5595-5599.

International Search Report for International Application No. PCT/JP2010/055316, mailed Jun. 29, 2010.

Ex Parte Quayle Action mailed on Jan. 2, 2013, in U.S Appl. No. 13/054,847.

Notice of Allowance mailed on Apr. 5, 2013, in U.S. Appl. No. 13/054,847.

Notice of Allowance mailed on Jul. 3, 2013, in U.S. Appl. No. 13/054,847.

Notice of Allowance mailed on Jun. 6, 2013, in U.S. Appl. No. 13/128,457.

Notice of Allowance mailed on Sep. 9, 2013 in U.S. Appl. No. 13/128,992.

Ex Parte Quayle Action mailed on Jul. 11, 2013 in U.S. Appl. No. 13/128,992.

Ex Parte Quayle Action mailed on May 17, 2013 in U.S. Appl. No. 13/128,992.

Notice of Allowance mailed on Mar. 19, 2012, in U.S. Appl. No. 13/054,633.

Non-final Office Action mailed on Dec. 7, 2011, in U.S. Appl. No. 3/054,633.

H. Wang et al., co-pending U.S. Appl. No. 13/636,237, filed Sep. 20, 2012, published as WO 2011/119566.

Sumino et al., Copending U.S. Appl. No. 13/814,333, filed Feb. 5, 2013 published as WO 2012/018065.

M. Ghandi et al., "A Novel Method for the Synthesis of Formyl and Hydroxymethyl Derivatives 4*H*-Pyran-4-One," Organic Preparations and Procedures International, vol. 34, No. 5, pp. 525-530 (2002).

S. Kukolja et al., "Studies on 4-Pyrones and 4-Pyridones. II. The Preparation and Rearrangement of 3-Allyloxy-4-Pyrone," Croatica Chemica Acta, vol. 33, pp. 229-233 (1961).

Supplementary European Search Report issued Dec. 6, 2011, in EP Application No. 09800991.3.

J. D. Thomas et al., "Overcoming Steric Effects in the Coupling Reaction of Alkyloxycarbonyloxymethyl (AOCOM) Halides with Phenols: An Efficient Synthesis of AOCOM Phenolic Prodrugs," Tetrahedron Letters, vol. 48, No. 1, pp. 109-112 (Nov. 30, 2006).

J. D. Thomas, "Improving the Topical Delivery of Phenol-Containing Drugs: An Alkylcarbonyloxymethyl and Alkyloxycarbonyloxymethyl Prodrug Approach," University of Florida, 150 page (Dec. 31, 2006).

Y. K. Ko et al., "A New and Facile Synthesis of 2-Pyridones," Bull. Korean Chem. Soc., vol. 22, No. 2, pp. 234-236 (2001).

L. L. Woods et al., "Reactions of Pyrones Catalyzed by Trifluoroacetic Acid," J. Org. Chem., pp. 1052-1053, (Jun. 1960).

Supplementary European Search Report and Written Opinion issued Nov. 15, 2013, in EP Application No. 10756205.0.

\* cited by examiner

METHOD OF PRODUCING PYRONE AND PYRIDONE DERIVATIVES

CONTINUING DATA

This application is a 371 application of PCT/JP2010/055316 filed Mar. 26, 2010.

TECHNICAL FIELD

The present invention relates to a pyrone derivative and a pyridone derivative, which are novel intermediates for synthesizing an anti-influenza drug exhibiting the cap-dependent endonuclease inhibitory activity, a method of producing the same, and a method of using the same.

BACKGROUND ART

Influenza is an acute respiratory infectious disease caused by infection with an influenza virus. In Japan, there is a report of a few millions of influenza-like patients every winter, and influenza is accompanied with high morbidity and mortality. Influenza is a particularly important disease in a high risk population such as baby and elderly, a complication rate with pneumonia is high in elderly, and death with influenza is occupied with elderly in many cases.

As anti-influenza drugs, Symmetrel (trade name: Amantadine) and Flumadine (trade name: Rimantadine) which inhibit the denucleation process of a virus, and Oseltamivir (trade name: Tamiflu) and Zanamivir (trade name: Relenza) which are neuraminidase inhibitors suppressing virus budding and release from a cell are known. However, since problems of appearances of resistant strains and side effects, and worldwide epidemic of a new-type influenza virus having high pathogenicity and mortality are feared, development of an anti-influenza drug having a novel mechanism has been desired.

Since a cap-dependent endonuclease which is an influenza virus-derived enzyme is essential for virus proliferation, and has the virus-specific enzymatic activity which is not possessed by a host, it is believed that the endonuclease is suitable for a target of an anti-influenza drug. The cap-dependent endonuclease has a host mRNA precursor as a substrate, and has the endonuclease activity of producing a fragment of 9 to 13 bases including a cap structure (not including the number of bases of the cap structure). This fragment functions as a primer of a virus RNA polymerase, and is used in synthesizing mRNA encoding a virus protein. That is, it is believed that a substance which inhibits the cap-dependent endonuclease inhibits synthesis of a virus protein by inhibiting synthesis of virus mRNA and, as a result, inhibits virus proliferation.

As the substance which inhibits the cap-dependent endonuclease, flutamide (Patent Document 1 and Non-Patent Documents 1 and 2) and 4-substituted 2,4-dioxobutanoic acid (Non-Patent Documents 3 to 5) are reported, but they have not yet led to clinical use as anti-influenza drugs. In addition, Patent Documents 2 to 11 and Non-Patent Document 6 describe compounds having a similar structure to that of a novel anti-influenza drug exhibiting the cap-dependent endonuclease inhibitory activity, and a method of producing the same. In addition, a pyrone derivative and a pyridone derivative are disclosed in Non-Patent Documents 7 to 9.

PRIOR ART DOCUMENTS

Patent Documents

[Patent Document 1] GB No. 2280435 specification
[Patent Document 2] International Publication No. 2007/049675 pamphlet
[Patent Document 3] International Publication No. 2006/088173 pamphlet
[Patent Document 4] International Publication No. 2006/066414 pamphlet
[Patent Document 5] International Publication No. 2005/092099 pamphlet
[Patent Document 6] International Publication No. 2005/087766 pamphlet
[Patent Document 7] International Publication No. 2005/016927 pamphlet
[Patent Document 8] International Publication No. 2004/024078 pamphlet
[Patent Document 9] International Publication No. 2006/116764 pamphlet
[Patent Document 10] International Publication No. 2006/030807 pamphlet
[Patent Document 11] Japanese Patent Laid-open Publication No. 2006-342115

Non-Patent Documents

[Non-Patent Document 1] Tetrahedron Lett 1995, 36(12), 2005
[Non-Patent Document 2] Tetrahedron Lett 1995, 36(12), 2009
[Non-Patent Document 3] Antimicrobial Agents And Chemotherapy, December 1994, p. 2827-2837
[Non-Patent Document 4] Antimicrobial Agents And Chemotherapy, May 1996, p. 1304-1307
[Non-Patent Document 5] J. Med. Chem. 2003, 46, 1153-1164
[Non-Patent Document 6] Bioorganic & Medicinal Chemistry Letters 17 (2007)5595-5599
[Non-Patent Document 7] Journal of Organic Chemistry 1960, 25, p. 1052-1053
[Non-Patent Document 8] Tetrahedron Lett 1981, 22(23), 2207
[Non-Patent Document 9] Journal of Organic Chemistry 1991, 56, p. 4963-4967

SUMMARY OF THE INVENTION

Problems to be Solved by the Invention

An object of the present invention is to provide a novel pyrone derivative and a novel pyridone derivative, which are novel intermediates for synthesizing an anti-influenza drug, a method of producing the same, and a method of using the same. Specifically, the object is to efficiently produce compounds and the like useful as an anti-influenza drug, which are exemplified by formula (I), formula (II) or formula (III):

[Chemical formula 1]

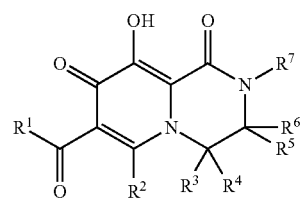

(I)

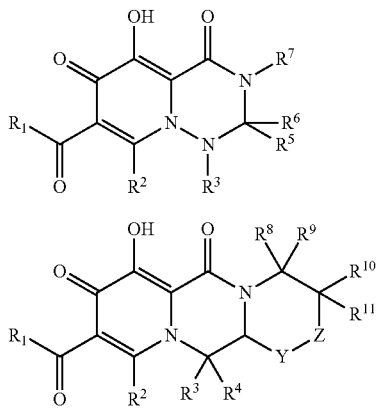

(wherein $R^1$ is lower alkyloxy optionally substituted by substituent E, carbocyclyl lower alkyloxy optionally substituted by substituent E, heterocyclyl lower alkyloxy optionally substituted by substituent E, carbocyclyl lower alkylamino optionally substituted by substituent E, or heterocyclyl lower alkylamino optionally substituted by substituent E, Z is $CR^{12}R^{13}$, or a single bond, Y is $CH_2$, an oxygen atom, or N—$R^{14}$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are each independently hydrogen, lower alkyl optionally substituted by substituent E, lower alkenyl optionally substituted by substituent E, lower alkynyl optionally substituted by substituent E, carbocyclyl lower alkyl optionally substituted by substituent E, or heterocyclyl lower alkyl optionally substituted by substituent E, $R^3$ and $R^5$ may be taken together to form 4 to 8-membered carbocyclyl optionally substituted by substituent E, or 4 to 8-membered heterocyclyl optionally substituted by substituent E, or $R^7$ and $R^8$ may be taken together to form 4 to 8-membered heterocyclyl optionally substituted by substituent E, wherein when Z is a single bond, $R^{14}$ and $R^{10}$ may be taken together to form 4 to 8-membered heterocyclyl optionally substituted by substituent E.

Substituent E: halogen, cyano, hydroxy, carboxy, formyl, amino, oxo, nitro, lower alkyl, halogeno lower alkyl, lower alkyloxy, carbocyclyl optionally substituted by substituent F, heterocyclyl optionally substituted by substituent F, carbocyclyl lower alkyloxy optionally substituted by substituent F, heterocyclyl lower alkyloxy optionally substituted by substituent F, carbocyclyl lower alkylthio optionally substituted by substituent F, heterocyclyl lower alkylthio optionally substituted by substituent F, carbocyclyl lower alkylamino optionally substituted by substituent F, heterocyclyl lower alkylamino optionally substituted by substituent F, carbocyclyloxy optionally substituted by substituent F, heterocyclyloxy optionally substituted by substituent F, carbocyclylcarbonyl optionally substituted by substituent F, heterocyclylcarbonyl optionally substituted by substituent F, carbocyclylaminocarbonyl optionally substituted by substituent F, heterocyclylaminocarbonyl optionally substituted by substituent F, halogeno lower alkyloxy, lower alkyloxy lower alkyl, lower alkyloxy lower alkyloxy, lower alkylcarbonyl, lower alkyloxycarbonyl, lower alkyloxycarbonylamino, lower alkylcarbonylamino, lower alkylaminocarbonyl, lower alkylsulfonyl, and lower alkylsulfonylamino;

Substituent F: halogen, hydroxy, carboxy, amino, oxo, nitro, lower alkyl, halogeno lower alkyl, lower alkyloxy, and amino protective group).

Means for Solving the Problems

The present invention provides the following items.
(Item 1)
A method of producing a compound shown by formula (X4) or a salt thereof, comprising steps of:
(Step B)
reacting a compound shown by formula (X2):

[Chemical formula 2]

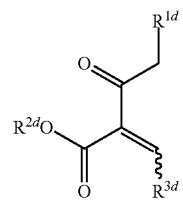

(X2)

(wherein $R^{1d}$ is hydrogen, halogen, lower alkyloxy optionally substituted by substituent E, carbocyclyl lower alkyloxy optionally substituted by substituent E, heterocyclyl lower alkyloxy optionally substituted by substituent E, or —OSi$(R^{1e})_3$, $R^{1e}$s are each independently lower alkyl optionally substituted by substituent E, carbocyclyl optionally substituted by substituent E, heterocyclyl optionally substituted by substituent E, carbocyclyl lower alkyl optionally substituted by substituent E or heterocyclyl lower alkyl optionally substituted by substituent E, $R^{2d}$ is hydrogen, lower alkyl optionally substituted by substituent E, carbocyclyl lower alkyl optionally substituted by substituent E, or heterocyclyl lower alkyl optionally substituted by substituent E, $R^{3d}$ is hydrogen, lower alkyl optionally substituted by substituent E, —N$(R^{3e})_2$, or —OR$^{3e}$, $R^{3e}$s are each independently lower alkyl optionally substituted by substituent E, or may be taken together to form a heterocycle, and wavy line is E form and/or Z form or the mixture thereof.

Substituent E; halogen, cyano, hydroxy, carboxy, formyl, amino, oxo, nitro, lower alkyl, halogeno lower alkyl, lower alkyloxy, carbocyclyl optionally substituted by substituent F, heterocyclyl optionally substituted by substituent F, carbocyclyl lower alkyloxy optionally substituted by substituent F, heterocyclyl lower alkyloxy optionally substituted by substituent F, carbocyclyl lower alkylthio optionally substituted by substituent F, heterocyclyl lower alkylthio optionally substituted by substituent F, carbocyclyl lower alkylamino optionally substituted by substituent F, heterocyclyl lower alkylamino optionally substituted by substituent F, carbocyclyloxy optionally substituted by substituent F, heterocyclyloxy optionally substituted by substituent F, carbocyclylcarbonyl optionally substituted by substituent F, heterocyclylcarbonyl optionally substituted by substituent F, carbocyclylaminocarbonyl optionally substituted by substituent F, heterocyclylaminocarbonyl optionally substituted by substituent F, halogeno lower alkyloxy, lower alkyloxy lower alkyl, lower alkyloxy lower alkyloxy, lower alkylcarbonyl, lower alkyloxycarbonyl, lower alkyloxycarbonylamino, lower alkylamino, lower alkylcarbonylamino, lower alkylaminocarbonyl, lower alkylsulfonyl, and lower alkylsulfonylamino;

Substituent F: halogen, hydroxy, carboxy, amino, oxo, nitro, lower alkyl, halogeno lower alkyl, lower alkyloxy, and amino protective group) with a compound shown by formula (V2);

[Chemical formula 3]

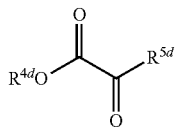

(V2)

(wherein $R^{4d}$ is lower alkyl optionally substituted by substituent E, carbocyclyl lower alkyl optionally substituted by substituent E, or heterocyclyl lower alkyl optionally substituted by substituent E, $R^{5d}$ is hydrogen, halogen, lower alkyloxy optionally substituted by substituent E, or —O—SO$_2$—$R^{5e}$, $R^{5e}$ is lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl optionally substituted by substituent E, and substituent E is defined above)

to obtain a compound shown by formula (X3):

[Chemical formula 4]

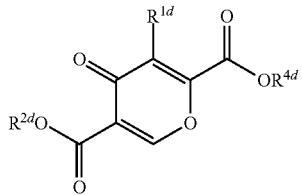

(X3)

(wherein each symbol is defined above); and (Step C) reacting the compound shown by formula (X3) with a compound shown by formula (V3):

[Chemical formula 5]

H$_2$N—$R^{6d}$ (V3)

(wherein $R^{6d}$ is lower alkyl optionally substituted by substituent E, lower alkenyl optionally substituted by substituent E, amino optionally substituted by substituent E, lower alkylamino optionally substituted by substituent E, carbocyclyl optionally substituted by substituent E, or heterocyclyl optionally substituted by substituent E, and substituent E is defined above)

to obtain a compound shown by formula (X4):

[Chemical formula 6]

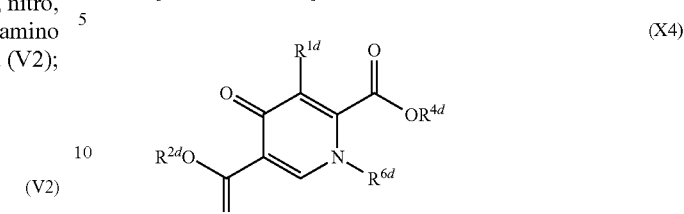

(X4)

(wherein each symbol is defined above).

(Item 2)
A method according to Item 1, wherein Step B and Step C are continuously performed.

(Item 3)
A method of producing a compound shown by formula (XA4), or a salt thereof:

[Chemical formula 10]

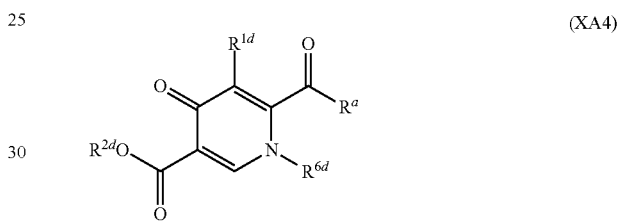

(XA4)

(wherein $R^a$ is hydrogen, hydroxy, lower alkylamino optionally substituted by substituent E, lower alkenylamino optionally substituted by substituent E, lower alkynylamino optionally substituted by substituent E, carbocyclyl lower alkylamino optionally substituted by substituent E, or heterocyclyl lower alkylamino optionally substituted by substituent E, and each symbol is defined above)

comprising the step of:

reacting a compound shown by formula (X2):

[Chemical formula 7]

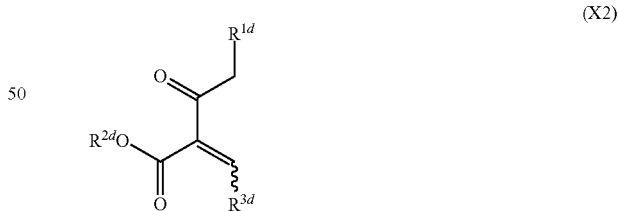

(X2)

(wherein each symbol is defined above)

with a compound shown by formula (VA2):

[Chemical formula 8]

(VA2)

(wherein $R^{4e}$s are each independently hydrogen, lower alkyl optionally substituted by substituent E, carbocyclyl optionally substituted by substituent E, or heterocyclyl optionally substituted by substituent E, and $R^{5d}$ and substituent E are defined above); and reacting with a compound shown by formula (V3);

[Chemical formula 9]

H$_2$N—R$^{6d}$ (V3)

(wherein $R^{6d}$ is defined above).

(Item 4)

A method of producing a compound shown by formula (X3) or formula (XA3), or a salt thereof;

[Chemical formula 13]

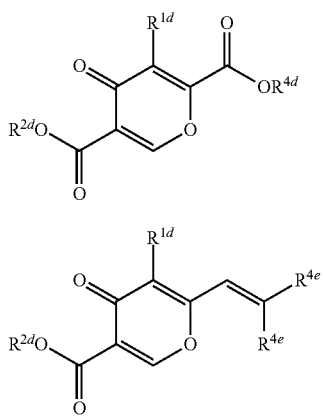

(X3)

(XA3)

(wherein each symbol is defined in Item 1)
comprising reacting a compound shown by formula (X2);

[Chemical formula 11]

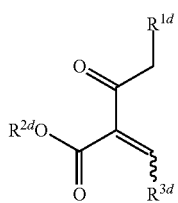

(X2)

(wherein each symbol is defined in Item 1)
with a compound shown by formula (V2) or formula (VA2):

[Chemical formula 12]

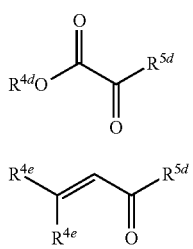

(V2)

(VA2)

(wherein each symbol is defined in Item 1).

(Item 5)

A method of producing a compound shown by formula (X4) or formula (XA4), or a salt thereof:

[Chemical formula 16]

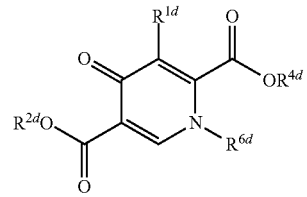

(X4)

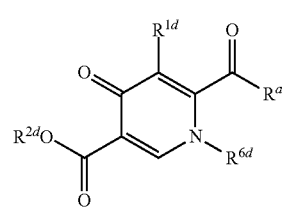

(XA4)

(wherein each symbol is defined in Item 1 and Item 3)
comprising the step of reacting a compound shown by formula (X3) or formula (XA3):

[Chemical formula 14]

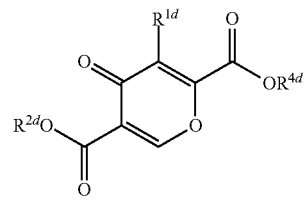

(X3)

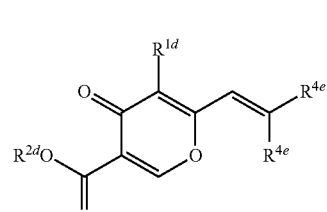

(XA3)

(wherein each symbol is defined in Item 1)
or the derivative of formula (XA3) with a compound shown by formula (V3):

[Chemical formula 15]

H$_2$N—R$^{6d}$ (V3)

(wherein each symbol is defined in Item 1).

(Item 6)

A method of producing a compound shown by formula (X4') or formula (XA4'), or a salt thereof:

[Chemical formula 20]

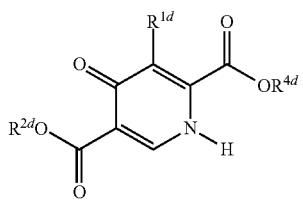
(X4')

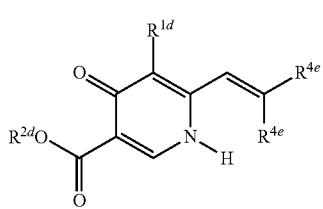
(XA4')

(wherein each symbol is defined in Item 1)
comprising reacting a compound shown by formula (X2):

[Chemical formula 17]

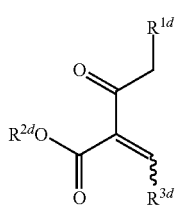
(X2)

(wherein each symbol is defined in Item 1)
with a compound shown by formula (V2) or formula (VA2):

[Chemical formula 18]

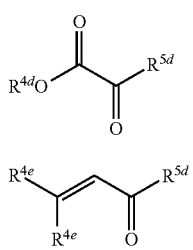
(V2)

(VA2)

(wherein each symbol is defined in Item 1)
and a compound shown by formula (V2'):

[Chemical formula 19]

$NH^{4+}X^{d-}$ (V2')

(wherein $X^{d-}$ is counter anion of ammonium cation).

(Item 7)

A method of producing a compound shown by formula (X4) or formula (XA4), or a salt thereof:

[Chemical formula 23]

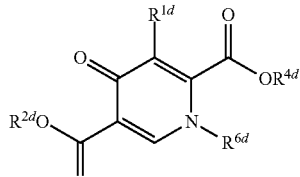
(X4)

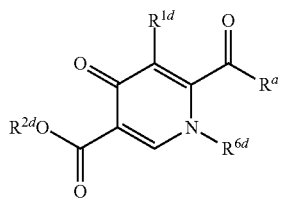
(XA4)

(wherein each symbol is defined in Item 1 or Item 3)
comprising the step of:
  reacting the compound shown by formula (X4') or formula (XA4'):

[Chemical formula 21]

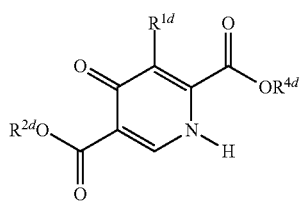
(X4')

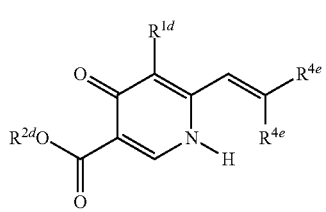
(XA4')

(wherein each symbol is defined in Item 1)
obtained in the production method as defined in Item 6, or the derivative of formula (XA4') with a compound shown by formula (V3'):

[Chemical formula 22]

$R^{6d}-L^d$ (V3')

(wherein $R^{6d}$ is defined in Item 1,
  $L^d$ is a leaving group, and Ph is a phenyl group).
(Item 8)

A method according to Item 1, 2, 3, 4 or Item 6, wherein the compound shown by formula (X2) is obtained by reacting a compound shown by formula (X1):

[Chemical formula 24]

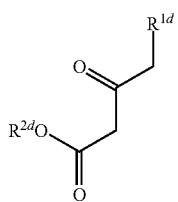

(X1)

(wherein each symbol is defined in Item 1)
with a compound shown by formula (V1):

[Chemical formula 25]

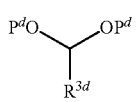

(V1)

(wherein $P^d$ is lower alkyl optionally substituted by substituent E, and $R^{3d}$ and substituent E are defined in Item 1).

(Item 9)
A method according to Item 1, 2, 3, 4 or Item 6, wherein the compound shown by formula (X2) is obtained by reacting a compound shown by formula (Z1):

[Chemical formula 26]

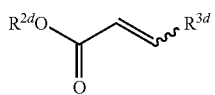

(Z1)

(wherein each symbol is defined in Item 1)
with a compound shown by formula (Z2):

[Chemical formula 27]

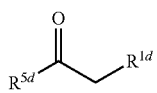

(Z2)

(wherein each symbol is defined in Item 1).

(Item 10)
A compound shown by formula (X3), or a pharmaceutically acceptable salt thereof or solvate thereof:

[Chemical formula 28]

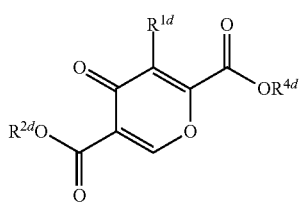

(X3)

(wherein each symbol is defined in Item 1).

(Item 11)
A compound shown by formula (X4), or a pharmaceutically acceptable salt thereof or solvate thereof:

[Chemical formula 29]

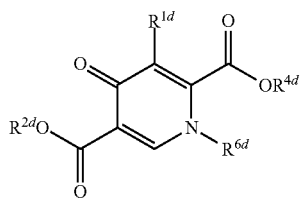

(X4)

(wherein each symbol is defined in Item 1).

(Item 12)
A compound shown by formula (X4'), or a pharmaceutically acceptable salt thereof or solvate thereof:

[Chemical formula 30]

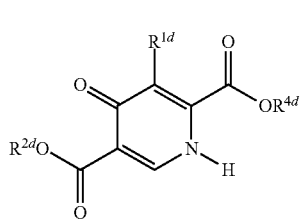

(X4')

(wherein each symbol is defined in claim 1).

(Item 13)
A crystal of a compound shown by formula (1D) or a solvate thereof:

[Chemical formula 31]

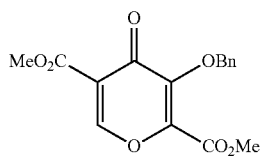

(1D)

(wherein Me is a methyl group, and Bn is a benzyl group),
wherein the compound has a peak at a diffraction angle (2θ): 7.9°±0.2°, 10.0°±0.2°, 11.5°±0.2°, 20.0°±0.2°, 23.4°±0.2° and 34.0°±0.2° in a powder X-ray diffraction spectrum.

(Item 14)
A crystal of a compound shown by formula (2D) or a solvate thereof:

[Chemical formula 32]

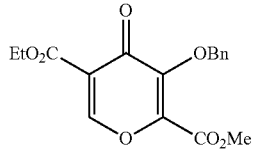

(2D)

(wherein Me is a methyl group, Et is an ethyl group, and Bn is a benzyl group), wherein the compound has a peak at a diffraction angle (2θ): 17.6°±0.2°, 25.2°±0.2°, 26.4°±0.2° and 28.1°±0.2° in a powder X-ray diffraction spectrum.

(Item 15)

A crystal of a compound shown by formula (9C') or a solvate thereof:

[Chemical formula 33]

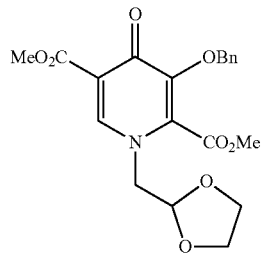

(9C')

(wherein Me is a methyl group, and Bn is a benzyl group), wherein the compound has a peak at a diffraction angle (2θ): 14.2°±0.2°, 16.0°±0.2°, 22.0°±0.2°, 22.2°±0.2°, 24.4°±0.2° and 25.9°±0.2° in a powder X-ray diffraction spectrum.

(Item 16)

A crystal according to Item 13, which is characterized by a powder X-ray diffraction spectrum which is substantially consistent with FIG. 1.

(Item 17)

A crystal according to Item 14, which is characterized by a powder X-ray diffraction spectrum which is substantially consistent with FIG. 2.

(Item 18)

A crystal according to Item 15, which is characterized by a powder X-ray diffraction spectrum which is substantially consistent with FIG. 3.

Effect of the Invention

The production method according to the present invention is a method that can produce compounds included in the formula (I), the formula (II) or the formula (III) etc., which are novel anti-influenza drugs, at a high yield, efficiently, and/or in a short step. In addition, by performing the production method according to the present invention, there are a plurality of advantages that use of a reaction reagent accompanying with toxicity can be avoided, a reaction accompanying with a risk can be avoided, use of an expensive reaction reagent can be avoided, and use of an environmentally harmful reagent and solvent can be avoided, etc. The pyrone derivative (X3), and the pyridone derivative (X4) and/or (X4') which are the present compound have versatility, and are useful as common intermediates at production of the compounds included in the formula (I), the formula (II) or the formula (III). Furthermore, the pyrone derivative (X3) and/or the pyridone derivative (X4) can be also obtained as a crystal. Since these crystals have small hygroscopy, and exhibit high stability to light and heat, they have advantages that storage and handling in production are excellent and the like. Therefore, the production method as well as intermediates and crystals thereof according to the present invention are useful in industrially producing medicaments (anti-influenza drugs, anti-HIV drugs, anti-inflammatory drugs, tranquilizers, anti-tumor drugs etc.).

[Chemical formula 34]

(X3)

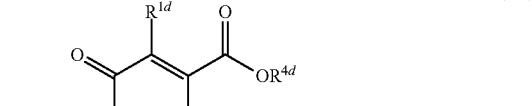

(X4)

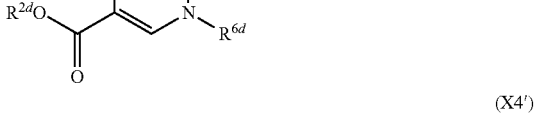

(X4')

(wherein each symbol is defined above)

MODE FOR CARRYING OUT THE INVENTION

Figure 1:
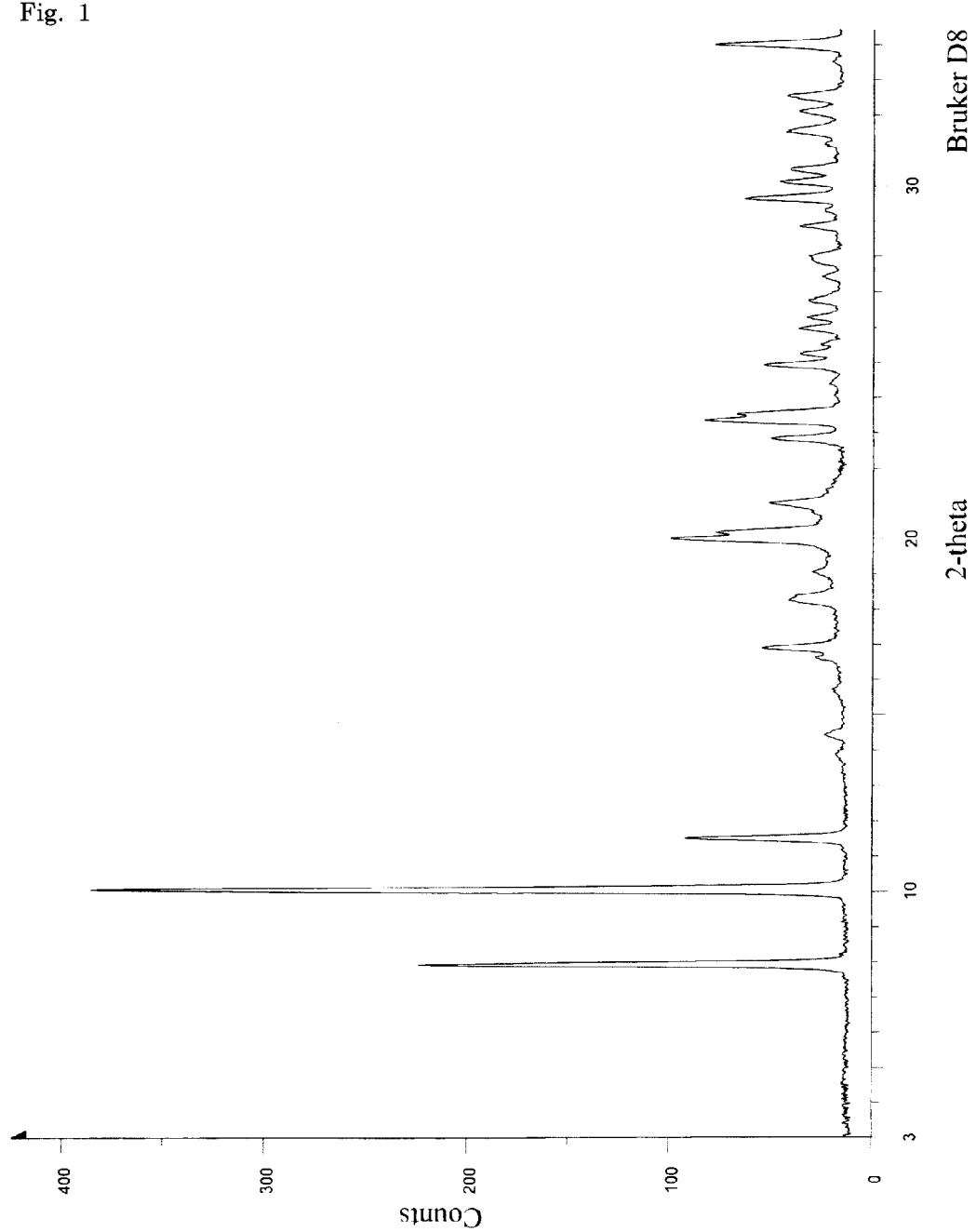
FIG. 1 is a powder X-ray pattern of Compound 1D obtained in Example 1. An ordinate indicates a peak intensity, and an abscissa indicates a diffraction angle (2θ).
Figure 2:
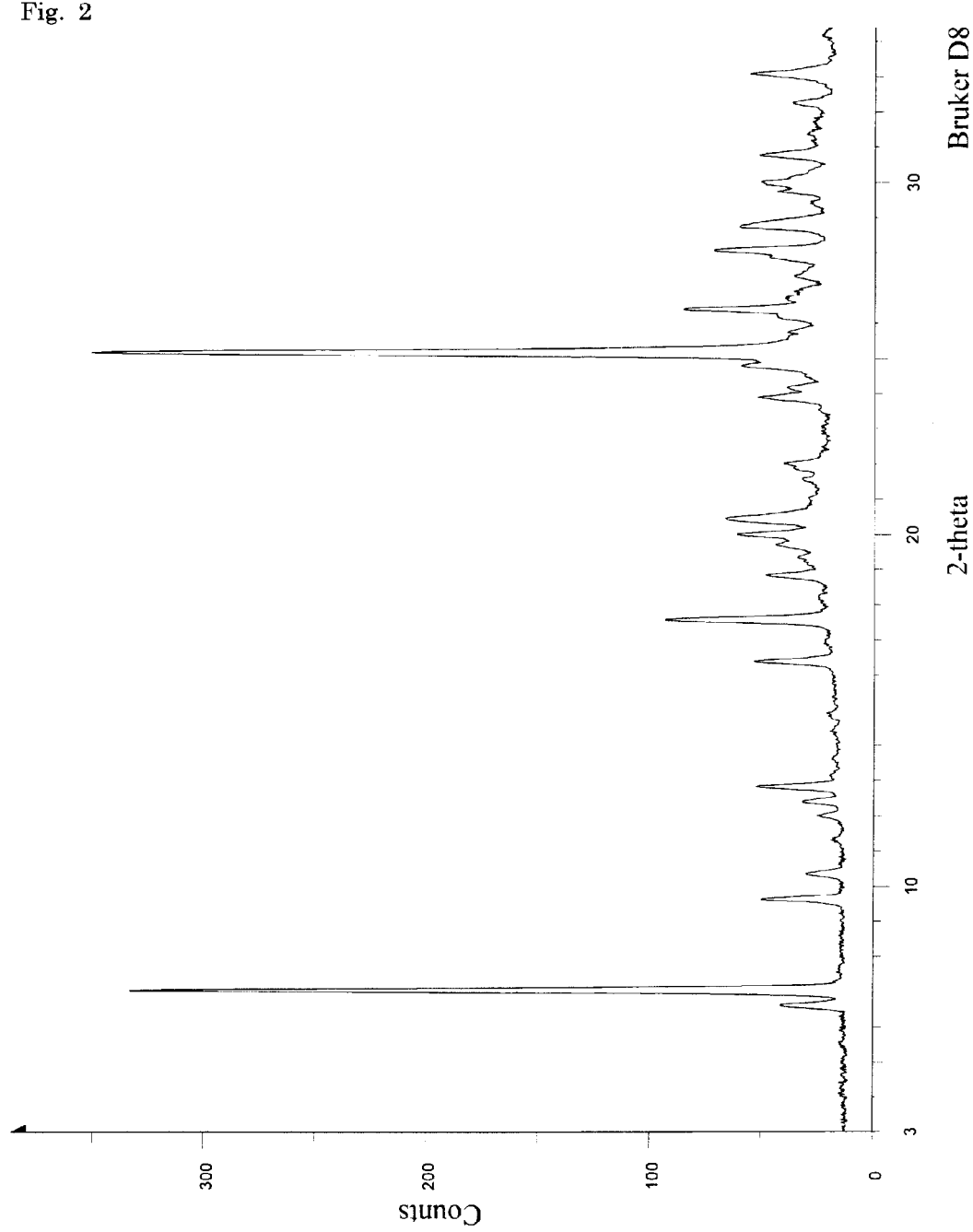
FIG. 2 is a powder X-ray pattern of Compound 2D obtained in Example 2. An ordinate indicates a peak intensity, and an abscissa indicates a diffraction angle (2θ).
Figure 3:
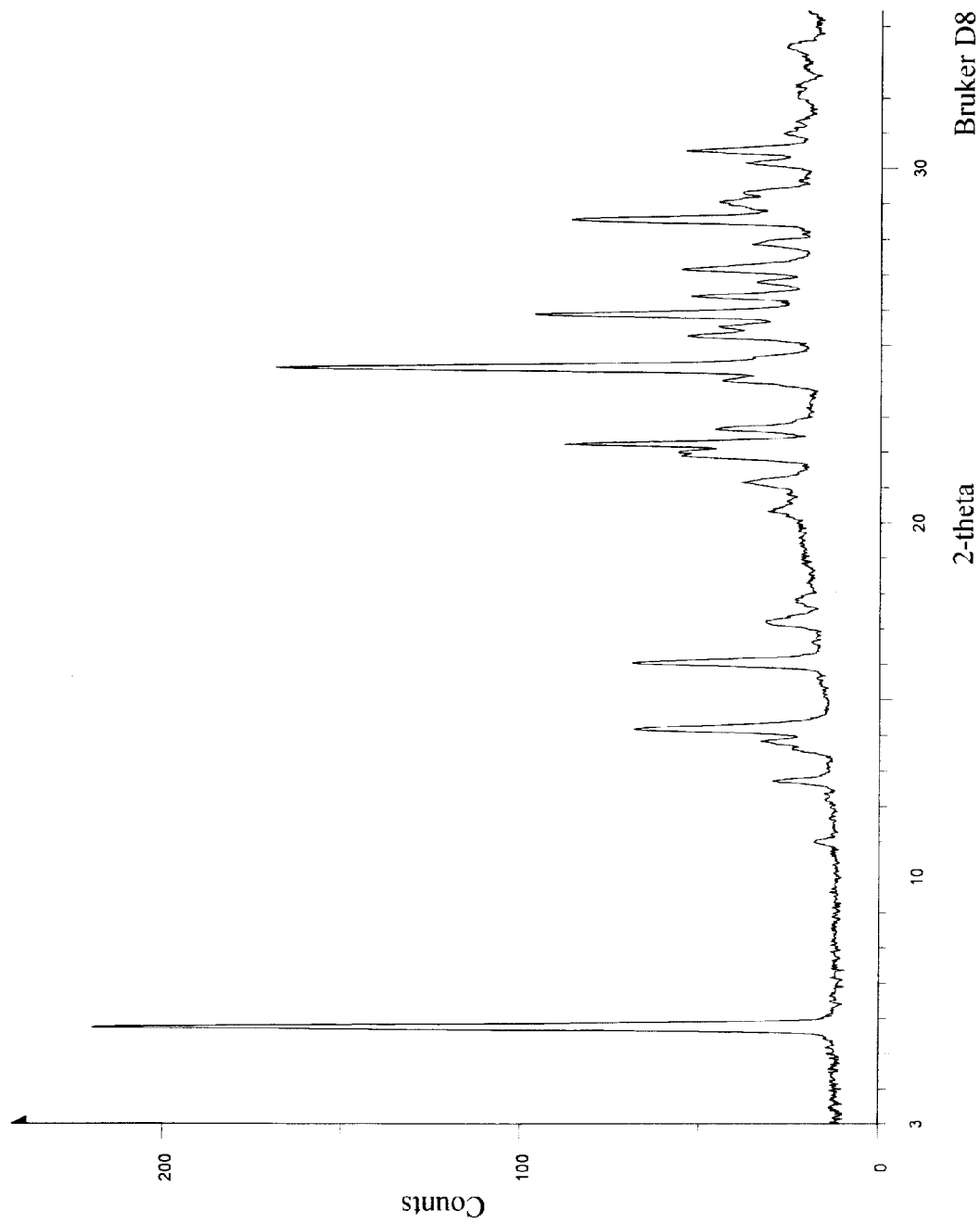
FIG. 3 is a powder X-ray pattern of Compound 9C' obtained in Example 9. An ordinate indicates a peak intensity, and an abscissa indicates a diffraction angle (2θ).

In the present specification, the "halogen" contains a fluorine atom, a chlorine atom, a bromine atom and an iodine atom.

In the present specification, the "lower alkyl" includes straight or branched alkyl having a carbon number of 1 to 15, preferably a carbon number of 1 to 10, more preferably a carbon number of 1 to 6, further preferably a carbon number of 1 to 4, and examples thereof include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl.

Examples of a preferable aspect of the "lower alkyl" include methyl, ethyl, n-propyl, isopropyl, n-butyl, isobutyl, sec-butyl, tert-butyl and n-pentyl. Examples of a further preferable aspect include methyl, ethyl, n-propyl, isopropyl and tert-butyl.

In the present specification, the "lower alkenyl" includes straight or branched alkenyl having one or more double bonds at arbitrary positions and having 2 to 15 carbon atoms, preferably 2 to 10 carbon atoms, more preferably 2 to 6 carbon atoms, further preferably 2 to 4 carbon atoms. Specifically, examples thereof include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl and pentadecenyl. Examples of a preferable aspect of the "lower alkenyl" include vinyl, allyl, propenyl, isopropenyl and butenyl.

In the present specification, the "lower alkynyl" includes straight or branched alkynyl having a carbon number of 2 to 10, preferably a carbon number of 2 to 8, further preferably a carbon number of 3 to 6, having one or more triple bonds at arbitrary positions. Specifically, examples thereof include ethynyl, propynyl, butynyl, pentynyl, hexynyl, heptynyl, octynyl, nonynyl and decynyl. These may further have a double bond at an arbitrary position. Examples of a preferable aspect of the "lower alkynyl" include ethynyl, propynyl, butynyl and pentynyl.

In the present specification, lower alkyl parts of the "lower alkyloxy", the "lower alkylcarbonyl", the "lower alkyloxycarbonyl", the "carbocyclyl lower alkyl", the "heterocyclyl lower alkyl", the "carbocyclyloxy lower alkyl", the "heterocyclyloxy lower alkyl", the "halogeno lower alkyl", the "carbocyclyl lower alkyloxy", the "heterocyclyl lower alkyloxy", the "carbocyclyl lower alkylthio", the "heterocyclyl lower alkylthio", the "carbocyclyl lower alkylamino", the "heterocyclyl lower alkylamino", the "halogeno lower alkyloxy", the "lower alkyloxy lower alkyl", the "lower alkyloxy lower alkyloxy", the "lower alkylcarbonyl", the "lower alkyloxycarbonyl", the "lower alkylamino", the "lower alkylcarbonylamino", the "lower alkylaminocarbonyl", the "lower alkyloxycarbonylamino", the "lower alkylsulfonyl" and the "lower alkylsulfonylamino" are also the same as the "lower alkyl".

In the present specification, a lower alkenyl part of the "lower alkenylamino" is also the same as the "lower alkenyl".

In the present specification, a lower alkynyl part of the "lower alkynyl amino" is also the same as the "lower alkynyl".

In the present specification, halogen parts of the "halogeno lower alkyl" and the "halogeno lower alkyloxy" are the same as the aforementioned "halogen". Herein, arbitrary positions on an alkyl group of the "lower alkyl" and the "lower alkyloxy" may be substituted by same or different one or a plurality of halogen atoms, respectively.

In the present specification, the "carbocyclyl" means carbocyclyl having a carbon number of 3 to 20, preferably a carbon number of 3 to 16, more preferably a carbon number of 4 to 12, and includes cycloalkyl, cycloalkenyl, aryl and a non-aromatic fused carbocyclyl.

Specifically, the "cycloalkyl" is carbocyclyl having 3 to 16 carbon atoms, preferably 3 to 12 carbon atoms, more preferably 4 to 8 carbon atoms, and examples thereof include cyclopropyl, cyclobutyl, cyclopentyl, cyclohexyl, cycloheptyl, cyclooctyl, cyclononyl and cyclodecyl.

Specifically, the "cycloalkenyl" includes cycloalkenyl having one or more double bonds at arbitrary positions in a ring of the cycloalkyl, and examples thereof include cyclopropenyl, cyclobutenyl, cyclopentenyl, cyclohexenyl, cycloheptynyl, cyclooctynyl and cyclohexadienyl.

Specifically, the "aryl" includes phenyl, naphthyl, anthryl and phenanthryl and, particularly, phenyl is preferable.

Specifically, the "non-aromatic condensed carbocyclyl" includes a group in which two or more cyclic groups selected from the "cycloalkyl", the "cycloalkenyl" and the "aryl" are condensed, and examples thereof include indanyl, indenyl, tetrahydronaphthyl, fluorenyl, adamantyl and a group shown below.

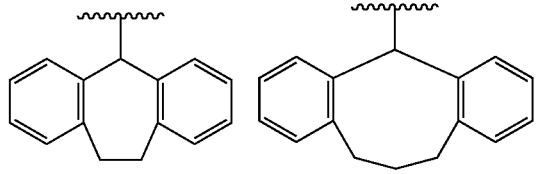

[Chemical formula 35]

Examples of a preferable aspect of the "carbocyclyl" include cycloalkyl, aryl and a non-aromatic fused carbocyclyl and, specifically, examples thereof include cyclopropyl, cyclobutyl, cyclopentyl, cyclohexyl, cycloheptyl and phenyl.

Carbocyclyl parts of the "carbocyclyl lower alkyl", the "carbocyclyl lower alkyloxy", the "carbocyclyl lower alkylthio", the "carbocyclyl lower alkylamino", the "carbocyclyloxy", the "carbocyclylcarbonyl" and the "carbocyclylaminocarbonyl" are as the same as the "carbocyclyl".

In the present specification, the "heterocyclyl" includes heterocyclyl such as heteroaryl, non-aromatic heterocyclyl, bicyclic condensed heterocyclyl and tricyclic condensed heterocyclyl having one or more same or different hetero atoms arbitrarily selected from O, S and N in a ring.

Specifically, examples of the "heteroaryl" include 5 to 6-membered aromatic cyclic groups such as pyrrolyl, imidazolyl, pyrazolyl, pyridyl, pyridazinyl, pyrimidinyl, pyrazinyl, triazolyl, triazinyl, tetrazolyl, furyl, thienyl, isooxazolyl, oxazolyl, oxadiazolyl, isothiazolyl, thiazolyl and thiadiazolyl.

Specifically, examples of the "non-aromatic heterocyclyl" include dioxanyl, thiiranyl, oxyranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl and dioxolanyl.

Specific examples of the "bicyclic fused heterocyclyl" include indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzoisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, thienothienyl, imidazopyridyl, pyrazolopyridyl, thiazolopyridyl, pyrazolopyrimidinyl, pyrazolotriazinyl, pyridazolopyridyl, triazolopyridyl, imidazothiazolyl, pyrazinopyridazinyl, quinazolinyl, quinolyl, isoquinolyl, naphthyridinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxynyl, dihydrobenzoxezinyl, dihydrobenzodioxepinyl and dihydrothienodioxynyl.

Specific examples of the "tricyclic condensed heterocyclyl" include carbazolyl, acridinyl, xanthenyl, phenothiazinyl, phenoxathiinyl, phenoxazinyl, dibenzofuryl, imidazoquinolyl, tetrahydrocarbazolyl, and a group shown below.

[Chemical formula 36]

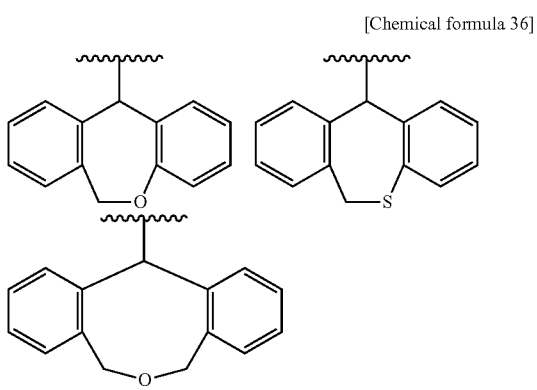

Examples of a preferable aspect of the "heterecyclyl" include 5 to 6-membered heteroaryl or non-aromatic heterocyclyl, and tricyclic fused heterocyclyl.

Heterocyclyl parts of the "heterocyclyl lower alkyl", the "heterocyclyl lower alkyloxy", the "heterocyclyl lower alkylthio", the "heterocyclyl lower alkylamino", the "heterocyclyloxy", the "heterocyclylcarbonyl" and the "heterocyclylaminocarbonyl" are also the same as the "heterocyclyl".

"Step B and Step C are performed continuously" refers to implementation of Step C after implementation of Step B without performing isolation operation and column chromatography purification of a product produced in Step B. A reaction container for performing Step B may be the same as or different from a reaction container for performing Step C.

The "lower alkyl optionally substituted by substituent E" means that the "lower alkyl" is unsubstituted, or one or a plurality of chemically acceptable substituents selected from substituent E are bound thereto. When a plurality of substituents are bound, the plurality of substituents may be the same or different. Examples thereof include methyl, fluoromethyl, trifluoromethyl, chlorodifluoromethyl and

[Chemical formula 37]

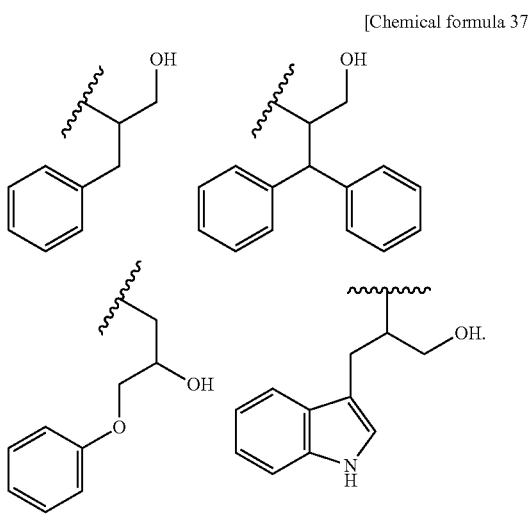

The "carbocyclyl optionally substituted by substituent E" means that the "carbocyclyl" is unsubstituted, or one or a plurality of chemically acceptable substituents selected from substituent E are bound thereto. When a plurality of substituents are bound, the plurality of substituents may be the same or different. Examples thereof include fluorophenyl, difluorophenyl and methoxyfluorophenyl.

The "carbocyclyl lower alkyl optionally substituted by substituent E" means that the "carbocyclyl" and/or the "lower alkyl" are unsubstituted, or one or a plurality of chemically acceptable substituents selected from substituent E are bound. When a plurality of substituents are bound, the plurality of substituents may be the same or different. Examples thereof include 4-fluorobenzyl, 2,4-difluorobenzyl, 4-methoxy-2-fluorobenzyl and 4-methoxyphenyldifluoromethyl.

The "lower alkyloxy optionally substituted by substituent E", the "carbocyclyl lower alkyloxy optionally substituted by substituent E", the "heterocyclyl lower alkyloxy optionally substituted by substituent E", the "lower alkenyl optionally substituted by substituent E", the "amino optionally substituted by substituent E", the "lower alkylamino optionally substituted by substituent E", the "lower alkenylamino optionally substituted by substituent E", the "lower alkynylamino optionally substituted by substituent E", the "carbocyclyl lower alkylamino optionally substituted by substituent E", and the "heterocyclyl lower alkylamino optionally substituted by substituent E" have the same meaning.

The "carbocyclyl optionally substituted by substituent F" means that the "carbocyclyl" is unsubstituted, or one or a plurality of chemically acceptable substituents selected from substituent F are bound thereto. When a plurality of substituents are bound, the plurality of substituents may be the same or different. Examples thereof include fluorophenyl, difluorophenyl and methoxyfluorophenyl.

The "lower alkyloxy optionally substituted by substituent F" means that the "carbocyclyl" part is unsubstituted, or one or a plurality of chemically acceptable substituents selected from substituent F are bound thereto. When a plurality of substituents are bound, the plurality of substituents may be the same or different. Examples thereof include fluorobenzyloxy, difluorobenzyloxy and methoxyfluorobenzyloxy.

The "heterocyclyl optionally substituted by substituent F", the "heterocyclyl lower alkyloxy optionally substituted by substituent F", the "carbocyclyl lower alkylthio optionally substituted by substituent F", the "heterocyclyl lower alkylthio optionally substituted by substituent F", the "carbocyclyl lower alkylamino optionally substituted by substituent F", the "heterocyclyl lower alkylamino optionally substituted by substituent F", the "carbocyclyloxy optionally substituted by substituent F", the "heterocyclyloxy optionally substituted by substituent F", the "carbocyclylcarbonyl optionally substituted by substituent F", the "heterocyclylcarbonyl optionally substituted by substituent F", the "carbocyclylaminocarbonyl optionally substituted by substituent F" and the "heterocyclylaminocarbonyl optionally substituted by substituent F" have the same meaning.

"$R^{3e}$s of —N($R^{3e}$)$_2$ may be taken together to form a heterocycle" includes, for example, the following formulas.

[Chemical formula 38]

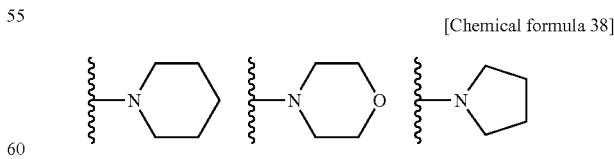

Definition of the "heterocycle" in "$R^{3e}$s of —N($R^{3e}$)$_2$ may be taken together to form a heterocycle" is also the same as described above.

The "amino protective groups" may be general protective groups for an amino group, and are exemplified as amino protective groups described, for example, in Protective Groups in Organic Synthesis, Theodora W Green (John Wiley & Sons). Preferable are a tert-butyloxycarbonyl group and a benzyloxycarbonyl group.

The "carboxyl protective groups" may be general protective groups for an amino group, and are exemplified as carboxyl protective groups described, for example, in Protective Groups in Organic Synthesis, Theodora W Green (John Wiley & Sons). Preferable examples thereof include a methyl group, an ethyl group, a tert-butyl group, a methoxymethyl group, an allyl group, a benzyl group and a p-methoxybenzyl group.

Examples of the "counter anion of ammonium cation" in $X^d$ include halogen$^-$, $CH_3COO^-$, $HCOO^-$, $NO_3^-$, $BF_4^-$, $PF_6^-$, $HO^-$, $Ph\text{-}S\ O_3^-$, $CH_3\text{-}Ph\text{-}S\ O_3^-$, $CH_3\text{—}SO_3^-$, $PO_4^{3-}$, $SO_4^{2-}$ and $HSO_4^-$. Preferable are halogen$^-$, $CH_3COO^-$, $NO_3^-$ and $SO_4^{2-}$. When the anion is divalent or trivalent, the $NH_4^+$ cation indicates one not being charged state by binding of two or three molecules, respectively. Specific examples of the $NH_4^+X^{d-}$ include $(NH_4^+)_2SO_4^{2-}$ and $(NH_4^+)_3PO_4^{3-}$.

The "leaving group" indicates a substituent which is left by a nucleophilic reaction, and examples thereof include halogen, —O—SO$_2$—CH$_3$, —O—SO$_2$—CF$_3$, —O—SO$_2$-Ph and —O—SO$_2$-Ph-C H$_3$. Preferable is halogen.

The "derivative of formula (XA3)" indicates one in which an aldehyde group or a carboxyl group is formed by oxidative cleavage of an olefin site, or amide is formed by condensation reaction with a carboxyl group. Specifically, it is shown in the following formula (XA3a), formula (XA3b) or formula (XA3c):

[Chemical formula 39]

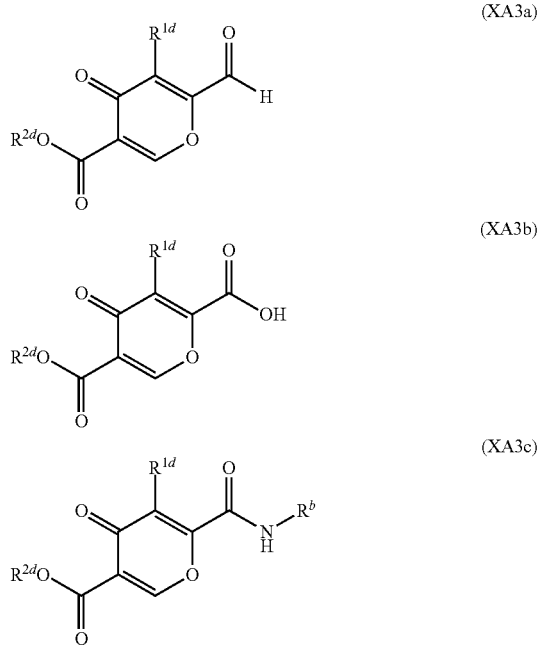

(wherein $R^b$ is hydrogen, lower alkyl optionally substituted by substituent E, lower alkenyl optionally substituted by substituent E, lower alkynyl optionally substituted by substituent E, carbocyclyl lower alkyl optionally substituted by substituent E, or heterocyclyl lower alkyl optionally substituted by substituent E, and other each symbol is defined in Item 1 and Item 3). When the formula (XA3a) is reacted with the formula (V3), the formula (XA4) in which $R^a$ is hydrogen is produced. When the formula (XA3b) is reacted with the formula (V3), the formula (XA4) in which $R^a$ is hydroxy is produced. When the formula (XA3b) is reacted with the formula (V3), the formula (XA4) in which $R^a$ is hydroxy is produced. When the formula (XA3c) is reacted with the formula (V3), the formula (XA4) in which $R^a$ is lower alkylamino optionally substituted by substituent E, lower alkenylamino optionally substituted by substituent E, lower alkynylamino optionally substituted by substituent E, carbocyclyl lower alkylamino optionally substituted by substituent E, or heterocyclyl lower alkylamino optionally substituted by substituent E is produced.

The "oxidative cleavage" in "an aldehyde group or a carboxyl group is formed by oxidative cleavage of an olefin site of the formula (XA3), or amide is formed by condensation reaction with a carboxyl group" can be performed under generally known oxidation reaction condition (e.g. ozone oxidation reaction, RuCl$_3$—NaIO$_4$ oxidation reaction etc.). When the reaction product is an aldehyde form (XA3a), a subsequent general oxidation reaction condition (e.g. Cr$_3$-pyridine, PCC oxidation, SO$_3$-pyridine oxidation, NaClO$_2$ oxidation etc.) can derivatize the olefin site into a carboxyl group.

The "amidation by a condensation reaction" can be performed by a general dehydration condensation reaction (Mitsunobu reaction, reactions using carboxylic acid halide, carboxylic anhydride, or a condensing agent (e.g. WSC, carbonyldiimidazole, dicyclohexylcarbodiimide) etc.).

The "derivative of formula (XA4')" indicates one in which an aldehyde group or a carboxyl group is formed by oxidative cleavage of an olefin site, or amide is formed by condensation reaction with a carboxyl group. Specifically, it is shown in the following formula (XA4'a), formula (XA4'b) or formula (XA4'c):

[Chemical formula 40]

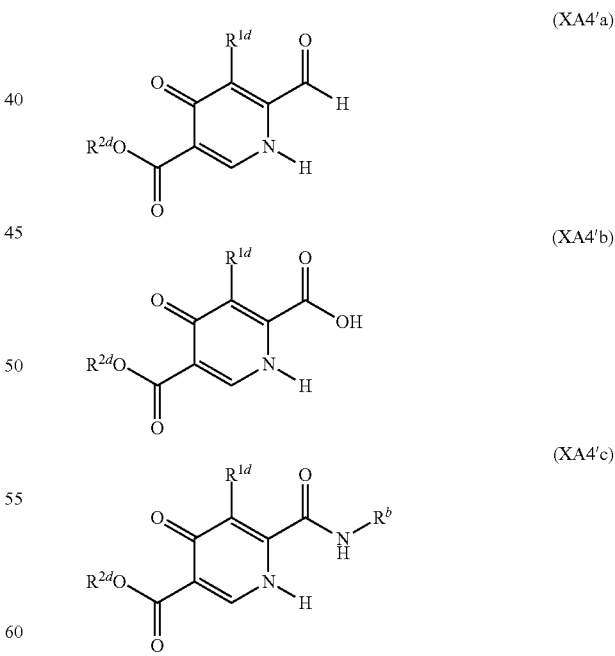

(wherein each symbol is defined in Item 1, and Item 3). When the formula (XA4'a) is reacted with the formula (V3'), the formula (XA4) in which $R^a$ is hydrogen is produced. When the formula (XA4'b) is reacted with the formula (V3'), the formula (XA4) in which $R^a$ is hydroxy is produced. When the formula (XA4'c) is reacted with the formula (V3'), the formula (XA4) in which $R^a$ is lower alkylamino optionally substituted by substituent E, lower alkenylamino optionally substituted by substituent E, lower alkynylamino optionally substituted by substituent E, carbocyclyl lower alkylamino optionally substituted by substituent E, or heterocyclyl lower alkylamino optionally substituted by substituent E is produced.

"An aldehyde group or a carboxyl group is formed by oxidative cleavage of an olefin site of formula (XA4'), or amide is formed by condensation reaction with a carboxyl group" is also the same as that of the case of the (XA3).

The production method according to the present invention will be described below.

(Step A)

The present step is a step of reacting Compound (X1) and Compound (V1) to obtain a solution containing Compound (X2), as shown in the following reaction formula.

Herein, the "solution" means a state where Compound (X2) is dissolved, and also includes one in a suspension state in which Compound (X2) is not completely dissolved, but is dispersed, and one in a slurry state. Hereinafter, the "solution" in the present specification all similarly includes one in the suspension state or the slurry state.

[Chemical formula 41]

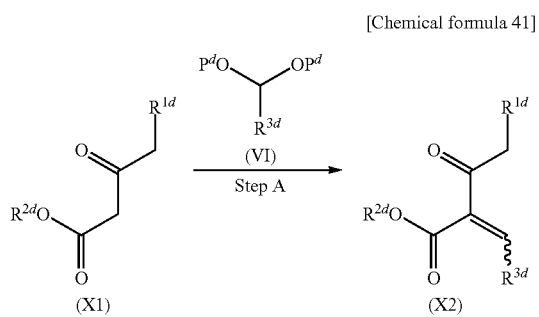

(wherein each symbol is defined above)

Compound (X1) is a commercially available reagent, or can be obtained by a known method.

When $R^{1d}$ is halogen, Compound (X1) in which $R^{1d}$ is lower alkyloxy optionally substituted by substituent E, carbocyclyl lower alkyloxy optionally substituted by substituent E, heterocyclyl lower alkyloxy optionally substituted by substituent E, or —OSi$(R^{1e})_3$ can be also obtained by adding an alcohol reagent such as a lower alcohol optionally substituted by substituent E, carbocyclyl lower alkyl alcohol optionally substituted by substituent E, heterocyclyl lower alkyl alcohol optionally substituted by substituent E, or $(R^{1e})_3$Si—OH, and performing a nucleophilic replacement reaction optionally in the presence of a base, in a solvent.

Examples of the "lower alkyloxy optionally substituted by substituent E" in $R^{1d}$ include methoxy, ethoxy, isopropoxy, trichloromethoxy and trifluoromethoxy. Preferable is methoxy.

Examples of the "carbocyclyl lower alkyloxy optionally substituted by substituent E" in $R^{1d}$ include benzyloxy, phenethyloxy, 2,4-trifluorobenzyloxy and 4-methoxybenzyloxy. Preferable is benzyloxy.

Example of the "heterocyclyl lower alkyloxy optionally substituted by substituent E" in $R^{1d}$ include pyridylmethyloxy.

A preferable aspect of $R^{1d}$ is hydrogen, chloro, bromo, methoxy, benzyloxy or the like.

Examples of the "lower alkyl optionally substituted by substituent E" in $R^{2d}$ include methyl, ethyl, n-propyl, isopropyl and tert-butyl.

Examples of the "carbocyclyl lower alkyl optionally substituted by substituent E" in $R^{2d}$ include benzyl and 4-methoxybenzyl.

Examples of the "heterocyclyl lower alkyl optionally substituted by substituent E" in $R^{2d}$ include pyridylmethyl.

A preferable aspect of $R^{2d}$ is methyl, ethyl, n-propyl, isopropyl, tert-butyl, benzyl or the like.

A preferable aspect of $R^{1e}$ is methyl, ethyl, n-propyl, isopropyl, tert-butyl or the like.

As a reaction solvent of the nucleophilic replacement reaction for obtaining (X1), an aprotic solvent is preferable. Examples thereof include acetonitrile, tetrahydrofuran, dioxane, diethyl ether, dichloromethane, chloroform, toluene, xylene, ethyl acetate, N,N-dimethylformamide, N,N-dimethylacetamide and dimethylimidazolidinone.

The aforementioned base may be a base which can deprotonate an alcohol reagent, and examples thereof include n-butyllithium, tert-butyllithium, sodium-tert-butoxide, potassium-tert-butoxide, sodium-tert-pentoxide, sodium methoxide, sodium ethoxide, sodium hydride, lithium diisopropylamide and lithium bistrimethylsilylamide.

An amount of the base is about 1.0 to 3.0 molar equivalents relative to Compound (X1) in which $R^{1d}$ is halogen.

An amount of the alcohol reagent is about 0.5 to 1.5 molar equivalents relative to Compound (X1) in which $R^{1d}$ is halogen.

A reaction temperature is usually 0° C. to a refluxing temperature, preferably room temperature to 50° C.

A reaction time is usually 10 minutes to 50 hours, preferably 1 to 4 hours.

Compound (V1) can be obtained as a commercially available reagent, or can be obtained by a known method.

Examples of the "lower alkyl optionally substituted by substituent E" in $P^d$ include methyl, ethyl and trifluoromethyl. A preferable aspect of Pd is methyl.

Examples of the "lower alkyl optionally substituted by substituent E" in $R^{3d}$ include methyl, ethyl and trifluoromethyl.

Examples of the "lower alkyl optionally substituted by substituent E" in $R^{3e}$ include methyl, ethyl and trifluoromethyl.

A preferable aspect of $R^{3d}$ is —N(CH$_3$)$_2$, —OCH$_3$, pyrrolidinyl or the like.

Examples of a reaction solvent of a reaction for obtaining Compound (X2) by reacting Compound (X1) and Compound (V1) include acetonitrile, tetrahydrofuran, dioxane, diethyl ether, dichloromethane, chloroform, toluene, xylene, ethyl acetate, N,N-dimethylformamide, N,N-dimethylacetamide and dimethylimidazolidinone.

An amount of Compound (V1) used is about 1.0 to 3.0 molar equivalents relative to Compound (X1), or Compound (V1) may be used as a solvent.

A reaction temperature is usually 0° C. to a refluxing temperature, preferably room temperature.

A reaction time is usually 30 minutes to 50 hours, preferably 2 to 8 hours.

By the present step, a solution containing Compound (X2) is obtained. Compound (X2) may be isolated by a general purification method (extraction, distillation, column chromatography, crystallization etc.), or may be used in a next reaction without isolation.

(Step A')
Alternatively, Compound (X2) can be also obtained by the following reaction.

[Chemical formula 42]

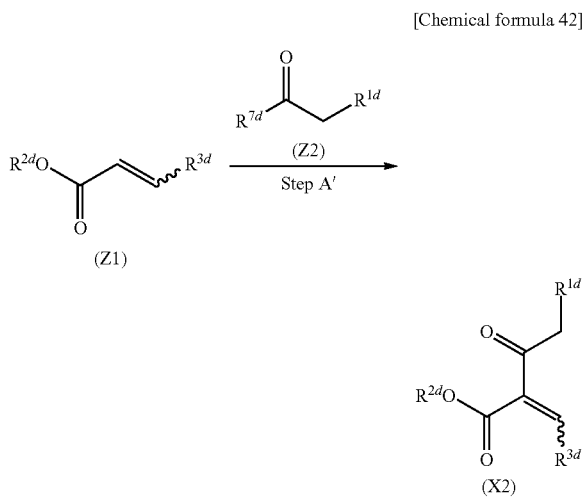

(wherein $R^{7d}$ is halogen, lower alkyloxy optionally substituted by substituent E or —O—SO$_2$—R$^{5e}$, and other each symbol is defined above)

Compound (Z1) is a commercially available reagent, or can be obtained by a known method.

Examples of the "lower alkyl optionally substituted by substituent E" in $R^{2d}$ include methyl, ethyl, n-propyl, isopropyl and tert-butyl.

Examples of the "carbocyclyl lower alkyl optionally substituted by substituent E" in $R^{2d}$ include benzyl and 4-methoxybenzyl.

Examples of the "heterocyclyl lower alkyl optionally substituted by substituent E" in $R^{2d}$ include pyridylmethyl.

A preferable aspect of $R^{2d}$ is methyl, ethyl, n-propyl, isopropyl, tert-butyl, benzyl or the like.

Examples of the "lower alkyl optionally substituted by substituent E" in $R^{3d}$ include methyl, ethyl and trifluoromethyl.

Examples of the "lower alkyl optionally substituted by substituent E" in $R^{3e}$ include methyl, ethyl and trifluoromethyl.

A preferable aspect of $R^{3d}$ is —N(CH$_3$)$_2$, —OCH$_3$, pyrrolidinyl or the like.

Examples of the "lower alkyloxy optionally substituted by substituent E" in $R^{1d}$ include methoxy, ethoxy, isopropoxy, trichloromethoxy and trifluoromethoxy. Preferable is methoxy.

Examples of the "carbocyclyl lower alkyloxy optionally substituted by substituent E" in $R^{1d}$ include benzyloxy, phenethyloxy, 2,4-trifluorobenzyloxy and 4-methoxybenzyloxy. Preferable is benzyloxy.

Example of the "heterocyclyl lower alkyloxy optionally substituted by substituent E" in $R^{1d}$ include pyridylmethyloxy.

A preferable aspect of $R^{1d}$ is hydrogen, chloro, bromo, methoxy, benzyloxy or the like.

Compound (Z1) is a commercially available reagent, or can be obtained by a known method Examples of a preferable aspect of $R^{7d}$ include chloro, bromo, methoxy, ethoxy, acetoxy, methanesulfonyloxy, trifluoromethanesulfonyloxy and paratoluenesulfonyloxy.

Examples of a reaction solvent of a reaction for obtaining Compound (X2) by reacting Compound (Z1) and Compound (Z2) include acetonitrile, tetrahydrofuran, dioxane, diethyl ether, dichloromethane, chloroform, toluene, xylene, ethyl acetate, N,N-dimethylformamide, N,N-dimethylacetamide and dimethylimidazolidinone.

An amount of Compound (Z2) used is about 1.0 to 3.0 molar equivalents relative to Compound (Z1).

A reaction temperature is usually −10° C. to a refluxing temperature, preferably room temperature.

A reaction time is usually 10 minutes to 10 hours, preferably 1 to 4 hours.

If necessary, a tertiary amine is added. Examples of the tertiary amine include pyridine, triethylamine, dimethylaminopyridine and N-methylmorpholine.

By the present step, a solution containing Compound (X2) is obtained. Compound (X2) may be isolated by a general purification method (extraction, distillation, column chromatography, crystallization etc.), or may be used in a next reaction without isolation.

(Step B)

The present step is a step of obtaining a solution containing Compound (X3), by reacting Compound (X2) and Compound (V2) optionally in the presence of a base, as shown in the following reaction formula.

[Chemical formula 43]

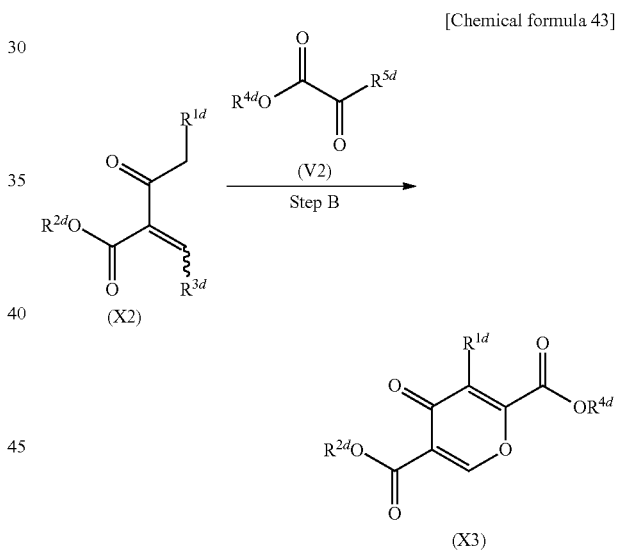

(wherein each symbol is defined above)

Examples of the "lower alkyloxy optionally substituted by substituent E" in $R^{1d}$ include methoxy, ethoxy, isopropoxy, trichloromethoxy and trifluoromethoxy. Preferable is methoxy.

Examples of the "carbocyclyl lower alkyloxy optionally substituted by substituent E" in $R^{1d}$ include benzyloxy, phenethyloxy, 2,4-trifluorobenzyloxy and 4-methoxybenzyloxy. Preferable is benzyloxy.

Example of the "heterocyclyl lower alkyloxy optionally substituted by substituent E" in $R^{1d}$ include pyridylmethyloxy.

A preferable aspect of $R^{1d}$ is hydrogen, chloro, bromo, methoxy, benzyloxy or the like.

Examples of the "lower alkyl optionally substituted by substituent E" in $R^{2d}$ include methyl, ethyl, n-propyl, isopropyl and tert-butyl.

Examples of the "carbocyclyl lower alkyl optionally substituted by substituent E" in $R^{2d}$ include benzyl and 4-methoxybenzyl.

Examples of the "heterocyclyl lower alkyl optionally substituted by substituent E" in $R^{2d}$ include pyridylmethyl.

A preferable aspect of $R^{2d}$ is methyl, ethyl, n-propyl, isopropyl, tert-butyl or the like.

Examples of the "lower alkyl optionally substituted by substituent E" in $R^{3d}$ include methyl, ethyl and trifluoromethyl.

Examples of the "lower alkyl optionally substituted by substituent E" in $R^{3e}$ include methyl, ethyl and trifluoromethyl.

A preferable aspect of $R^{3d}$ is —N(CH$_3$)$_2$, —OCH$_3$, pyrrolidinyl or the like.

Compound (V2) can be obtained as a commercially available reagent, or can be obtained by a known method.

Examples of the "lower alkyl optionally substituted by substituent E" in $R^{4d}$ include methyl, ethyl, n-propyl, isopropyl and tert-butyl.

Examples of the "carbocyclyl lower alkyl optionally substituted by substituent E" in $R^{4d}$ include benzyl and 4-methoxybenzyl.

Examples of the "heterocyclyl lower alkyl optionally substituted by substituent E" in $R^{4d}$ include pyridylmethyl.

Examples of a preferable aspect of $R^{4d}$ include methyl, ethyl, n-propyl, iso-propyl, tert-butyl, benzyl and 4-methoxybenzyl.

Examples of a preferable aspect of $R^{5d}$ include chloro, bromo, methoxy, ethoxy, acetoxy, methanesulfonyloxy, trifluoromethanesulfonyloxy and paratoluenesulfonyloxy. Particularly, chloro, methoxy and ethoxy are preferable.

Examples of a reaction solvent include acetonitrile, tetrahydrofuran, dioxane, toluene, xylene, ethyl acetate, N,N-dimethylformamide, N,N-dimethylacetamide, dimethylimidazolidinone, N-methylmorpholine and N-methylpyrrolidinone.

Examples of the base include n-butyllithium, tert-butyllithium, sodium-tert-butoxide, potassium-tert-butoxide, sodium-tert-pentoxide, sodium methoxide, sodium ethoxide, sodium hydride, lithium diisopropylamide and lithium bistrimethylsilylamide.

An amount of the base used is about 1.0 to 5.0 molar equivalents relative to Compound (X2).

An amount of Compound (V2) used is about 1.5 to 5.0 molar equivalents relative to Compound (X2), or Compound (V2) may be used as a solvent.

A reaction temperature is usually −80° C. to a refluxing temperature, preferably −20° C. to 50° C.

A reaction time is usually 30 minutes to 50 hours, preferably 2 to 12 hours.

By the present step, a solution containing Compound (X3) is obtained. Compound (X3) may be isolated by a general purification method (extraction, distillation, column chromatography, crystallization etc.), or may be used in a next reaction without isolation. Preferably, the compound is isolated as a crystal from which impurities have been removed by crystallization.

(Step B-II)

The present step is a step of obtaining a solution containing Compound (XA3) by reacting Compound (X2) and Compound (VA2) optionally in the presence of a base, as shown in the following reaction formula.

[Chemical formula 44]

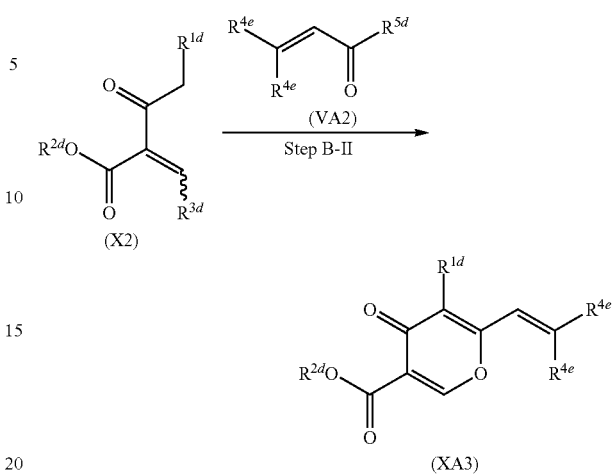

(wherein each symbol is defined above)

Examples and preferable aspects of $R^{1d}$, $R^{2d}$, $R^{3d}$ and $R^{5d}$ in the formulas (X2) and (VA2) are the same as those defined above, respectively.

Compound (VA2) can be obtained as a commercially available reagent, or by a known method.

Examples of the "lower alkyl optionally substituted by substituent E" of $R^{4e}$ include methyl and ethyl.

Examples of the "carbocyclyl optionally substituted by substituent E" of $R^{4e}$ include phenyl and cyclohexyl.

Examples of the "heterocyclyl optionally substituted by substituent E" of $R^{4e}$ include pyridyl and piperazyl.

$R^{4e}$ is preferably such that one is hydrogen, and the other is phenyl.

Examples of a reaction solvent include acetonitrile, tetrahydrofuran, dioxane, toluene, xylene, ethyl acetate, N,N-dimethylformamide, N,N-dimethylacetamide, dimethylimidazolidinone, N-methylmorpholine and N-methylpyrrolidinone.

Examples of the base include n-butyllithium, tert-butyllithium, sodium-tert-butoxide, potassium-tert-butoxide, sodium-tert-pentoxide, sodium methoxide, sodium ethoxide, sodium hydride, lithium diisopropylamide and lithium bistrimethylsilylamide.

An amount of the base used is about 1.0 to 5.0 molar equivalents relative to Compound (XA2).

An amount of Compound (VA2) used is about 1.0 to 2.0 molar equivalents relative to Compound (X2).

A reaction temperature is usually −80° C. to 20° C., preferably −80° C. to −40° C.

A reaction time is usually 5 minutes to 6 hours, preferably 15 minutes to 2 hours.

By the present step, a solution containing Compound (XA3) is obtained. Compound (XA3) may be isolated by a general purification method (extraction, distillation, column chromatography, crystallization etc.), or may be used in a next reaction without isolation. Preferably, the compound is isolated as a crystal from which impurities have been removed by crystallization.

(Step C)

The present step is a step of obtaining Compound (X4) by reacting Compound (X3) and Compound (V3), as shown in the following reaction formula.

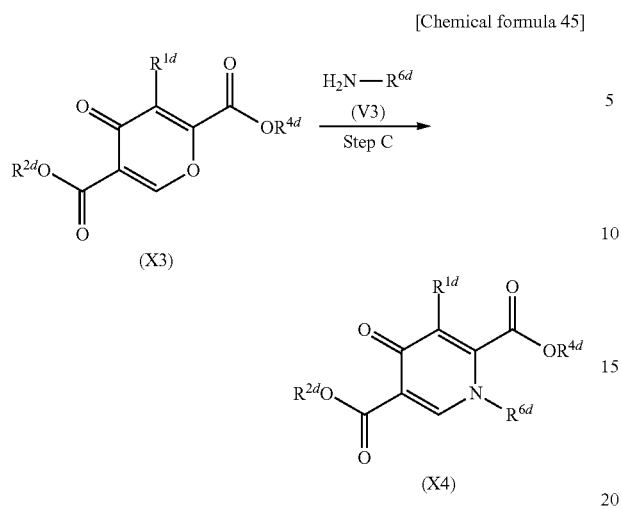

(wherein each symbol is defined above)

Examples of the "lower alkyloxy optionally substituted by substituent E" in $R^{1d}$ include methoxy, ethoxy, isopropoxy, trichloromethoxy and trifluoromethoxy. Preferable is methoxy.

Examples of the "carbocyclyl lower alkyloxy optionally substituted by substituent E" in $R^{1d}$ include benzyloxy, phenethyloxy, 2,4-trifluorobenzyloxy and 4-methoxybenzyloxy. Preferable is benzyloxy.

Example of the "heterocyclyl lower alkyloxy optionally substituted by substituent E" in $R^{1d}$ include pyridylmethyloxy.

A preferable aspect of $R^{1d}$ is hydrogen, chloro, bromo, methoxy, benzyloxy or the like.

Examples of the "lower alkyl optionally substituted by substituent E" in $R^{2d}$ include methyl, ethyl, n-propyl, isopropyl and tert-butyl.

Examples of the "carbocyclyl lower alkyl optionally substituted by substituent E" in $R^{2d}$ include benzyl and 4-methoxybenzyl.

Examples of the "heterocyclyl lower alkyl optionally substituted by substituent E" in $R^{2d}$ include pyridylmethyl.

A preferable aspect of $R^{2d}$ is methyl, ethyl, n-propyl, isopropyl, tert-butyl or the like.

Examples of the "lower alkyl optionally substituted by substituent E" in $R^{4d}$ include methyl, ethyl, n-propyl, isopropyl and tert-butyl.

Examples of the "carbocyclyl lower alkyl optionally substituted by substituent E" in $R^{4d}$ include benzyl and 4-methoxybenzyl.

Examples of the "heterocyclyl lower alkyl optionally substituted by substituent E" in $R^{4d}$ include pyridylmethyl.

Examples of a preferable aspect of $R^{4d}$ include methyl, ethyl, n-propyl, iso-propyl, tert-butyl, benzyl and 4-methoxybenzyl.

Compound (V3) can be obtained as a commercially available reagent, or can be obtained by a known method.

Examples of the "lower alkyl optionally substituted by substituent E" in $R^{6d}$ include $HC(=O)-CH_2-$, $CH(-OH)_2-CH_2-$, $MeO-CH(-OH)-CH_2-$, dimethoxyethyl, diethoxyethyl, $CH_2=CH-CH_2-$, $HO-CH_2-CH(-OH)-CH_2-$,

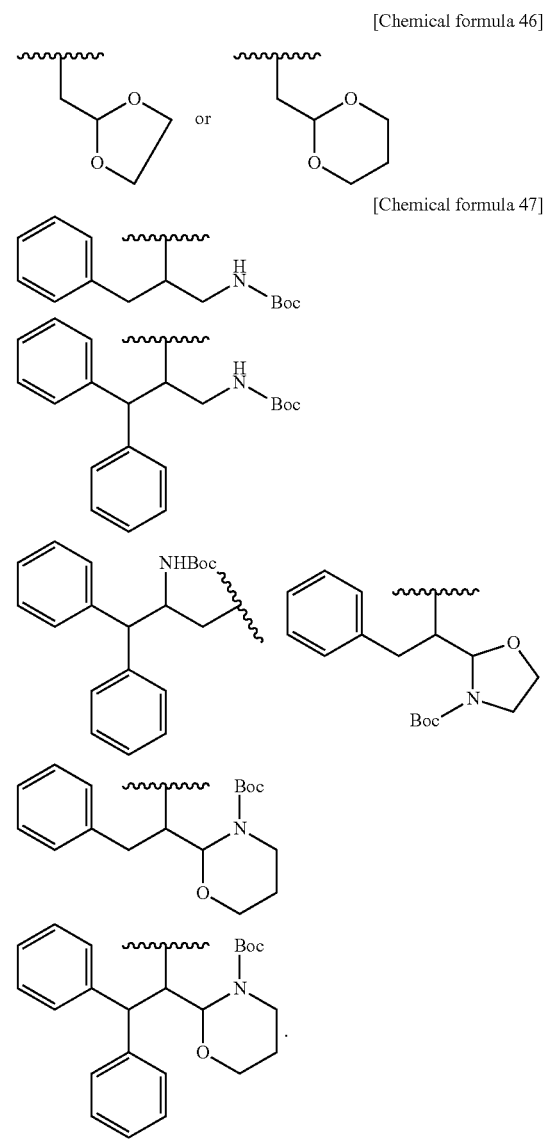

Examples of the "amino optionally substituted by substituent E" in $R^{6d}$ include methylamino, ethylamino, benzyloxycarbonylamino and tert-butoxycarbonylamino.

Examples of the "carbocyclyl optionally substituted by substituent E" in $R^{6d}$ include:

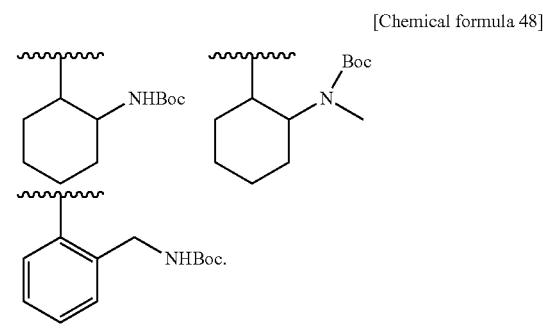

Examples of the "heterocyclyl optionally substituted by substituent E" in $R^{6d}$ include:

[Chemical formula 49]

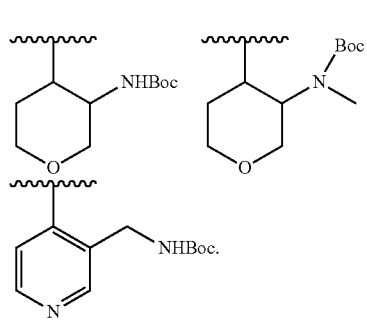

Examples of a reaction solvent include acetonitrile, tetrahydrofuran, dioxane, toluene, xylene, ethyl acetate, N,N-dimethylformamide, N,N-dimethylacetamide, dimethylimidazolidinone, N-methylmorpholine, N-methylpyrrolidinone, methanol, ethanol and isopropanol.

An amount of Compound (V3) used is about 1.0 to 2.0 molar equivalents relative to Compound (X3).

A reaction temperature is usually 0° C. to a refluxing temperature, preferably 20° C. to 70° C.

A reaction time is usually 30 minutes to 50 hours, preferably 2 to 12 hours.

When $R^{6d}$ of Compound (X4) produced is not a group having an aldehyde group such as $HC(=O)-CH_2-$, $MeO-CH(-OH)-CH_2-$ or $CH(-OH_2)-CH_2-$ or the equivalent thereof, the group can be derivatized into such as $HC(=O)-CH_2-$, $MeO-CH(-OH)-CH_2-$ or $CH(-OH)_2-CH_2-$, which is a group having an aldehyde group or the equivalent thereof, by a method of deprotecting a protective group for an aldehyde group described in Protective Groups in Organic Synthesis, Theodora W Green (John Wiley & Sons), or a known method shown in International Publication No. 2006/116764 pamphlet, or International Publication No. 2006/088173 pamphlet.

For examples, when $R^{6d}$ of Compound (X4) is dimethoxyethyl, it can be derivatized into $HC(=O)-CH_2-$ by adding an acid to a solution containing Compound (X4). The acid is not particularly limited, and examples thereof include hydrochloric acid, hydrobromic acid, sulfuric acid, nitric acid, phosphoric acid, p-toluenesulfonic acid, methanesulfonic acid, formic acid, acetic acid, trifluoroacetic acid, maleic acid and oxalic acid.

An amount of the acid used is 2.0 to 10.0 molar equivalents relative to Compound (X4). Acetic acid or formic acid may be used as a solvent, or may be used by mixing with the aforementioned acid.

A reaction temperature is usually about 0° C. to 80° C., preferably 10° C. to 40° C.

A reaction time is usually 30 minutes to 50 hours, preferably 2 to 12 hours.

When an amino group is protected with an amino protective group, a deprotected compound can be obtained by a method of deprotecting a protective group for an amino group described in Protective Groups in Organic Synthesis, Theodora W Green (John Wiley and Sons) or a known method. An order of performing a deprotecting reaction can be arbitrarily changed.

By the present step, a solution containing Compound (X4) is obtained. Compound (X4) may be isolated by a general purification method (extraction, distillation, column chromatography, crystallization etc.), or may be used in a next reaction without isolation. Preferably, the compound is isolated as a crystal from which impurities have been removed by crystallization.

(Step C-II)

The present step is a step of obtaining a solution containing Compound (XA4) by reacting Compound (XA3) and Compound (V3) optionally in the presence of a base, as shown in the following reaction formula.

[Chemical formula 50]

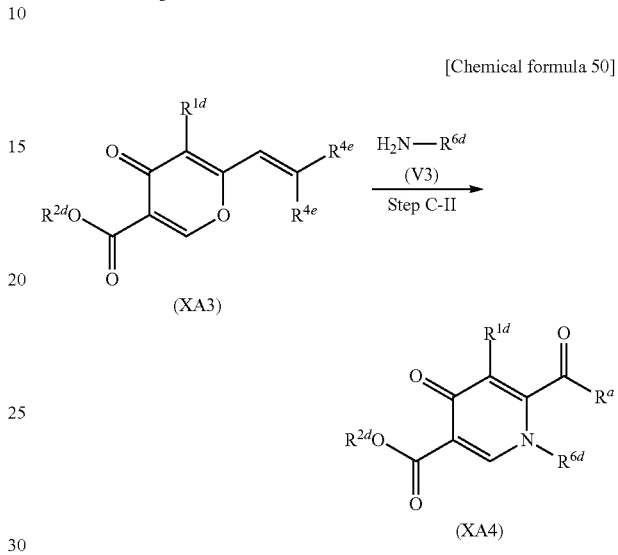

(wherein each symbol is defined above)

Examples and preferable aspects of $R^{1d}$, $R^{2e}$ and $R^{4e}$ in the formulas (XA3) and (VA4) are the same as those defined above, respectively.

Examples of the "lower alkylamino optionally substituted by substituent E" of $R^a$ in the formula (XA4) include methylamino, ethylamino, isopropylamino, tert-butylamino, methoxymethylamino, methoxyethylamino, ethoxyethylamino, methoxypropylamino, hydroxyethylamino, piperazinylcarbonylethylamino, morpholinylcarbonylethylamino, methylaminoethylamino, methylsulfonylethylamino, tert-butylcarbonylaminoethylamino, isopropyloxycarbonylaminoethylamino, methylcarbonylaminoethylamino, aminoethylamino and tert-butyloxycarbonylaminoethylamino.

Examples of the "lower alkenylamino optionally substituted by substituent E" of $R^a$ include ethylenylamino and propenylamino.

Examples of the "lower alkynylamino optionally substituted by substituent E" of $R^a$ include propynylamino.

Examples of the "carbocyclyl lower alkylamino optionally substituted by substituent E" of $R^a$ include benzylamino, difluorobenzylamino, chlorofluorobenzylamino, cyclopropylmethylamino, 4-fluorobenzylamino, cyclohexylmethylenylamino, cyclopropylamino, ethyloxycarbonylethylamino, carboxyethylamino, dimethylaminocarbonyl, 4-methoxybenzylamino and 4-methylbenzylamino.

Examples of the "heterocyclyl lower alkylamino optionally substituted by substituent E" of $R^a$ include pyridylmethylamino, tetrahydropyranylmethylenylamino and methylisoxazolylmethylenylamino.

Examples of the "lower alkyl optionally substituted by substituent E" in $R^{6d}$ include $HC(=O)-CH_2-$, $CH(-OH)_2-CH_2-$, $MeO-CH(-OH)-CH_2-$, dimethoxymethyl, diethoxyethyl, $CH_2=CH-CH_2-$, $HO-CH_2-CH(-OH)-CH_2-$,

[Chemical formula 51]

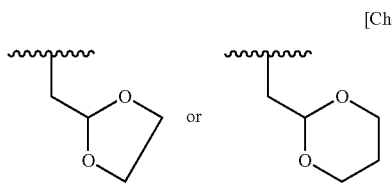

or, when $R^a$ is hydroxy, examples of $R^{6d}$ include:

[Chemical formula 52]

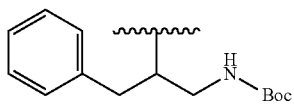

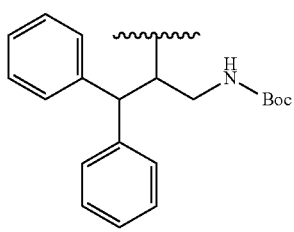

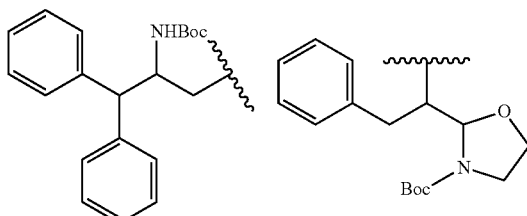

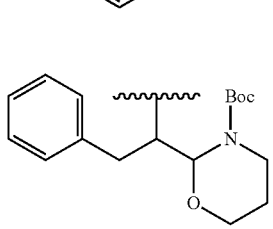

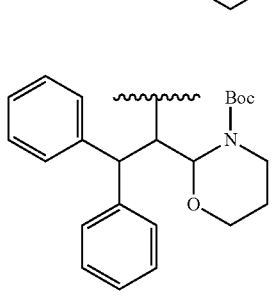

or when $R^a$ is the "lower alkylamino optionally substituted by substituent E", the "lower alkenylamino optionally substituted by substituent E", the "lower alkynylamino optionally substituted by substituent E", the "carbocyclyl lower alkylamino optionally substituted by substituent E", or the "heterocyclyl lower alkylamino optionally substituted by substituent E", examples of $R^{6d}$ include:

[Chemical formula 53]

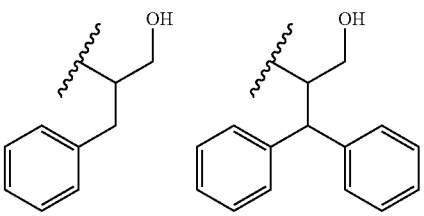

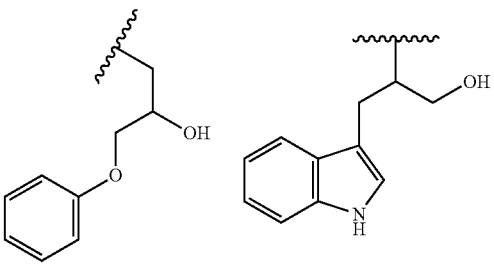

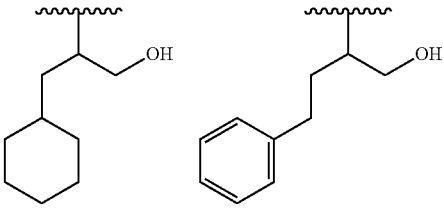

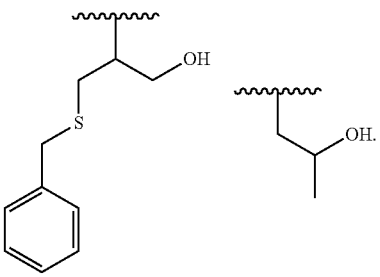

Examples of the "amino optionally substituted by substituent E" in $R^{6d}$ include methylamino, ethylamino, benzyloxycarbonylamino and tert-butoxycarbonylamino.

Examples of the "carbocyclyl optionally substituted by substituent E" in $R^{6d}$ include:

[Chemical formula 54]

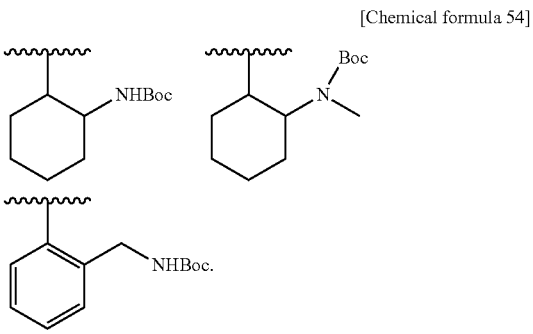

Examples of the "heterocyclyl optionally substituted by substituent E" in $R^{6d}$ include:

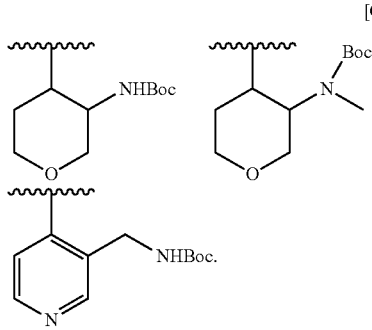
[Chemical formula 55]

Conversion from an olefin form ($-CH=C(R^{4e})_2$) to $-CO-R^a$, when $R^a$ is hydroxy, can be performed on aldehyde ($R^a$ is hydrogen) obtained under generally known oxidation reaction condition (e.g. ozone oxidation reaction, $RuCl_3-NaIO_4$ oxidation reaction etc.), under subsequent general oxidation reaction condition (e.g. $Cr_3$-pyridine, PCC oxidation, $SO_3$-pyridine oxidation, $NaClO_2$ oxidation etc.).

When $R^a$ is the "lower alkylamino optionally substituted by substituent E", the "lower alkenylamino optionally substituted by substituent E", the "lower alkynylamino optionally substituted by substituent E", the "carbocyclyl lower alkylamino optionally substituted by substituent E", or the "heterocyclyl lower alkylamino optionally substituted by substituent E", the conversion can be performed on a carboxyl group ($R^a$ is hydroxy) by a general dehydration condensation reaction (Mitsunobu reaction, reactions using carboxylic acid halide, carboxylic anhydride, or a condensing agent (e.g. WSC, carbonyldiimidazole, dicyclohexylcarbodiimide)).

Examples of a reaction solvent include acetonitrile, tetrahydrofuran, dioxane, toluene, xylene, ethyl acetate, N,N-dimethylformamide, N,N-dimethylacetamide, dimethylimidazolidinone, N-methylmorpholine, N-methylpyrrolidinone, methanol, ethanol and isopropanol.

An amount of Compound (V3) used is about 1.0 to 3.0 molar equivalents relative to Compound (XA3).

A reaction temperature is usually 0° C. to a refluxing temperature, preferably 20° C. to 70° C.

A reaction time is usually 10 minutes to 50 hours, preferably 1 to 12 hours.

When $R^{6d}$ of Compound (X4) produced is not a group having an aldehyde group such as $HC(=O)-CH_2-$, $MeO-CH(-OH)-CH_2-$ or $CH(-OH)_2-CH_2-$, or the equivalent thereof, the group can be derivatized into such as $HC(=O)-CH_2-$, $MeO-CH(-OH)-CH_2-$ or $CH(-OH)^2-CH_2-$, which is a group having an aldehyde group or the equivalent thereof, by the aforementioned method.

When an amino group is protected with an amino protective group, a deprotected compound can be obtained by a method of deprotecting a protective group for an amino group described in Protective Groups in Organic Synthesis, Theodora W Green (John Wiley and Sons) or a known method. An order of performing a deprotecting reaction can be arbitrarily changed.

By the present step, a solution containing Compound (XA4) is obtained. Compound (XA4) may be isolated by a general purification method (extraction, distillation, column chromatography, crystallization etc.), or may be used in a next reaction without isolation. Preferably, the compound is isolated as a crystal from which impurities have been removed by crystallization.

(Step B')

The present step is a step of obtaining Compound (X4') by reacting Compound (X2) with Compound (V2) and Compound (V2') optionally in the presence of a base, as shown in following formula.

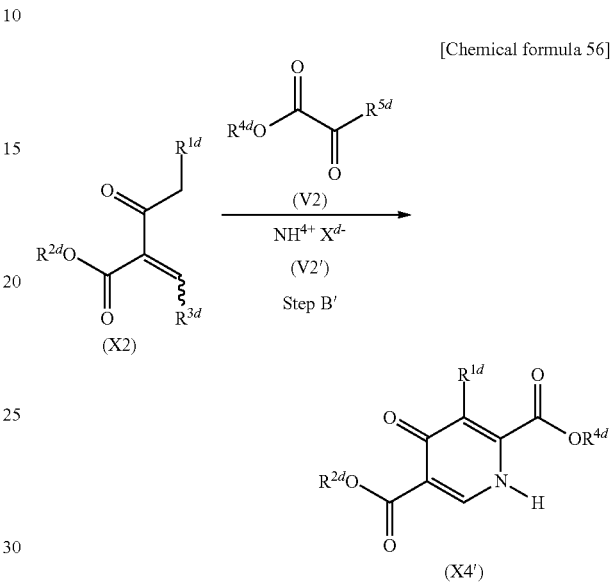
[Chemical formula 56]

(wherein each symbol is defined above)

Examples and preferable aspects of $R^{1d}$, $R^{2d}$, $R^{3d}$, $R^{4d}$ and $R^{5d}$ in the formulas (X2) and (V2) are the same as those described above, respectively.

Examples of a reaction solvent include acetonitrile, tetrahydrofuran, dioxane, toluene, xylene, ethyl acetate, N,N-dimethylformamide, N,N-dimethylacetamide, dimethylimidazolidinone, N-methylmorpholine and N-methylpyrrolidinone.

Examples of the base include n-butyllithium, tert-butyllithium, sodium-tert-butoxide, potassium-tert-butoxide, sodium-tert-pentoxide, sodium methoxide, sodium ethoxide, sodium hydride, lithium diisopropylamide and lithium bistrimethylsilylamide.

An amount of the base used is about 1.0 to 5.0 molar equivalents relative to Compound (X2).

An amount of Compound (V2) used is about 1.0 to 3.0 molar equivalents relative to Compound (X2), or Compound (V2) may be used as a solvent.

A reaction temperature is usually −80° C. to a refluxing temperature, preferably −20° C. to 30° C.

A reaction time is usually 10 minutes to 10 hours, preferably 30 minutes to 4 hours.

Subsequently, Compound (V2') is added to the reaction solution to allow to react.

Examples of Compound (V2') include ammonium acetate, ammonium chloride, ammonium bromide, ammonium sulfate, ammonium hydrogen sulfate, ammonium formate, ammonium nitrate, ammonium hydroxide, ammonium phosphate, $NH_4^+BF_4^-$, $NH_4^+PF_6^-$, $NH_4^+Ph-S\ O_3^-$, $NH_4^+CH_3-Ph-S\ O_3^-$ and $NH_4^+CH_3-SO_3^-$. Preferable are ammonium acetate, ammonium chloride, ammonium sulfate, ammonium hydrogen sulfate and ammonium formate An amount of Compound (V2') used is about 1.0 to 3.0 molar equivalents relative to Compound (X2).

A reaction temperature is usually 0° C. to a refluxing temperature, preferably 20° C. to 80° C.

A reaction time is usually 10 minutes to 10 hours, preferably 30 minutes to 4 hours.

By the present step, a solution containing Compound (X4') is obtained. Compound (X4') may be isolated by a general purification method (extraction, distillation, column chromatography, crystallization etc.), or may be used in a next reaction without isolation. Preferably, the compound is isolated as a crystal from which impurities have been removed by crystallization.

(Step C')

The present step is a step of obtaining Compound (X4) by reacting Compound (X4') and Compound (V3') optionally in the presence of a base, as shown in following reaction formula.

[Chemical formula 57]

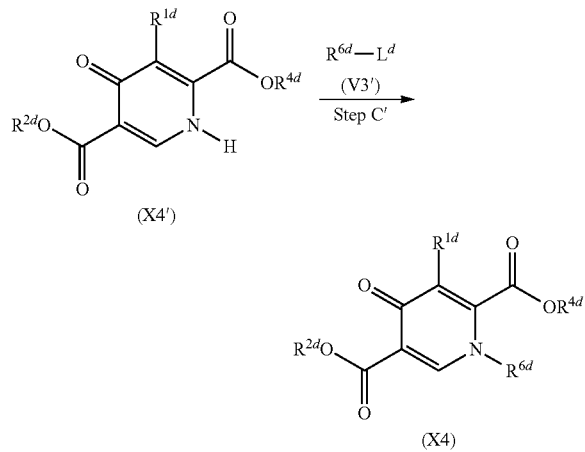

(wherein each symbol is defined above)

Examples and preferable aspects of $R^{1d}$, $R^{2d}$, $R^{4d}$ and $R^{6d}$ in the formulas (X4') and (V3') are the same as those defined above, respectively.

Examples of a "leaving group" in $L^d$ include halogen, —O—SO$_2$—CH$_3$, —O—SO$_2$—CF$_3$, —O—SO$_2$-Ph or —O—SO$_2$-Ph-C H$_3$. Preferable is halogen A method of derivatizing into an aldehyde group or the equivalent thereof when $R^{6d}$ of Compound (X4) produced does not have an aldehyde group such as HC(=O)—CH$_2$—, MeO—CH(—OH)—CH$_2$— or CH(—OH)$_2$—CH$_2$— or the equivalent thereof is the same as described above.

Examples of a reaction solvent include acetonitrile, ethyl acetate, N,N-dimethylformamide, N,N-dimethylacetamide, dimethylimidazolidinone, N-methylmorpholine and N-methylpyrrolidinone.

Examples of the base include potassium carbonate, cesium carbonate, sodium hydride, n-butyllithium, tert-butyllithium, sodium-tert-butoxide, potassium-tert-butoxide, sodium-tert-pentoxide, sodium methoxide, triethylamine, 4-dimethylaminopyridine, diisopropylethylamine and DBU (1,8-diazabicyclo[5.4.0]undec-7-ene).

An amount of the base used is about 1.0 to 5.0 molar equivalents relative to Compound (X4').

An amount of Compound (V3') used is about 1.0 to 4.0 molar equivalents relative to Compound (X4'), or Compound (V3') may be used as a solvent.

A reaction temperature is usually 0° C. to a refluxing temperature, preferably 20° C. to 80° C.

A reaction time is usually 30 minutes to 24 hours, preferably 1 to 8 hours.

By the present step, a solution containing Compound (X4) is obtained. Compound (X4) may be isolated by a general purification method (extraction, distillation, column chromatography, crystallization etc.), or may be used in a next reaction without isolation. Preferably, the compound is isolated as a crystal from which impurities have been removed by crystallization.

When $R^{6d}$ in Compound (X4) is —NH$_2$, Compound (X4) can be also obtained by reacting an O-(2,4-dinitrophenyl) hydroxylamine reagent with Compound (X4') optionally in the presence of a base.

Examples of a reaction solvent include N,N-dimethylformamide, N,N-dimethylacetamide, dimethylimidazolidinone, N-methylmorpholine and N-methylpyrrolidinone.

Examples of the base include potassium carbonate, cesium carbonate, sodium carbonate and lithium carbonate.

An amount of the base used is about 1.0 to 5.0 molar equivalents relative to Compound (X4').

An amounts of the reagent used is about 1.0 to 4.0 molar equivalents relative to Compound (X4').

A reaction temperature is usually 0° C. to a refluxing temperature, preferably 20° C. to 60° C.

A reaction time is usually 30 minutes to 24 hours, preferably 1 to 8 hours.

(Step D-1)

The present step is a step of obtaining Compound (I), when Compound (X4A) has the following structure.

[Chemical formula 58]

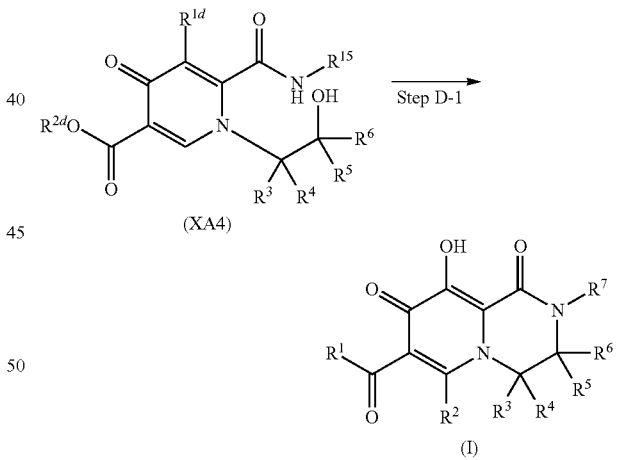

(wherein $R^{15}$ is an amino protective group, hydrogen, lower alkyl optionally substituted by substituent E, lower alkenyl optionally substituted by substituent E, lower alkynyl optionally substituted by substituent E, carbocyclyl lower alkyl optionally substituted by substituent E, or heterocyclyl lower alkyl optionally substituted by substituent E, and each symbol is defined above)

A closed ring form can be obtained by generating an intramolecular dehydration condensation reaction (e.g. Mitsunobu reaction) on an amido site (—CONH—$R^{15}$) and hydroxy group of Compound (XA4). When $R^{15}$ is an amino protective group, the intramolecular dehydration condensation reaction can be performed after the group is subjected to a known deprotecting reaction.

When $R^7$ is not hydrogen, by performing a known nucleophilic replacement reaction on an amino group, objective $R^7$ can be obtained.

When $R^{2d}$ is not hydrogen, a —COOR$^{2d}$ site can be derivatized into —COR$^1$ by performing a known reaction (ester hydrolysis reaction, deprotective reaction of carboxyl protective group, etc.) to convert $R^{2d}$ into hydrogen, and performing the known reaction (dehydration condensation reaction etc.) with carbocyclyl lower alkylamine optionally substituted by substituent E, lower alkylalcohol optionally substituted by substituent E etc. In addition, when $R^{2d}$ is a lower alkyl group such as a methyl group or an ethyl group, the site can be also directly derivatized into —COR$^1$ by an aminolysis reaction.

When $R^{1d}$ is lower alkyloxy optionally substituted by substituent E, carbocyclyl lower alkyloxy optionally substituted by substituent E, heterocyclyl lower alkyloxy optionally substituted by substituent E, or —OSi(R$^{1e}$)$_3$, it can be derivatized into a hydroxy group by subjecting to a known hydroxy deprotective reaction.

When $R^{1d}$ is halogen, it can be derivatized into a hydroxy group by reacting with potassium trimethylsilanolate or lithium trimethylsilanolate, and adding an aqueous solution of an inorganic acid. Alternatively, sodium hydride/water (Bioorganic Medicinal Chemistry Letters, 17, 1713, 2007), potassium hydroxide/tris(dibenzylideneacetone)dipalladium (Pd$_2$ dba$_3$)/di-tert-butylarylphosphine (Journal of the American Chemical Society, 128, 10694, 2006), potassium phosphate hydrate (K$_3$PO$_4$.H$_2$O)/tris(dibenzylideneacetone)dipalladium (Pd$_2$ dba$_3$)/tri-tert-butylphosphine (Tetrahedron Letters, 48, 473, 2007) are also exemplified as a reaction of converting halogen into a hydroxy group. As described above, when $R^{1d}$ of a raw material is halogen, since it becomes possible to be derivatized as it is, the number of reaction steps is deleted, and this can construct a more advantageous industrial production method, as compared with a method of carrying out a reaction of protecting and/or deprotecting an alcohol.

When $R^{1d}$ is hydrogen, it can be also derivatized into a hydroxy group by converting $R^{1d}$ into halogen by reacting with a halogenating agent such as N-bromosuccinimide, N-chlorosuccinimide, sulfuryl chloride etc., similarly reacting with potassium trimethylsilanolate or lithium trimethylsilanolate, and adding an aqueous solution of an inorganic acid. Therefore, depending on reactivity of reaction substrates, $R^{1d}$ can be appropriately selected.

In addition, in the above step, an order of an each reaction can be appropriately changed.

(Step D-2)

The present step is a step of obtaining Compound (II), when Compound (X4A) has the following structure.

[Chemical formula 59]

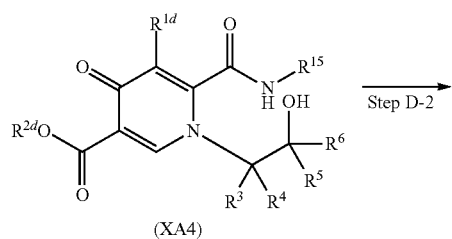

(XA4)

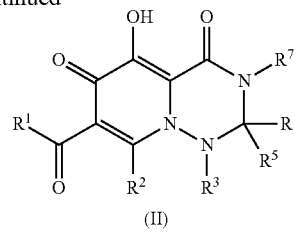

(II)

(wherein each symbol is defined above)

A closed ring form can be obtained by generating an intramolecular dehydration condensation reaction (e.g. Mitsunobu reaction) on an amido site (—CONH—R$^{15}$) and hydroxy group of Compound (XA4). When $R^{15}$ is an amino protective group, the intramolecular dehydration condensation reaction can be performed after the group is subjected to a known deprotecting reaction.

When $R^7$ is not hydrogen, by performing a known nucleophilic substitution reaction on an amino group, objective $R^7$ can be obtained.

When $R^{2d}$ is not hydrogen, a —COOR$^{2d}$ site can be derivatized into —COR$^1$ by performing a known reaction (ester hydrolysis reaction, deprotective reaction of carboxyl protective group, etc.) to convert $R^{2d}$ into hydrogen, and performing a known reaction (dehydration condensation reaction etc.) with carbocyclyl lower alkylamine optionally substituted by substituent E, lower alkylalcohol optionally substituted by substituent E etc. In addition, when $R^{2d}$ is a lower alkyl group such as a methyl group or an ethyl group, the site can be directly derivatized into —COR$^1$ by an aminolysis reaction.

When $R^{1d}$ is lower alkyloxy optionally substituted by substituent E, carbocyclyl lower alkyloxy optionally substituted by substituent E, heterocyclyl lower alkyloxy optionally substituted by substituent E, or —OSi(R$^{1e}$)$_3$, it can be derivatized into a hydroxy group by subjecting to a known hydroxy deprotective reaction.

When $R^{1d}$ is halogen, it can be derivatized into a hydroxy group by reacting with potassium trimethylsilanolate or lithium trimethylsilanolate, and adding an aqueous solution of an inorganic acid. Alternatively, sodium hydride/water (Bioorganic Medicinal Chemistry Letters, 17, 1713, 2007), potassium hydroxide/tris(dibenzylideneacetone)dipalladium (Pd$_2$ dba$_3$)/di-tert-butylarylphosphine (Journal of the American Chemical Society, 128, 10694, 2006), potassium phosphate hydrate (K$_3$PO4.H$_2$O)/tris(dibenzylideneacetone)dipalladium (Pd$_2$ dba$_3$)/tri-tert-butylphosphine (Tetrahedron Letters, 48, 473, 2007) are also exemplified as a reaction of converting halogen into a hydroxy group. As described above, when $R^{1d}$ of a raw material is halogen, since it becomes possible to be derivatized as it is, the number of reaction steps is deleted, and this can construct a more advantageous industrial production method, as compared with a method of performing a reaction of protecting and/or deprotecting an alcohol.

When $R^{1d}$ is hydrogen, it can be also derivatized into a hydroxy group by converting $R^{1d}$ into halogen by reacting a halogenating agent such as N-bromosuccinimide, N-chlorosuccinimide, sulfuryl chloride etc., similarly reacting with potassium trimethylsilanolate or lithium trimethylsilanolate, and adding an aqueous solution of an inorganic acid. Therefore, depending on reactivity of reaction substrates, $R^{1d}$ can be appropriately selected.

In addition, in the above step, an order of an each reaction can be appropriately changed.

(Step D-3)

The present step is a step of obtaining Compound (I), when Compound (X4A) has the following structure.

[Chemical formula 60]

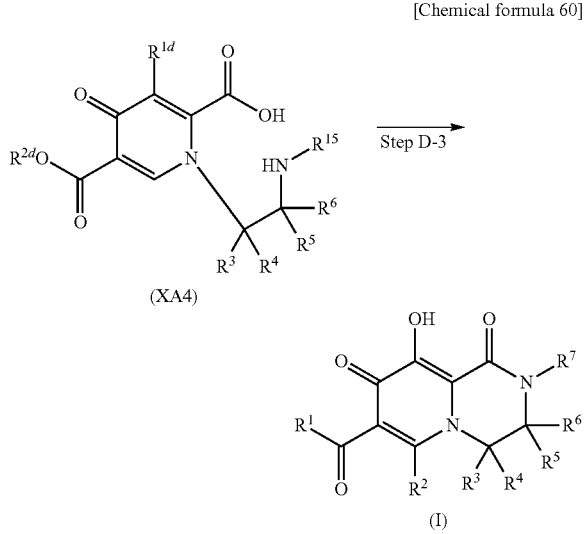

(wherein each symbol is defined above)

A closed ring form can be obtained by generating an intramolecular dehydration condensation reaction (e.g. Mitsunobu reaction, amidation reaction using a condensing agent etc.) on a carboxyl group (—COOH) and amino group of Compound (XA4). When $R^{15}$ is an amino protective group, the intramolecular dehydration condensation reaction can be preformed after the group is subjected to a known deprotecting reaction.

When $R^7$ is not hydrogen, by performing a known nucleophilic replacement reaction on an amino group, objective $R^7$ can be obtained.

When $R^{2d}$ is not hydrogen, a —COOR$^{2d}$ site can be derivatized into —COR$^1$ by performing a known reaction (ester hydrolysis reaction, deprotective reaction of carboxyl protective group, etc.) to convert $R^{2d}$ into hydrogen, and performing a known reaction (dehydration condensation reaction etc.) with carbocyclyl lower alkylamine optionally substituted by substituent E, lower alkylalcohol optionally substituted by substituent E etc. In addition, when $R^{2d}$ is a lower alkyl group such as a methyl group or an ethyl group, the site can be directly derivatized into —COR$^1$ by performing an aminolysis reaction.

When $R^{1d}$ is lower alkyloxy optionally substituted by substituent E, carbocyclyl lower alkyloxy optionally substituted by substituent E, heterocyclyl lower alkyloxy optionally substituted by substituent E, or —OSi($R^{1e}$)$_3$, it can be derivatized into a hydroxy group by subjecting to a known hydroxy deprotective reaction.

When $R^{1d}$ is halogen, it can be derivatized into a hydroxy group by reacting with potassium trimethylsilanolate or lithium trimethylsilanolate, and adding an aqueous solution of an inorganic acid. Alternatively, sodium hydride/water (Bioorganic Medicinal Chemistry Letters, 17, 1713, 2027), potassium hydroxide/tris(dibenzylideneacetone)dipalladium (Pd$_2$ dba$_3$)/di-tert-butylarylphosphine (Journal of the American Chemical Society, 128, 10694, 2006), potassium phosphate hydrate (K$_3$PO$_4$.H$_2$O)/tris(dibenzylideneacetone)dipalladium (Pd$_2$ dba$_3$)/tri-tert-butylphosphine (Tetrahedron Letters, 48, 473, 2007) are also exemplified as a reaction of converting halogen into a hydroxy group. Alternatively, when $R^{1d}$ of a raw material is halogen, since it becomes possible to be derivatized as it is, the number of reaction step is deleted, and this can construct a more advantageous industrial production method, as compared with a method of performing a reaction of protecting and/or deprotecting an alcohol.

When $R^{1d}$ is hydrogen, it can be also derivatized into a hydroxy group by converting $R^{1d}$ into halogen by reacting a halogenating agent such as N-bromosuccinimide, N-chlorosuccinimide, sulfuryl chloride etc., similarly reacting with potassium trimethylsilanolate or lithium trimethylsilanolate, and adding an aqueous solution of an inorganic acid. Therefore, depending on reactivity of reaction substrates, $R^{1d}$ can be appropriately selected.

In addition, in the above step, an order of an each reaction can be appropriately changed.

(Step D-4)

The present step is a step of obtaining Compound (II), when Compound (X4A) has the following structure.

[Chemical formula 61]

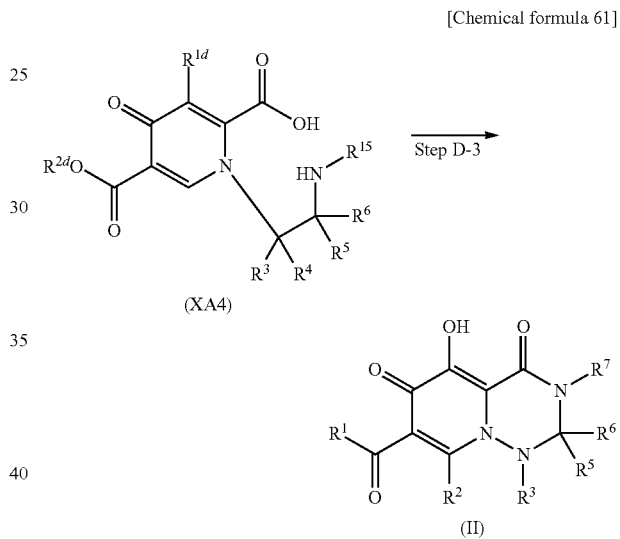

(wherein each symbol is defined above)

A closed ring form can be obtained by generating an intramolecular dehydration condensation reaction (e.g. Mitsunobu reaction, an amidation reaction using a condensing agent etc.) on a carboxyl group (—COOH) and amino group of Compound (XA4). When $R^{15}$ is an amino protective group, the intramolecular dehydration condensation reaction is performed after the group is subjected to a known deprotecting reaction.

When $R^7$ is not hydrogen, by performing a known nucleophilic replacement reaction on an amino group, objective $R^7$ can be obtained.

When $R^{2d}$ is not hydrogen, a —COOR$^{2d}$ site can be derivatized into —COR$^1$ by performing a known reaction (ester hydrolysis reaction, deprotective reaction of carboxyl protective group, etc.) to convert $R^{2d}$ into hydrogen, and performing a known reaction (dehydration condensation reaction etc.) with carbocyclyl lower alkylamine optionally substituted by substituent E, lower alkylalcohol optionally substituted by substituent E etc. In addition, when $R^{2d}$ is a lower alkyl group such as a methyl group or an ethyl group, the site can be also directly derivatized into —COR$^1$ by performing an aminolysis reaction.

When $R^{1d}$ is lower alkyloxy optionally substituted by substituent E, carbocyclyl lower alkyloxy optionally substituted by substituent E, heterocyclyl lower alkyloxy optionally substituted by substituent E, or —OSi(R$^{1e}$)$_3$, it can be derivatized into a hydroxy group by subjecting to a known hydroxy deprotective reaction.

When $R^{1d}$ is halogen, it can be derivatized into a hydroxy group by reacting with potassium trimethylsilanolate or lithium trimethylsilanolate, and adding an aqueous solution of an inorganic acid. Alternatively, sodium hydride/water (Bioorganic Medicinal Chemistry Letters, 17, 1713, 2007), potassium hydroxide/tris(dibenzylideneacetone)dipalladium (Pd$_2$ dba$_3$)/di-tert-butylarylphosphine (Journal of the American Chemical Society, 128, 10694, 2006), potassium phosphate hydrate (K$_3$PO$_4$.H$_2$O)/tris(dibenzylideneacetone)dipalladium (Pd$_2$ dba$_3$)/tri-tert-butylphosphine (Tetrahedron Letters, 48, 473, 2007) are also exemplified as a reaction of converting halogen into a hydroxy group. As described above, when $R^{1d}$ of a raw material is halogen, since it becomes possible to be derivatized as it is, the number of reaction step is deleted, and this can construct a more advantageous industrial production method, as compared with a method of performing a reaction of protecting and/or deprotecting an alcohol.

When $R^{1d}$ is hydrogen, it can be also derivatized into a hydroxy group by converting $R^{1d}$ into halogen by reacting a halogenating agent such as N-bromosuccinimide, N-chlorosuccinimide, sulfuryl chloride etc., similarly reacting with potassium trimethylsilanolate or lithium trimethylsilanolate, and adding an aqueous solution of an inorganic acid. Therefore, depending on reactivity of reaction substrates, $R^{1d}$ can be appropriately selected.

In addition, in the above step, an order of an each reaction can be appropriately changed.

(Step D-5)

The present step is a step of obtaining Compound (II), when Compound (XA4) has the following structure.

[Chemical formula 62]

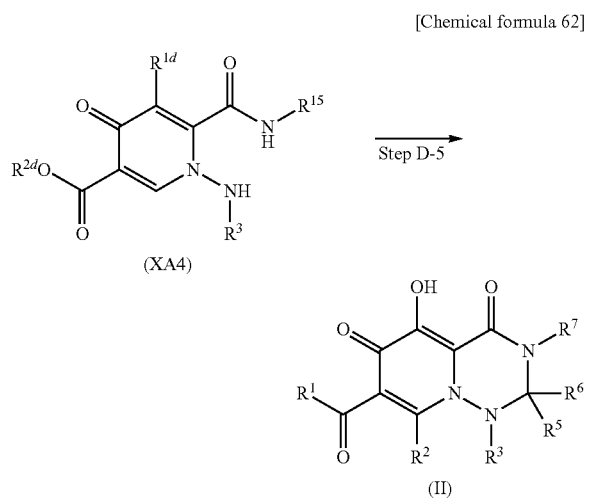

(wherein each symbol is defined above)

A closed ring form can be obtained by generating a condensation reaction of an amido site (—CONH—R$^{15}$) and amino group (—NH—R$^3$) of Compound (X4) with a compound having a carboxyl group (R$^5$—CO—R$^6$). Examples of the R$^5$—CO—R$^6$ include paraformaldehyde and, in this case, R$^5$ and R$^6$ are hydrogen. When the condensation reaction is performed, an acid is added, if necessary. Examples of the acid include acetic acid, formic acid and sulfuric acid.

When R$^{15}$ is an amino protective group, the condensation reaction can be performed after the group is subjected to a known deprotecting reaction.

When R$^7$ is not hydrogen, by performing a known nucleophilic replacement reaction on an amino group, objective R$^7$ can be obtained.

When R$^{2d}$ is not hydrogen, a —COOR$^{2d}$ site can be derivatized into —COR$^1$ by performing a known reaction (ester hydrolysis reaction, deprotective reaction of carboxyl protective group, etc.) to convert R$^{2d}$ into hydrogen, and performing a known reaction (dehydration condensation reaction etc.) with carbocyclyl lower alkylamine optionally substituted by substituent E, lower alkylalcohol optionally substituted by substituent E etc. In addition, when R$^{2d}$ is a lower alkyl group such as a methyl group or an ethyl group, the site can be also directly derivatized into —COR$^1$ by performing an aminolysis reaction.

When $R^{1d}$ is lower alkyloxy optionally substituted by substituent E, carbocyclyl lower alkyloxy optionally substituted by substituent E, heterocyclyl lower alkyloxy optionally substituted by substituent E, or —OSi(R$^{1e}$)$_3$, it can be derivatized into a hydroxy group by subjecting to a known hydroxy deprotective reaction.

When $R^{1d}$ is halogen, it can be derivatized into a hydroxy group by reacting with potassium trimethylsilanolate or lithium trimethylsilanolate, and adding an aqueous solution of an inorganic acid. Alternatively, sodium hydride/water (Bioorganic Medicinal Chemistry Letters, 17, 1713, 2007), potassium hydroxide/tris(dibenzylideneacetone)dipalladium (Pd$_2$ dba$_3$)/di-tert-butylarylphosphine (Journal of the American Chemical Society, 128, 10694, 2006), potassium phosphate hydrate (K$_3$PO$_4$.H$_2$O)/tris(dibenzylideneacetone)dipalladium (Pd$_2$ dba$_3$)/tri-tert-butylphosphine (Tetrahedron Letters, 48, 473, 2007) are also exemplified as a reaction of converting halogen into a hydroxy group. As described above, when $R^{1d}$ of a raw material is halogen, since it becomes possible to be derivatized as it is, the number of reaction step is deleted, and this can construct a more advantageous industrial production method, as compared with a method of performing a reaction of protecting and/or deprotecting an alcohol.

When $R^{1d}$ is hydrogen, it can be also derivatized into a hydroxy group by converting $R^{1d}$ into halogen by reacting a halogenating agent such as N-bromosuccinimide, N-chlorosuccinimide, sulfuryl chloride etc., similarly reacting with potassium trimethylsilanolate or lithium trimethylsilanolate, and adding an aqueous solution of an inorganic acid. Therefore, depending on reactivity of reaction substrates, $R^{1d}$ can be appropriately selected.

In addition, in the above step, an order of an each reaction can be appropriately changed.

(Step D-6)

The present step is a step of obtaining Compound (III), when Compound (X4) has the following structure.

[Chemical formula 63]

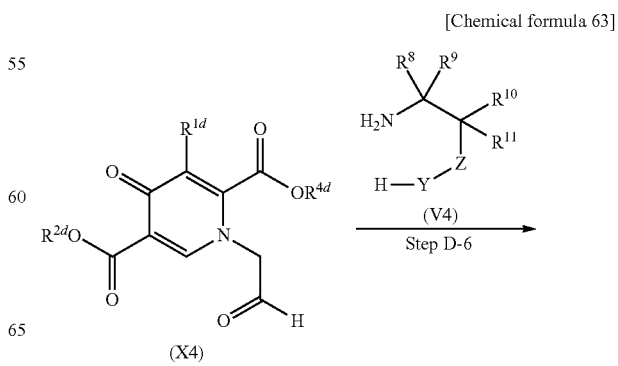

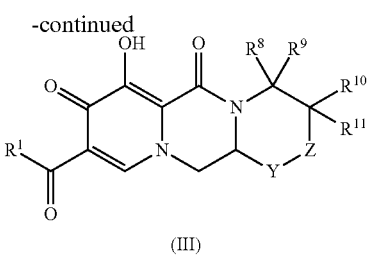

(III)

(wherein each symbol is defined above)

A tricyclic compound can be obtained by reacting an aldehyde site of Compound (X4) with an amino group and —Y—H of Compound (V4). When Z is a single bond, $R^{14}$ and $R^{10}$ may be taken together to form 4 to 8-membered heterocyclyl optionally substituted with substituent E and, in this case, Compound (III) becomes a tetracyclic compound.

Examples of Compound (V4) include 3-aminobutanol.

When $R^{2d}$ is not hydrogen, a —$COOR^{2d}$ site can be derivatized into —$COR^1$ by performing a known reaction (ester hydrolysis reaction, deprotective reaction of carboxyl protective group, etc.) to convert $R^{2d}$ into hydrogen, and performing a known reaction (dehydration condensation reaction etc.) with carbocyclyl lower alkylamine optionally substituted by substituent E, lower alkylalcohol optionally substituted by substituent E etc. In addition, when $R^{2d}$ is a lower alkyl group such as a methyl group or an ethyl group, the site can be also directly derivatized into —$COR^1$ by performing an aminolysis reaction.

When $R^{1d}$ is lower alkyloxy optionally substituted by substituent E, carbocyclyl lower alkyloxy optionally substituted by substituent E, heterocyclyl lower alkyloxy optionally substituted by substituent E, or —$OSi(R^{1e})_3$, it can be derivatized into a hydroxy group by subjecting to a known hydroxy deprotective reaction.

When $R^{1d}$ is halogen, it can be derivatized into a hydroxy group by reacting with potassium trimethylsilanolate or lithium trimethylsilanolate, and adding an aqueous solution of an inorganic acid. Alternatively, sodium hydride/water (Bioorganic Medicinal Chemistry Letters, 17, 1713, 2007), potassium hydroxide/tris(dibenzylideneacetone)dipalladium ($Pd_2 dba_3$)/di-tert-butylarylphosphine (Journal of the American Chemical Society, 128, 10694, 2006), potassium phosphate hydrate ($K_3PO_4.H_2O$)/tris(dibenzylideneacetone)dipalladium ($Pd_2 dba_3$)/tri-tert-butylphosphine (Tetrahedron Letters, 48, 473, 2007) are also exemplified as a reaction of converting halogen into a hydroxy group. As described above, when $R^{1d}$ of a raw material is halogen, since it becomes possible to be derivatized as it is, the number of reaction step is deleted, and this can construct a more advantageous industrial production method, as compared with a method of performing a reaction of protecting and/or deprotecting alcohol.

When $R^{1d}$ is hydrogen, it can be also derivatized into a hydroxy group by converting $R^{1d}$ into halogen by reacting a halogenating agent such as N-bromosuccinimide, N-chlorosuccinimide, sulfuryl chloride etc., similarly reacting with potassium trimethylsilanolate or lithium trimethylsilanolate, and adding an aqueous solution of an inorganic acid. Therefore, depending on reactivity of reaction substrates, $R^{1d}$ can be appropriately selected.

In addition, in the above step, an order of an each reaction can be appropriately changed.

The present invention will be described more detail hereinbelow by way of Examples and Test Examples of the present invention, but the present invention is not limited thereto. Respective symbols used in Examples have the following meanings.

DMF: N,N-dimethylformamide
DMA: N,N-dimethylacetamide
NMP: N-methylpyrrolidone
DMI: Dimethylimidazolidinone
THF: Tetrahydrofuran
MS: Methane sulfonyl
Ts: Paratoluenesulfonyl
Boc: Tert-butoxycarbonyl
DIBALH: Diisobutylaluminum hydride
WSC: N-ethyl-N'-(3-dimethylaminopropyl)carbodiimide
HOBt: 1-Hydroxybenzotriazole
HATU: O-(7-azabenzotriazol-1-yl)-N,N,N',N'-tetramethyluronium hexafluorophosphate
NBS; N-bromosuccinimide
NCS: N-chlorosuccinimide
TEMPO: 2,2,6,6-Tetramethylpiperidine-1-oxyl radical
PDC: Pyridinium dichloromate
DEAD: Diethyl azodicarboxylate
DIAD: Diisopropyl azodicarboxylate
DMAP: 4-Dimethylaminopyridine
mCPBA: M-chloroperbenzoic acid
DBU: 1,8-Diazabicyclo[5,4,0]-7-undecene The synthetic method of the present application will be shown below as Examples.

Example 1

[Chemical formula 64]

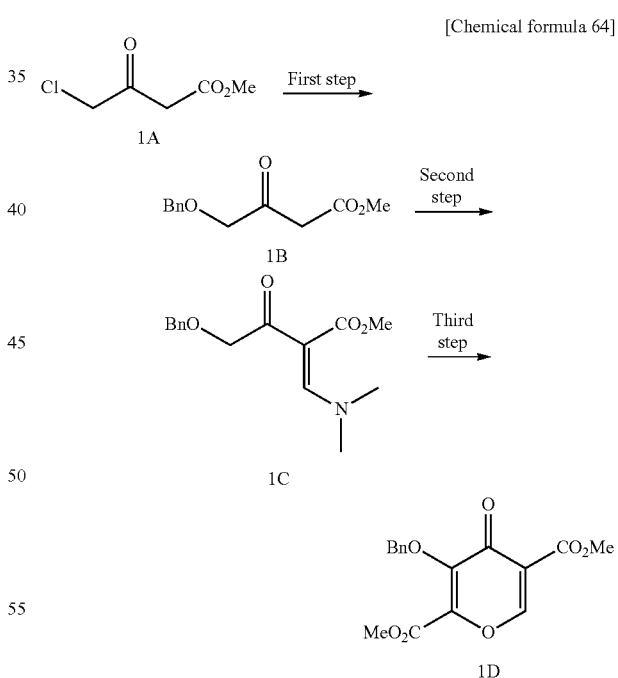

First Step

A solution of benzyl alcohol (1.00 g, 9.25 mmol) in THF (3 ml) was added to a suspension of sodium tert-pentoxide (2.55 g, 23.2 mmol) in THF (4 ml) at room temperature under a nitrogen atmosphere, and the mixture was stirred at 40° C. for 2 hours. This reaction solution was cooled in an ice bath, and a solution of Compound 1 A (1.53 g, 10.2 mmol) in THF (3 ml) was added dropwise at 0 to 10° C. After the reaction solution was stirred at room temperature for 2 hours, 2 N hydrochloric acid (15 ml) was added, followed by extraction with ethyl acetate two times. The combined extracts were washed sequentially with water, saturated sodium bicarbonate water, water and saturated sodium chloride water, and then dried with anhydrous sodium sulfate. The solvent was distilled off, and the resulting oil was purified by silica gel column chromatography (n-hexane-ethyl acetate 4:1, v/v) to obtain 1.89 g (yield 92%) of Compound 1B as an oil product.

$^1$H-NMR (CDCl$_3$) δ: 3.56 (2H, s), 3.71 (3H, s), 4.14 (2H, s), 4.59 (2H, s), 7.27-7.42 (5H, m).

Second Step

Compound 1B (1.80 g, 8.1 mmol) was dissolved in 1,4-dioxane (18 mL), N,N-dimethylformamide dimethyl acetal (1.45 g, 12.2 mmol) was added, and the mixture was stirred at room temperature for 6 hours. The reaction solution was concentrated under reduced pressure, and the residue was purified by silica gel column chromatography (n-hexane-ethyl acetate 1:4, v/v) to obtain 1.77 g (yield 79%) of Compound 1C as an oil product.

$^1$H-NMR (CDCl$_3$) δ: 2.90 (3H, br), 3.25 (3H, br), 3.69 (3H, s), 4.45 (2H, s), 4.59 (2H, s), 7.24-7.40 (5H, m), 7.73 (s, 1H).

Third Step

Sodium tert-butoxide (2.55 g, 23.2 mmol), dimethyl oxalate (639 mg, 5.41 mmol) and DMI (3 ml) were added to a three-neck flask under a nitrogen atmosphere, and a solution of Compound 1C (0.50 g, 1.80 mmol) in DMI (2 ml) was added dropwise thereto at 25 to 30° C. After stirring at room temperature for 7 hours, 2N hydrochloric acid (10 ml) was added, and the mixture was stirred at room temperature for 15 hours. The reaction solution was extracted with ethyl acetate two times, and the combined extracts were washed sequentially with water, saturated sodium bicarbonate water, water and saturated sodium chloride water, and then dried with anhydrous sodium sulfate. The solvent was distilled off, and the resulting residue was purified by silica gel column chromatography (n-hexane-ethyl acetate 2:1 to 1:1, v/v) to obtain 488 mg (yield 85%) of Compound 1D as a white crystal.

$^1$H-NMR (CDCl$_3$) δ: 3.89 (3H, s), 3.93 (3H, s), 5.34 (2H, s), 7.32-7.40 (3H, m), 7.45-7.49 (2H, m), 8.50 (1H, s).

Example 2

[Chemical formula 65]

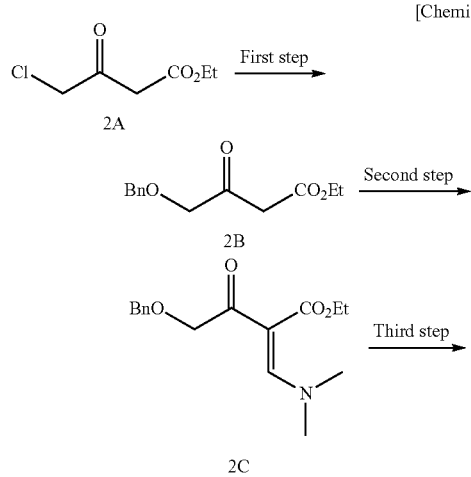

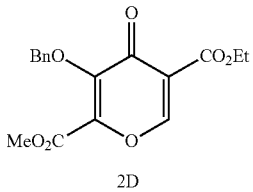

2D

First Step

A solution of benzyl alcohol (0.66 g, 6.1 mmol) in DMI (3 ml) was added to a suspension of sodium tert-pentoxide (1.67 g, 15.2 mmol) in DMI (4 ml) at room temperature under a nitrogen atmosphere, and the mixture was stirred at 40° C. for 2 hours. This reaction solution was cooled in an ice bath, and a solution of Compound 2A (1.10 g, 6.68 mmol) in DMI (3 ml) was added dropwise at 0 to 10° C. The reaction solution was stirred at 0 to 5° C. for 2 hours, and at room temperature for 3 hours, and 2N hydrochloric acid (15 ml) was added, followed by extraction with ethyl acetate two times. The combined extracts were washed sequentially with water, saturated sodium bicarbonate water, water and saturated sodium chloride water, and then dried with anhydrous sodium sulfate. The solvent was distilled off, and the resulting oil product was purified by silica gel column chromatography (n-hexane-ethyl acetate 4:1, v/v) to obtain 1.29 g (yield 90%) of Compound 2B as an oil product.

$^1$H-NMR (CDCl$_3$) δ: 1.25 (3H, t, J=7.2 Hz), 3.54 (2H, s), 4.14 (2H, s), 4.17 (2H, q, J=7.2 Hz), 4.59 (2H, s), 7.28-7.40 (5H, m).

Second Step

Compound 2B (9.73 g, 41.2 mmol) was dissolved in toluene (45 ml), N,N-dimethylformamide dimethyl acetal (7.36 g, 61.8 mmol) was added, and the mixture was stirred at room temperature for 5 hours. Water was added to the reaction solution, followed by extraction with ethyl acetate two times. The combined extracts were washed sequentially with water, and saturated sodium chloride water, and then dried with anhydrous magnesium sulfate. The solvent was distilled off, and the resulting oil product was purified by silica gel column chromatography (n-hexane-ethyl acetate 1:1 to 3:7, v/v) to obtain 7.90 g (yield 66%) of Compound 2C as an oil product.

$^1$H-NMR (CDCl$_3$) δ: 1.25 (3H, t, J=7.2 Hz), 2.95 (3H, br), 3.22 (3H, br), 4.15 (2H, q, J=7.2 Hz), 4.45 (2H, s), 4.59 (2H, s), 7.22-7.40 (5H, m), 7.73 (1H, s).

Third Step

Sodium tert-butoxide (495 mg, 5.15 mmol) and DMI (2 ml) were added to a three-neck flask under a nitrogen atmosphere, and dimethyl oxalate (608 mg, 5.15 mmol) and a solution of Compound 2C (0.50 g, 1.72 mmol) in DMI (3 ml) was added dropwise at 25 to 30° C. After stirring at room temperature for 4 hours, 2N hydrochloric acid (10 ml) was added, and the mixture was stirred at room temperature for 15 hours. The reaction solution was extracted with toluene two times, and the combined extracts were washed sequentially with water, saturated sodium bicarbonate water, water and saturated sodium chloride water, and then dried with anhydrous sodium sulfate. The solvent was distilled off, and the resulting residue was purified by silica gel column chromatography (n-hexane-ethyl acetate 2:1, v/v) to obtain 420 mg (yield 74%) of Compound 2D as a white crystal.

$^1$H-NMR (CDCl$_3$) δ: 1.39 (3H, t, J=7.2 Hz), 3.88 (3H, s), 4.39 (2H, q, J=7.2 Hz), 5.34 (2H, s), 7.30-7.41 (3H, m), 7.45-7.50 (2H, m), 8.48 (1H, s).

Example 3

[Chemical formula 66]

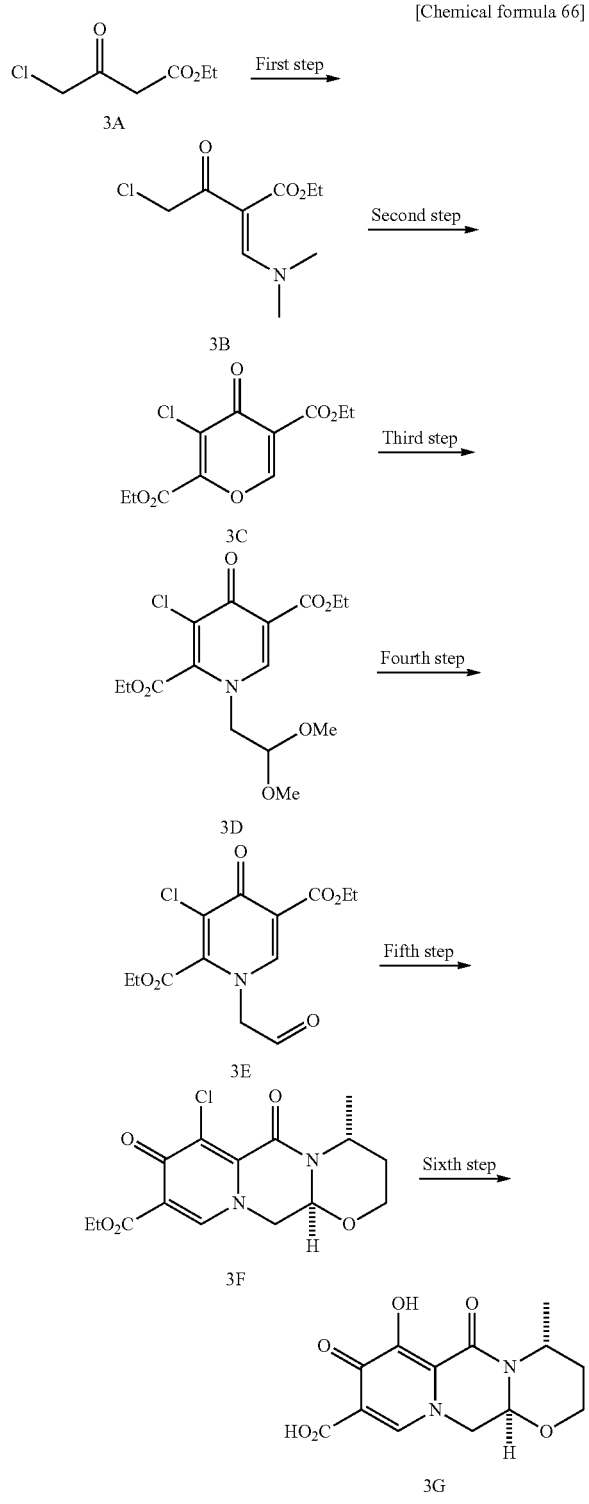

First Step

N,N-dimethylformamide dimethyl acetal (4.9 ml, 36.5 mmol) was added dropwise to Compound 3A (5.0 g, 30.4 mmol) at 0° C. under cooling. After stirring at 0° C. for 1 hour, 100 ml of ethyl acetate was added to the reaction solution, followed by washing with 0.5N hydrochloric acid (50 ml). The aqueous layer was separated, and extracted with ethyl acetate (50 ml). The organic layers were combined, washed sequentially with saturated sodium bicarbonate water and saturated sodium chloride water, and then dried with anhydrous sodium sulfate. The solvent was distilled off, and the resulting residue was purified by silica gel column chromatography (n-hexane-ethyl acetate 1:1 (v/v)→ethyl acetate) to obtain 4.49 g (yield 67%) of Compound 3B as an oil product.

$^1$H-NMR (CDCl$_3$) δ: 1.32 (3H, t, J=7.1 Hz), 2.90 (3H, br s), 3.29 (3H, br s), 4.23 (2H, q, J=7.1 Hz), 4.54 (2H, s), 7.81 (1H, s).

Second Step

Lithium hexamethyldisilazide (1.0 M toluene solution, 49 ml, 49.0 mmol) was diluted with tetrahydrofuran (44 ml), a solution of Compound 3B (4.49 g, 20.4 mmol) in tetrahydrofuran (10 ml) was added dropwise thereto at −78° C. under cooling, and a solution of ethyl oxalyl chloride (3.35 g, 24.5 mmol) in tetrahydrofuran (10 ml) was added dropwise. After stirring at −78° C. for 2 hours, a temperature was raised to 0° C. After 2N hydrochloric acid was added to the reaction solution, and the mixture was stirred for 20 minutes, the solution was extracted with ethyl acetate (200 ml×2), and the organic layer was washed with saturated sodium bicarbonate water and saturated sodium chloride water and then dried with anhydrous sodium sulfate. The solvent was distilled off, and the resulting residue was purified by silica gel column chromatography (n-hexane-ethyl acetate 7:3→5:5→0:10 (v/v)) to obtain 1.77 g (yield 31%) of Compound 3C as a white solid.

$^1$H-NMR (CDCl$_3$) δ: 1.36-1.46 (6H, m), 4.35-4.52 (8H, m), 8.53 (1H, s).

Third Step

Aminoacetaldehyde dimethyl acetal (0.13 ml, 1.20 mmol) was added to a solution of Compound 3C (300 mg, 1.09 mmol) in ethanol (6 ml) at 0° C., and the mixture was stirred at 0° C. for 1 hour and 30 minutes, at room temperature for 18 hours and, then, at 60° C. for 4 hours. After the solvent was distilled off from the reaction solvent under reduced pressure, the resulting residue was purified by silica gel column chromatography (n-hexane-ethyl acetate 5:5→0:10 (v/v)) to obtain 252 mg (yield 64%) of Compound 3D as an oil product.

$^1$H-NMR (CDCl$_3$) δ: 1.36-1.47 (6H, m), 3.42 (6H, s), 3.90 (2H, d, J=5.2 Hz), 4.37 (3H, q, J=7.2 Hz), 4.50 (2H, q, J=7.2 Hz), 8.16 (1H, s).

Fourth Step

To a solution of Compound 3D (1.02 g, 2.82 mmol) in formic acid (10 ml), 62%-H$_2$SO$_4$ (892 mg, 5.64 mmol) was added and the mixture was stirred at room temperature for 16 hours. Formic acid was distilled off under reduced pressure, methylene chloride was added to the residue, and saturated sodium chloride water was added to adjust a pH to 6.6. The methylene chloride layer was separated, and the aqueous layer was extracted with methylene chloride. The methylene chloride layers were combined, and dried with anhydrous sodium sulfate. The solvent was distilled off to obtain 531.8 mg of Compound 3E as a yellow oil product.

$^1$H-NMR (CDCl$_3$) δ: 1.28-1.49 (6H, m), 4.27-4.56 (4H, m), 4.84 (2H, s), 8.10 (1H, s), 9.72 (1H, s).

Fifth Step

Methanol (0.20 ml, 5.0 mmol), (R)-3-amino-butan-1-ol (179 mg, 2.0 mmol) and acetic acid (0.096 ml, 1.70 mmol)

were added to a solution of Compound 3E (531 mg, 1.68 mmol) in toluene (5 ml), and the mixture was heated to reflux for 4 hours. The reaction solution was cooled to room temperature, diluted with chloroform, and then washed with saturated sodium bicarbonate water, and the aqueous layer was extracted with chloroform. The chloroform layers were combined, washed with saturated sodium chloride water, and then dried with anhydrous sodium sulfate. The solvent was distilled off, and the resulting residue was purified by silica gel column chromatography (chloroform-methanol 100:0→90:10) to obtain 309.4 mg of Compound 3F as a brown oil product.

$^1$H-NMR (CDCl$_3$) δ: 1.40 (3H, t, J=7.1 Hz), 1.40 (3H, d, J=7.1 Hz), 1.55-1.61 (1H, m), 2.19-2.27 (1H, m), 4.00 (1H, d, J=1.5 Hz), 4.03 (1H, d, J=2.5 Hz), 4.10 (1H, dd, J=13.2, 6.3 Hz), 4.26 (1H, dd, J=13.2, 3.8 Hz), 4.38 (2H, q, J=7.1 Hz), 5.00-5.05 (1H, m), 5.31 (1H, dd, J=6.4, 3.9 Hz), 8.10 (1H, s).

Sixth Step

Potassium trimethylsilanolate (333 mg, 2.34 mmol) was added to a solution of Compound 3F (159 mg, 0.47 mmol) in 1,2-dimethoxyethane (2 ml), and the mixture was stirred at room temperature for 7 hours. 1N-hydrochloric acid and saturated sodium chloride water were added to the reaction solution, followed by extraction with chloroform. The chloroform layers were combined, and dried with anhydrous sodium sulfate. The solvent was distilled off to obtain 34.4 mg (yield 25%) of Compound 3G as an orange powder.

$^1$H-NMR (CDCl$_3$) δ: 1.46 (3H, d, J=3.5 Hz), 1.58-1.65 (1H, m), 2.26-2.30 (1H, m), 4.06-4.10 (2H, m), 4.31 (1H, dd, J=13.8, 5.6 Hz), 4.48 (1H, dd, J=13.6, 3.9 Hz), 5.03 (1H, t, J=6.4 Hz), 5.36 (1H, dd, J=5.5, 4.0 Hz), 8.44 (1H, s), 12.80 (1H, s), 14.90 (1H, s).

Example 4

[Chemical formula 67]

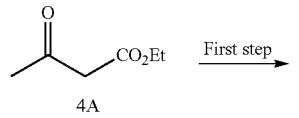

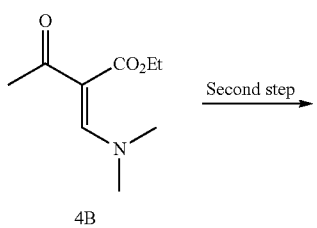

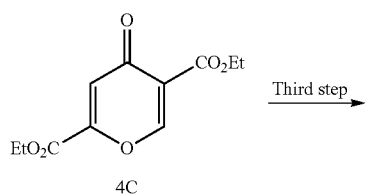

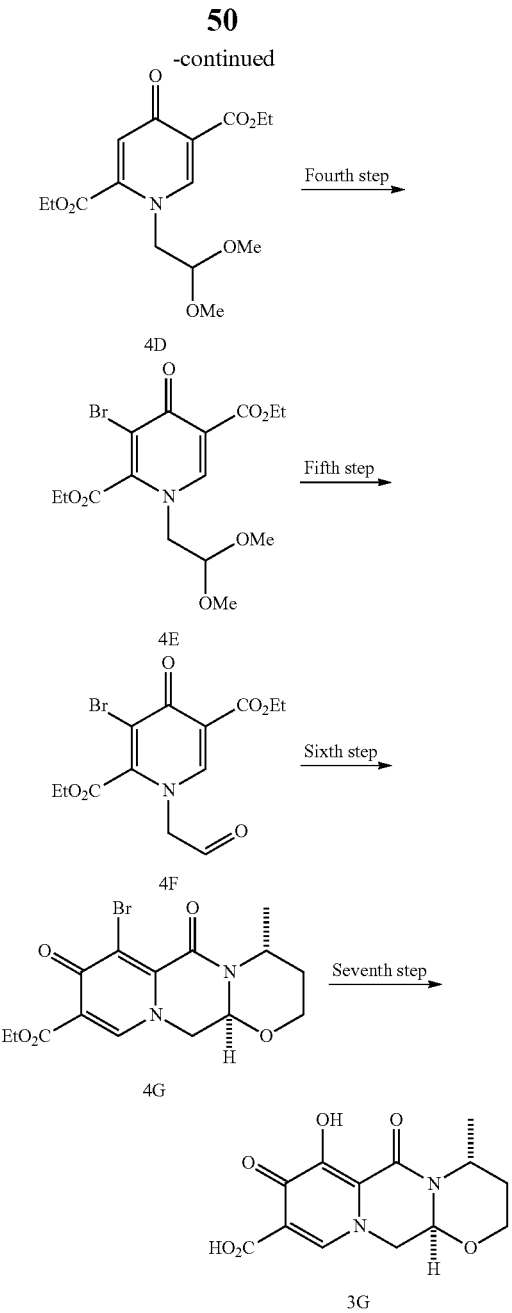

First Step

N,N-dimethylformamide dimethyl acetal (12.2 ml, 92.2 mmol) was added dropwise to Compound 4A (10.0 g, 76.8 mmol) at 0° C. under cooling. After stirring at 0° C. for 1 hour and 30 minutes and, then, at room temperature for 2 hours and 30 minutes, 100 ml of ethyl acetate was added to the reaction solution, and the solvent was distilled off. The resulting residue was purified by silica gel column chromatography (n-hexane-ethyl acetate 5:5→0:10 (v/v)) to obtain 12.45 g (yield 88%) of Compound 4B as an oil product.

$^1$H-NMR (CDCl$_3$) δ: 1.32 (3H, t, J=7.1 Hz), 2.33 (3H, s), 3.04 (6H, br s), 4.23 (2H, q, J=7.2 Hz), 7.68 (1H, s).

Second Step

Lithium hexamethyldisilazide (1.0M toluene solution, 24 ml, 24.0 mmol) was diluted with tetrahydrofuran (20 ml), a solution of Compound 4B (1.85 g, 10.0 mmol) in tetrahydrofuran (5 ml) was added dropwise thereto at −78° C. under cooling, and a solution of ethyl oxalyl chloride (1.34 ml, 12.0 mmol) in tetrahydrofuran (5 ml) was added dropwise. After stirring at −78° C. for 2 hours, 2N-hydrochloric acid was added to the reaction solution, and the mixture was stirred at room temperature for 20 minutes. The solution was extracted with ethyl acetate, and the organic layer was washed sequentially with saturated sodium bicarbonate water and saturated sodium chloride water, and then dried with anhydrous sodium sulfate. The solvent was distilled off, and the resulting residue was purified by silica gel column chromatography (n-hexane-ethyl acetate 75:25→455:5 (v/v)) to obtain 1.03 g (yield 43%) of Compound 4C as a brown oil product.

$^1$H-NMR (CDCl$_3$) δ: 1.38 (3H, t, J=7.1 Hz), 1.42 (3H, t, J=7.4 Hz), 4.33-4.47 (4H, m), 7.19 (1H, s), 8.54 (1H, s).

Third Step

Aminoacetaldehyde dimethyl acetal (0.34 ml, 3.11 mmol) was added to a solution of Compound 4C (680 mg, 2.83 mmol) in ethanol (6.8 ml) at 0° C., and it was allowed to stand at room temperature for 16 hours. After the solvent was distilled off from the reaction solution under reduced pressure, the resulting residue was purified by silica gel column chromatography (n-hexane-ethyl acetate 90:10 (v/v)) to obtain 875 mg (yield 94%) of Compound 4D as an oil product.

$^1$H-NMR (CDCl$_3$) δ: 1.38 (3H, t, J=7.1 Hz), 1.39 (3H, t, J=7.1 Hz), 3.40 (6H, s), 4.33 (2H, d, J=4.7 Hz), 4.37 (4H, q, J=7.1 Hz), 4.49 (1H, t, J=4.7 Hz), 7.06 (1H, s), 8.17 (1H, s).

Fourth Step

N-bromosuccinimide (1.46 g, 8.18 mmol) was added to a solution of Compound 4D (2.68 g, 8.18 mmol) in N,N-dimethylformamide (10 ml), and the mixture was stirred at room temperature for 48 hours. After saturated sodium bicarbonate water was added to the reaction solution, the solution was extracted with ethyl acetate, and the organic layer was washed sequentially with water and saturated sodium chloride water, and then dried with anhydrous sodium sulfate. The solvent was distilled off, and the resulting residue was purified by silica gel column chromatography (n-hexane-ethyl acetate 90:10 (v/v)) to obtain 2.83 g (yield 85%) of Compound 4E as an oil product.

$^1$H-NMR (CDCl$_3$) δ: 1.41 (3H, t, J=7.1 Hz), 1.48 (3H, t, J=7.1 Hz), 3.42 (6H, s), 3.90 (2H, d, J=5.0 Hz), 4.39 (2H, q, J=7.1 Hz), 4.53 (3H, q, J=14.3 Hz), 4.54 (3H, s), 4.57 (3H, t, J=5.4 Hz), 8.19 (1H, s).

Fifth Step

To a solution of Compound 4E (2.23 g, 5.49 mmol) in formic acid (15 ml), 62%-H$_2$SO$_4$ (1.74 g, 10.98 mmol) was added and the mixture was stirred at room temperature for 8 hours. A 0.5N-aqueous sodium hydroxide solution (120 ml) was added, followed by extraction with methylene chloride. The methylene chloride layers were combined, washed with saturated sodium chloride water, and then dried with anhydrous sodium sulfate. The solvent was distilled off to obtain 1.31 g of Compound 4F as a white powder.

$^1$H-NMR (CDCl$_3$) δ: 1.31-1.46 (6H, m), 4.33-4.48 (4H, m), 4.82 (2H, s), 8.11 (1H, s), 9.71 (1H, s).

Sixth Step

Methanol (0.44 ml, 10.9 mmol), (R)-3-amino-butane-1-ol (389 mg, 4.36 mmol) and acetic acid (0.21 ml, 3.64 mmol) were added to a solution of Compound 4F (1.31 g, 3.64 mmol) in toluene (13 ml), and the mixture was heated to reflux for 3 hours. The reaction solution was cooled to room temperature, diluted with chloroform, and then washed with saturated sodium bicarbonate water, and the aqueous layer was extracted with chloroform. The chloroform layers were combined, washed with saturated sodium chloride water, and then dried with anhydrous sodium sulfate. The solvent was distilled off, and the resulting residue was purified by silica gel column chromatography (chloroform-methanol 100:0→90:10) to obtain 1.58 g of Compound 4G as an oil product.

$^1$H-NMR (CDCl$_3$) δ: 1.40 (3H, d, J=5.7 Hz), 1.56-1.60 (1H, m), 2.19-2.24 (1H, m), 3.99 (1H, d, J=2.0 Hz), 4.02 (1H, d, J=2.4 Hz), 4.11 (1H, dd, J=13.3, 6.7 Hz), 4.28 (1H, dd, J=13.3, 3.9 Hz), 4.36 (3H, q, J=7.1 Hz), 4.49-4.56 (1H, m), 4.98-5.03 (1H, m), 5.34 (1H, dd, J=6.6, 3.8 Hz), 8.07 (1H, s).

Seventh Step

Potassium trimethylsilanolate (249 mg, 1.95 mmol) was added to a solution of Compound 4G (300 mg, 0.78 mmol) in 1,2-dimethoxyethane (3 ml), and the mixture was stirred at room temperature for 1 hour. Potassium trimethylsilanolate (249 mg, 1.95 mmol) was additionally added, and the mixture was further stirred at 60° C. for 1 hour. 1N-hydrochloric acid and saturated sodium chloride water were added to the reaction solution, followed by extraction with chloroform. The chloroform layers were combined, and dried with anhydrous sodium sulfate. The solvent was distilled off to obtain 100.3 mg (yield 43%) of Compound 3G as a yellow powder.

$^1$H-NMR (CDCl$_3$) δ: 1.46 (3H, d, J=3.5 Hz), 1.58-1.65 (1H, m), 2.26-2.30 (1H, m), 4.06-4.10 (2H, m), 4.31 (1H, dd, J=13.8, 5.6 Hz), 4.48 (1H, dd, J=13.6, 3.9 Hz), 5.03 (1H, t, J=6.4 Hz), 5.36 (1H, dd, J=5.5, 4.0 Hz), 8.44 (1H, s), 12.80 (1H, s), 14.90 (1H, s).

Example 5

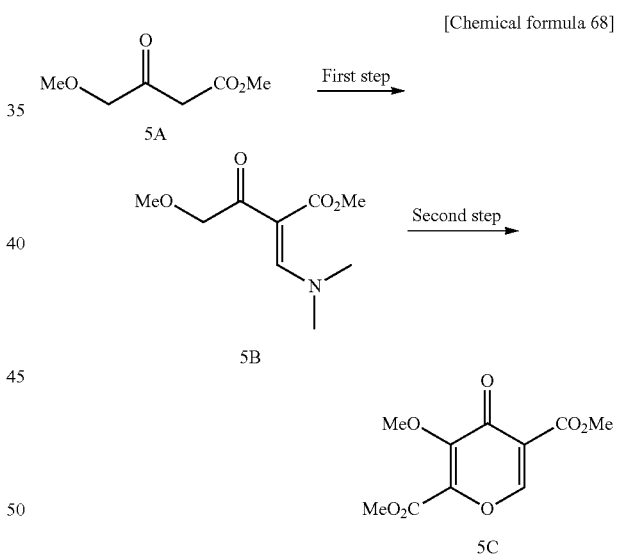

[Chemical formula 68]

First Step

Compound 5A (598 mg, 4.09 mmol) and N,N-dimethylformamide dimethyl acetal (488 mg, 4.09 mmol) were dissolved in toluene (1 ml), and the mixture was stirred at room temperature for 11 hours. The solvent was distilled off from the reaction solution under reduced pressure, and the resulting residue (containing Compound 5B) was used in Second step without purification.

Second Step

Sodium tert-butoxide (400 mg, 4.16 mmol) was suspended in dimethyl imidazolidinone (5 ml), a solution of the crude product obtained in First step in dimethylimidazolidinone (5 ml) was added thereto, a solution of dimethyl oxalate (983 mg, 8.32 mmol) in THF (10 ml) was added dropwise, and the mixture was stirred at room temperature for 45 minutes. The reaction solution was poured into 2N hydrochloric acid-methanol (20 ml), and the mixture was stirred at 0° C. for 20 minutes. Water was added, the solution was extracted with ethyl acetate, and the organic layer was washed sequentially with water, saturated sodium bicarbonate water, and saturated sodium chloride water, and dried with anhydrous sodium sulfate. After the solvent was distilled off, the resulting residue was purified by silica gel column chromatography to obtain 222 mg (yield: 22% from 5A) of Compound 5C.

$^1$H-NMR (CDCl$_3$) δ: 3.91 (3H, s), 3.97 (3H, s), 4.05 (3H, s), 8.50 (1H, s).

Example 6

[Chemical formula 69]

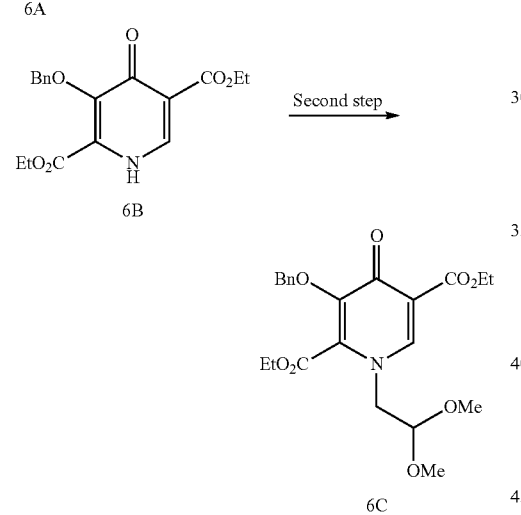

First Step

Lithium hexamethyldisilazide (1.0M toluene solution, 12 ml, 12.0 mmol) was diluted with tetrahydrofuran (11 ml), a solution of Compound 6A (1.46 g, 5.0 mmol) in tetrahydrofuran (2 ml) was added dropwise thereto at −78° C. under cooling, and a solution of ethyl oxalyl chloride (0.67 ml, 6.0 mmol) in tetrahydrofuran (2 ml) was added dropwise. After stirring at −78° C. for 2 hours, ammonium acetate (500 mg) and acetic acid (10 ml) were added to the reaction solution, and the mixture was stirred at 65° C. for 1 hour and 30 minutes. Water was added to the reaction solution, the solvent was extracted with ethyl acetate, and the organic layer was washed sequentially with water, and saturated sodium bicarbonate water, and dried with anhydrous sodium sulfate. The solvent was distilled off, and the resulting residue was purified by silica gel column chromatography (N-hexane-ethyl acetate 55:45→45:55 (v/v)) to obtain 505.1 mg of Compound 6B as a yellow solid. It was washed with isopropyl ether-hexane (1:2), and dried under reduced pressure to obtain 416.8 mg (yield 24%) of Compound 6B as a yellow crystal.

$^1$H-NMR (CDCl$_3$) δ: 1.35 (3H, t, J=7.1 Hz), 1.46 (3H, t, J=7.1 Hz), 4.40 (2H, q, J=7.2 Hz), 4.50 (2H, q, J=7.1 Hz), 5.20 (2H, s), 7.33-7.41 (3H, m), 7.49-7.52 (2H, m), 8.76 (1H, s), 11.61 (1H, br s).

Second Step

Cesium carbonate (73.3 mg, 0.23 mmol) and bromoacetaldehyde dimethyl acetal (38.0 mg, 0.23 mmol) were added to a solution of Compound 6B (51.8 mg, 0.15 mmol) in N,N-dimethylformamide (1 ml), and the mixture was stirred at room temperature overnight. Cesium carbonate (73.3 mg, 0.23 mmol) and bromoacetaldehyde dimethyl acetal (38.0 mg, 0.23 mmol) were further added, and the mixture was further stirred at 100° C. for 20 minutes. After water was added to the reaction solution, the solution was extracted with ethyl acetate, and the organic layer was washed sequentially with water and saturated sodium chloride water, and dried with anhydrous sodium sulfate. The solvent was distilled off, and the resulting residue was purified by silica gel column chromatography (n-hexane-ethyl acetate 50:50→30:70 (v/v)) to obtain 35.3 mg (yield 54%) of Compound 6C as a colorless oil product.

$^1$H-NMR (CDCl$_3$) δ: 1.26 (3H, t, J=7.1 Hz), 1.40 (3H, t, J=7.1 Hz), 3.39 (6H, s), 3.91 (2H, d, J=5.0 Hz), 4.29 (2H, q, J=7.1 Hz), 4.40 (2H, q, J=7.2 Hz), 4.50 (1H, t, J=5.0 Hz), 5.30 (2H, s), 7.31-7.37 (3H, m), 7.43-7.46 (2H, m), 8.12 (1H, s).

Example 7

[Chemical formula 70]

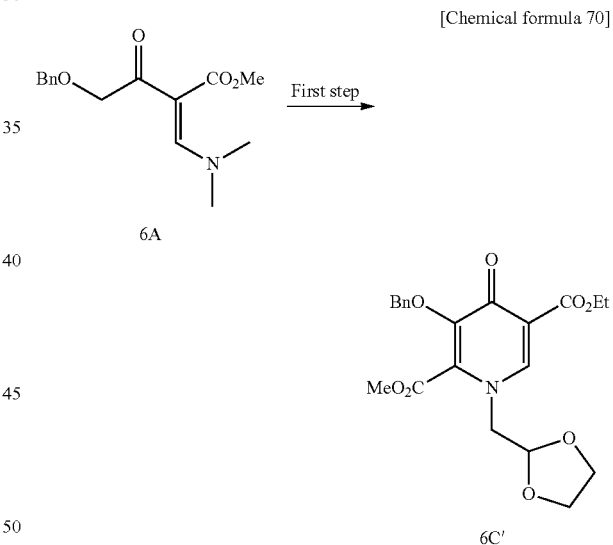

First Step

Compound 6A (291 mg, 1.0 mmol) and dimethyl oxalate (354 mg, 3.0 mmol) were dissolved in dimethylimidazolidinone (1.4 ml), sodium methoxide (28%-methanol solution, 0.30 ml, 1.5 mmol) was added thereto, and the mixture was stirred at room temperature for 2 hours. 1,3-Dioxolan-2-yl-methylamine (154 mg, 1.5 mmol) and acetic acid (0.29 ml, 5.0 mmol) were added thereto, and the mixture was stirred at room temperature for 38 hours. Saturated sodium bicarbonate water was added to the reaction solution, followed by extraction with ethyl acetate. The ethyl acetate layers were combined, washed sequentially with water and saturated sodium chloride water, and then dried with anhydrous sodium sulfate. After the solvent was distilled off, the resulting residue was purified by silica gel column chromatography (hexane-ethyl acetate 33:67→15:85) to obtain 294.8 mg (yield 70%) of Compound 6C' as a pale yellow oil product.

$^1$H-NMR (CDCl$_3$) δ: 1.43 (3H, t, J=7.1 Hz), 3.73-3.75 (2H, m), 3.81 (3H, s), 3.82-3.85 (2H, m), 4.21 (2H, d, J=2.2 Hz), 4.42 (2H, q, J=7.1 Hz), 5.14 (1H, t, J=2.3 Hz), 5.32 (2H, s), 7.34-7.37 (3H, m), 7.44-7.46 (2H, m), 8.14 (1H, s).

Example 8

[Chemical formula 71]

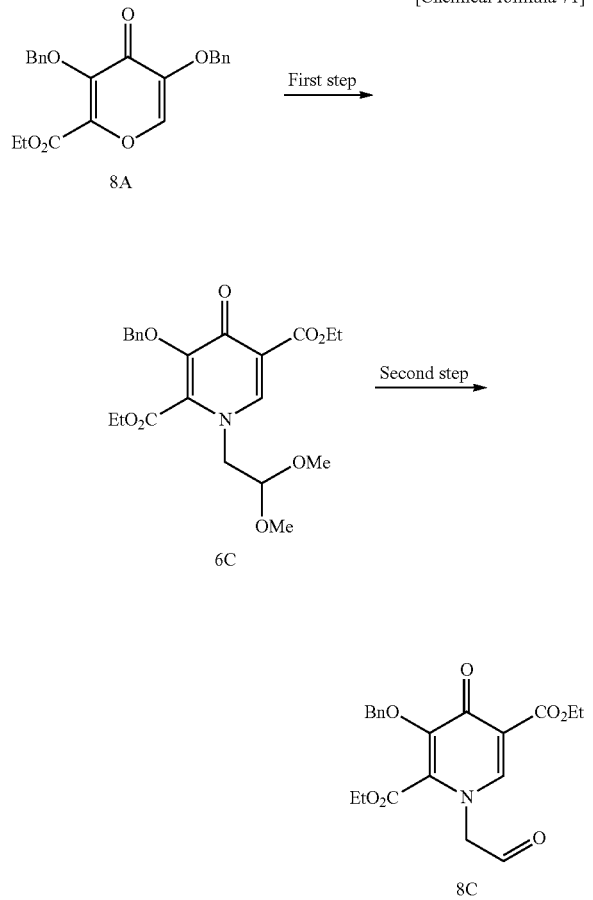

First Step

Aminoacetaldehyde dimethyl acetal (7.80 mmol) was added to a solution of Compound 8A (900 mg, 2.60 mmol) in ethanol (5 ml), and the mixture was stirred at room temperature for 22 hours. Ethyl acetate (5 ml) and water (5 ml) were added to the reaction solution, followed by extraction with ethyl acetate (5 ml). After the organic layer was washed with water (10 ml), the solvent was distilled off, and the resulting residue was purified by silica gel column chromatography (n-hexane-ethyl acetate 2:1) to obtain 0.37 g (yield 33%) of Compound 6C as a colorless oil product.

$^1$H-NMR (CDCl$_3$) δ: 7.90 (1H, s), 7.45-7.43 (5H, m), 5.30 (2H, s), 4.51 (1H, t, J=5.1 Hz), 4.40 (2H, q, J=7.1 Hz), 4.30 (2H, q, J=7.1 Hz), 3.91 (2H, d, J=5.1 Hz), 3.46 (6H, s), 1.40 (3H, t, J=7.1 Hz), 1.26 (3H, t, J=7.1 Hz).

Second Step

To a solution of Compound 6C (433.5 mg, 1.0 mmol) in formic acid (4 ml), 62%-H$_2$SO$_4$ (316 mg, 2.0 mmol) was added and the mixture was stirred at room temperature for 3 hours. Methylene chloride was added to the reaction solution, the solution was washed with a 0.5N-aqueous sodium hydroxide solution (12 ml), and the aqueous layer was extracted with methylene chloride. The methylene chloride layers were combined, washed with saturated sodium chloride water, and then dried with anhydrous sodium sulfate. The solvent was distilled off to obtain 207.6 mg (yield 51%) of Compound 8C as a yellow foam product.

$^1$H-NMR (CDCl$_3$) δ: 1.23 (3H, t, J=7.1 Hz), 1.42 (3H, t, J=7.1 Hz), 4.25 (2H, q, J=7.2 Hz), 4.42 (2H, q, J=7.1 Hz), 4.79 (2H, s), 5.34 (2H, s), 7.31-7.53 (5H, m), 8.05 (1H, s), 9.67 (1H, s).

Example 9

[Chemical formula 72]

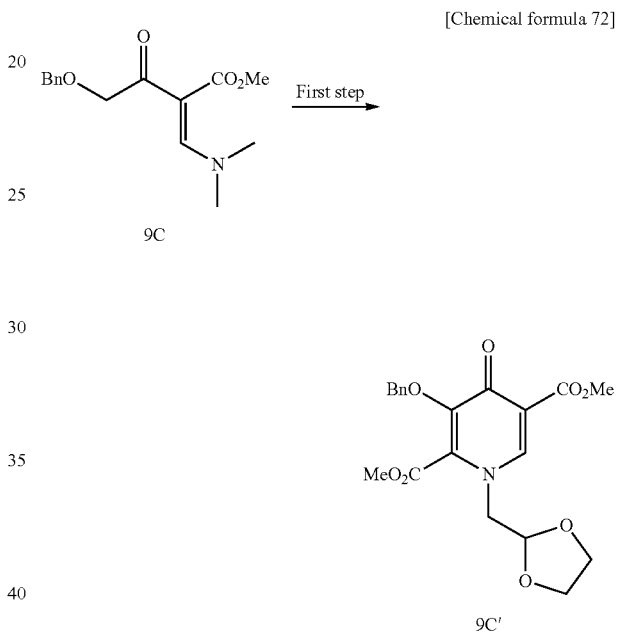

First Step

Compound 9C (291.3 mg, 10 mmol) was dissolved in DMI (1.4 mL) in a two-neck flask under a nitrogen atmosphere, dimethyl oxalate (354.3 mg, 3.0 mmol), and sodium methoxide (28%-methanol solution 0.3 mL, 1.5 mmol) were added, and the mixture was stirred at room temperature for 2 hours.

2-(Aminomethyl)-1,3-dioxane (154.7 mg, 1.5 mmol) and acetic acid (0.29 mL, 5.0 mmol) were added thereto, and the mixture was stirred at room temperature for 5 hours. Ethyl acetate (50 mL) was added to the reaction solution, and the solution was washed sequentially with water (20 mL), a 10%-aqueous ammonium chloride solution (20 mL), water (20 mL) and saturated sodium chloride water (20 mL), and dried with anhydrous magnesium sulfate. The solvent was distilled off, and the resulting residue was purified by silica gel column chromatography (n-hexane-ethyl acetate 1:1→1:3, v/v) to obtain 99.0 mg (yield 25%) of Compound 9C' as a white crystal.

$^1$H-NMR (CDCl$_3$) δ: 8.14 (1H, s), 7.44-7.42 (5H, m), 5.29 (2H, s), 5.12 (1H, s), 4.19 (2H, s), 3.93 (3H, s), 3.83-3.70 (2H, m), 3.83 (2H, s).

Example 10

Example 11

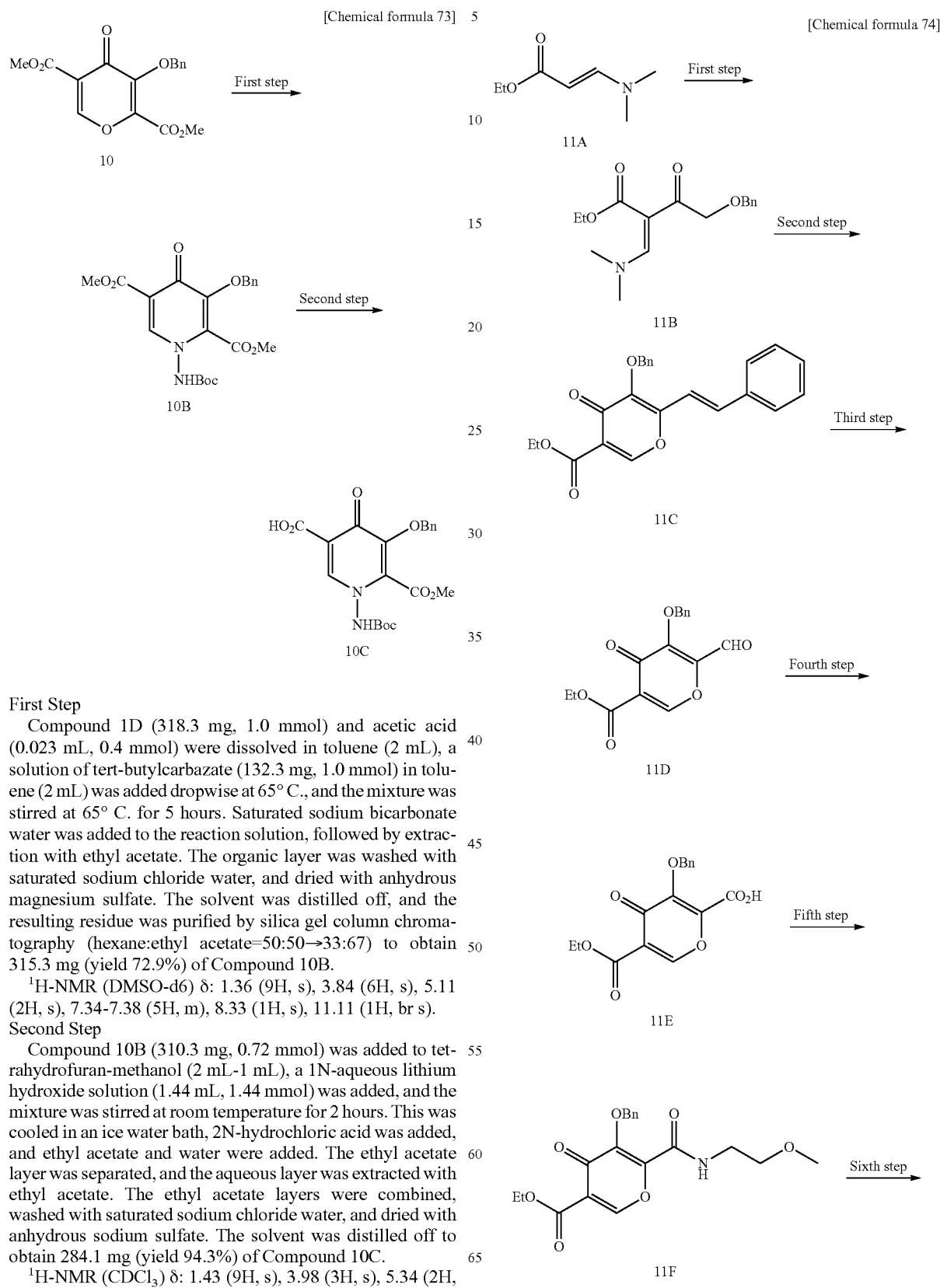

[Chemical formula 73]

[Chemical formula 74]

First Step

Compound 1D (318.3 mg, 1.0 mmol) and acetic acid (0.023 mL, 0.4 mmol) were dissolved in toluene (2 mL), a solution of tert-butylcarbazate (132.3 mg, 1.0 mmol) in toluene (2 mL) was added dropwise at 65° C., and the mixture was stirred at 65° C. for 5 hours. Saturated sodium bicarbonate water was added to the reaction solution, followed by extraction with ethyl acetate. The organic layer was washed with saturated sodium chloride water, and dried with anhydrous magnesium sulfate. The solvent was distilled off, and the resulting residue was purified by silica gel column chromatography (hexane:ethyl acetate=50:50→33:67) to obtain 315.3 mg (yield 72.9%) of Compound 10B.

$^1$H-NMR (DMSO-d6) δ: 1.36 (9H, s), 3.84 (6H, s), 5.11 (2H, s), 7.34-7.38 (5H, m), 8.33 (1H, s), 11.11 (1H, br s).

Second Step

Compound 10B (310.3 mg, 0.72 mmol) was added to tetrahydrofuran-methanol (2 mL-1 mL), a 1N-aqueous lithium hydroxide solution (1.44 mL, 1.44 mmol) was added, and the mixture was stirred at room temperature for 2 hours. This was cooled in an ice water bath, 2N-hydrochloric acid was added, and ethyl acetate and water were added. The ethyl acetate layer was separated, and the aqueous layer was extracted with ethyl acetate. The ethyl acetate layers were combined, washed with saturated sodium chloride water, and dried with anhydrous sodium sulfate. The solvent was distilled off to obtain 284.1 mg (yield 94.3%) of Compound 10C.

$^1$H-NMR (CDCl$_3$) δ: 1.43 (9H, s), 3.98 (3H, s), 5.34 (2H, s), 7.36-7.37 (5H, m), 8.44 (1H, s), 14.53 (1H, br s).

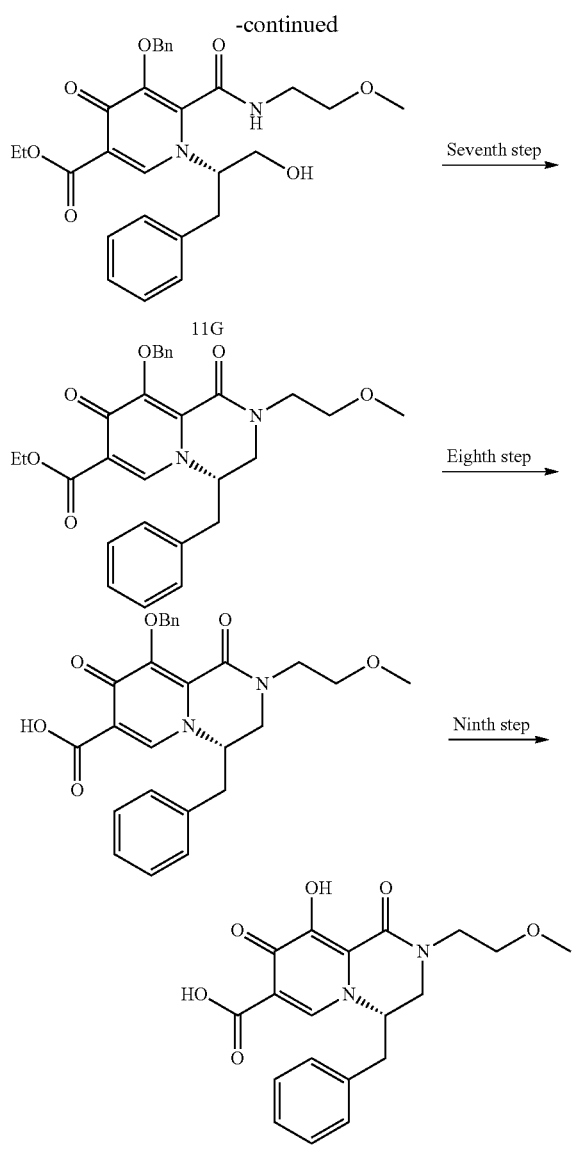

First Step

A solution of Compound 11A (12.8 g, 89.4 mmol) and pyridine (8.50 g, 107 mmol) in dichloromethane (90 mL) was cooled to 1 to 3° C., and a solution of benzyloxyacetyl chloride (19.8 g, 107 mmol) in dichloromethane (90 mL) was added dropwise over 50 minutes while the same temperature was retained. After the reaction solution was stirred at the same temperature for 30 minutes, a temperature was gradually raised to 15° C. over 60 minutes, and ice water was added. The dichloromethane layer was separated, and the aqueous layer was extracted with dichloromethane once. The combined extracts were washed with water three times, washed with saturated sodium chloride water, and then dried. The solvent was distilled off, and the resulting oil product was purified by subjecting it to silica gel column chromatography. First, the oil product was eluted first with n-hexane and, then, with n-hexane-ethyl acetate (1:1, v/v). The objective fraction was concentrated to obtain 22.2 g of Compound 11B as an oil product.

$^1$H-NMR (CDCl$_3$) δ: 1.25 (3H, t, J=7.2 Hz), 2.90 (3H, brs), 3.24 (3H, brs), 4.15 (2H, q, J=7.2 Hz), 4.45 (2H, s), 4.58 (2H, s), 7.25-7.38 (5H, m), 7.72 (1H, s).

Second Step

A 1N lithium hexamethyldisilazane THF solution (4.29 ml, 4.29 mmol) was cooled to −78° C., and a solution of Compound 11B (500 mg, 1.72 mmol) and cinnamoyl chloride (343.2 mg, 2.06 mmol) in THF (4 ml) was added dropwise over 3 minutes while the same temperature was retained. After the reaction solution was stirred at the same temperature for 25 minutes, 2N hydrochloric acid (10 ml) was added, and the mixture was further stirred at room temperature for 10 minutes. To the reaction solution was added ethyl acetate, the organic layer was separated, and the aqueous layer was extracted with ethyl acetate three times. The combined extracts were dried with sodium sulfate. The solvent was distilled off, and the resulting oil product was purified by subjecting it to silica gel column chromatography. From a fraction eluting with n-hexane-ethyl acetate (1:1, v/v), 364.3 mg (yield 56%) of Compound 11C was obtained as a solid.

$^1$H-NMR (CDCl$_3$) δ: 1.40 (3H, t, J=7.2 Hz), 4.39 (2H, q, J=7.2 Hz), 5.27 (2H, s), 6.99 (1H, d, J=16.2 Hz), 7.23 (1H, d, J=16.2), 7.26-7.48 (10H, m), 8.45 (1H, s).

Third Step

Under a nitrogen atmosphere, a solution of sodium periodate (625.8 mg, 2.93 mmol) and 96% sulfuric acid (287.4 mg, 2.93 mmol) in water (8 ml) was added dropwise to a solution of Compound 11C and ruthenium chloride (2.76 mg, 0.0133 mmol) in MeCN (5 ml) at room temperature over 10 minutes. After the reaction solution was stirred at the same temperature for 5 minutes, ethyl acetate was added, the organic layer was separated, and the aqueous layer was extracted with ethyl acetate two times. The combined extracts were dried with sodium sulfate. The solvent was distilled off, and the resulting oil product was purified by subjecting it to silica gel column chromatography. From a fraction eluting n-hexane-ethyl acetate (1:1, v/v), 303.2 mg (yield 75%) of Compound 11D was obtained as an oil product.

$^1$H-NMR (CDCl$_3$) δ: 1.39 (3H, t, J=6.9 Hz), 4.40 (2H, q, J=6.9 Hz), 5.54 (2H, s), 7.37 (5H, s), 8.48 (1H, s), 9.85 (1H, s).

Fourth Step

A solution of 96% sulfuric acid (421.7 mg, 4.30 mmol) and amidosululic acid (642.7 mg, 6.62 mmol) in water (10 ml) was added to a solution of Compound 11D (1.00 g, 3.31 mmol) in MeCN (15 ml) at room temperature, the mixture was stirred, and a solution of sodium chlorite (388.9 mg, 4.30 mmol) in water (10 ml) was added dropwise over 5 minutes while the same temperature was retained. The reaction solution was stirred at same temperature for 5 minutes, and saturated sodium chloride water was added, followed by extraction with ethyl acetate three times. The combined extracts were dried with sodium sulfate. The solvent was distilled off, and the resulting oil product was purified by subjecting it to silica gel column chromatography. The column was eluted initially with chloroform and, then, chloroform-MeOH (7:3, v/v). When the objective fraction was concentrated, 748.8 mg (yield 71%) of Compound 11E was obtained as an oil product.

$^1$H-NMR (CDCl$_3$) δ: 1.40 (3H, t, J=7.2 Hz), 3.93 (1H, br s), 4.40 (2H, q, J=7.2 Hz), 5.61 (2H, s), 7.38-7.44 (10H, m), 8.52 (1H, s).

Fifth Step

WSC HCl (1.20 g, 6.28 mmol) and HOBt (551.6 mg, 4.08 mmol) were added to a solution of Compound 11E (1.00 g, 3.14 mmol) in DMF (10 ml) at room temperature, and the mixture was stirred at the same temperature for 90 minutes. The reaction solution was cooled to 0° C., and a solution of 2-methoxyethanamine (236.0 mg, 3.14 mmol) in DMF (2 ml) was added dropwise over 3 minutes. The reaction solution was stirred at the same temperature for 1 hour, and water was added, followed by extraction with ethyl acetate three times. The extract was washed with water three times, and dried with sodium sulfate. The solvent was distilled off, and the resulting oil product was subjected to silica gel chromatography to purify the oil product. The column was eluted initially with n-hexane-ethyl acetate (1:1, v/v) and, then, n-hexane-ethyl acetate (1:9, v/v). When the objective fraction is concentrated, 928.5 mg (yield 79%) of Compound 11F was obtained as an oil product.

$^1$H-NMR (CDCl$_3$) δ: 1.39 (3H, t, J=7.2 Hz), 3.29 (3H, s), 3.41 (2H, t, J=5.4 Hz), 3.47-3.53 (2H, m), 4.39 (2H, q, J=7.2 Hz), 5.44 (2H, s), 7.36 (3H, m), 7.44-7.47 (2H, m), 8.07 (1H, br s), 8.54 (1H, s).

Sixth Step

A solution of Compound 11F (500 mg, 1.33 mmol) and (S)-2-amino-3-phenylpropan-1-ol (604.2 mg, 4.0 mmol) in xylene (2 ml) was heated to 120° C., and the solution was stirred for 30 minutes. The reaction solution was cooled to room temperature, the solvent was distilled off, and the resulting oil product was subjected to silica gel chromatography to purify the oil product. The column was eluted initially with chloroform and, then, chloroform-MeOH (9:1, v/v). When the objective fraction was concentrated, 487 mg (yield 72%) of Compound 11G was obtained as an oil product.

$^1$H-NMR (CDCl$_3$) δ: 1.41 (3H, t, J=6.9 Hz), 2.24-2.34 (1H, m), 2.24-3.00 (1H, m), 3.03-3.16 (1H, m), 3.05 (3H, m), 3.25-3.32 (2H, m), 4.13-4.19 (1H, m), 4.17-4.30 (1H, m), 4.36-4.47 (1H, m), 4.51-4.54 (1H, m), 4.55 (1H, d, J=10.5 Hz), 5.78 (1H, t, J=6.9 Hz), 7.17-7.26 (4H, m), 7.28-7.35 (5H, m), 7.49 (1H, t, J=5.4 Hz), 6.32 (1H, s).

Seventh Step

A DEAD 40 wt % toluene solution (3.68 g, 8.45 mmol) was added dropwise to a solution of Compound 11G (2.86 g, 5.63 mmol) and triphenylphosphine (2.21 g, 8.45 mmol) in THF (6 ml) at room temperature over 3 minutes. The reaction solution was stirred at the same temperature for 30 minutes, the solvent was distilled off, and the resulting oil product was subjected to silica gel chromatography to purify the oil product. From a fraction eluting with ethyl acetate-MeOH (9:1, v/v), 1.37 g (yield 50%) of Compound 11H was obtained as an oil product.

$^1$H-NMR (CDCl$_3$) δ: 1.31 (3H, t, J=7.2 Hz), 3.07 (2H, d, J=6.9 Hz), 3.33 (3H, s), 3.57-3.80 (4H, m), 3.95 (1H, dd, J=3.0 Hz, 6.6 Hz), 4.01-4.14 (1H, m), 4.16-4.34 (2H, m), 5.24 (1H, d, J=9.9 Hz), 5.51 (1H, d, J=9.9 Hz), 7.01-7.03 (2H, m), 7.21-7.37 (5H, m), 7.41-7.58 (1H, m), 7.64-7.69 (2H, m).

Eighth Step

A 2N aqueous sodium hydroxide solution (6 ml) was added to a solution of Compound 11H (1.0 g, 2.04 mmol) in EtOH (6 ml), and the mixture was stirred at room temperature for 30 minutes. The reaction solution was neutralized with 2N hydrochloric acid, and the precipitated solid was filtered off, and dried to obtain 754 mg (yield 80%) of Compound 11I.

$^1$H-NMR (CDCl$_3$) δ: 3.10 (2H, d, J=7.8 Hz), 3.33 (3H, s), 3.57-3.69 (4H, m), 3.82-3.90 (1H, m), 3.95 (1H, dd, J=3.3 Hz, 13.8 Hz), 4.36 (1H, dd, J=6.3 Hz, 7.5 Hz), 5.36 (1H, d, J=10.2 Hz), 5.45 (1H, d, J=10.2 Hz), 6.98-7.01 (2H, m), 7.28-7.39 (6H, m), 7.59 (2H, dd, J=1.8 Hz, 8.1 Hz), 7.87 (1H, s).

Ninth Step

Compound 11I (1.0 g, 2.16 mmol) was dissolved in THF (10 ml), 10% Pd—C (200 mg) was added, and the mixture was subjected to a catalytic reduction reaction under a hydrogen stream. The catalyst was removed by filtration, and the filtrate was concentrated. The resulting residue was washed with ether to obtain 512 mg (yield 64%) of Compound 11.

$^1$H-NMR (CDCl$_3$) δ: 6.24 (2H, d, J=6.3 Hz), 3.36 (3H, s), 3.60-3.86 (5H, m), 4.14 (1H, d, J=12.9 Hz), 4.47 (1H, s), 7.03-7.05 (2H, m), 7.30-7.35 (3H, m), 7.88 (1H, s), 12.68 (1H, s), 14.83 (1H, s).

Example 12

[Chemical formula 75]

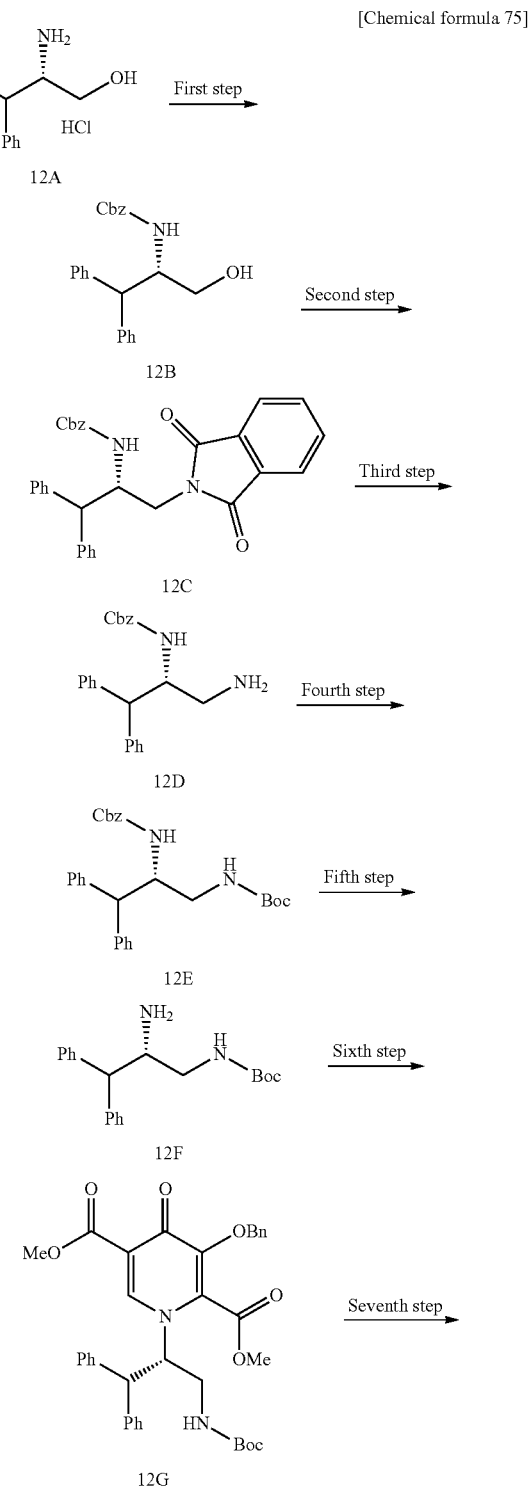

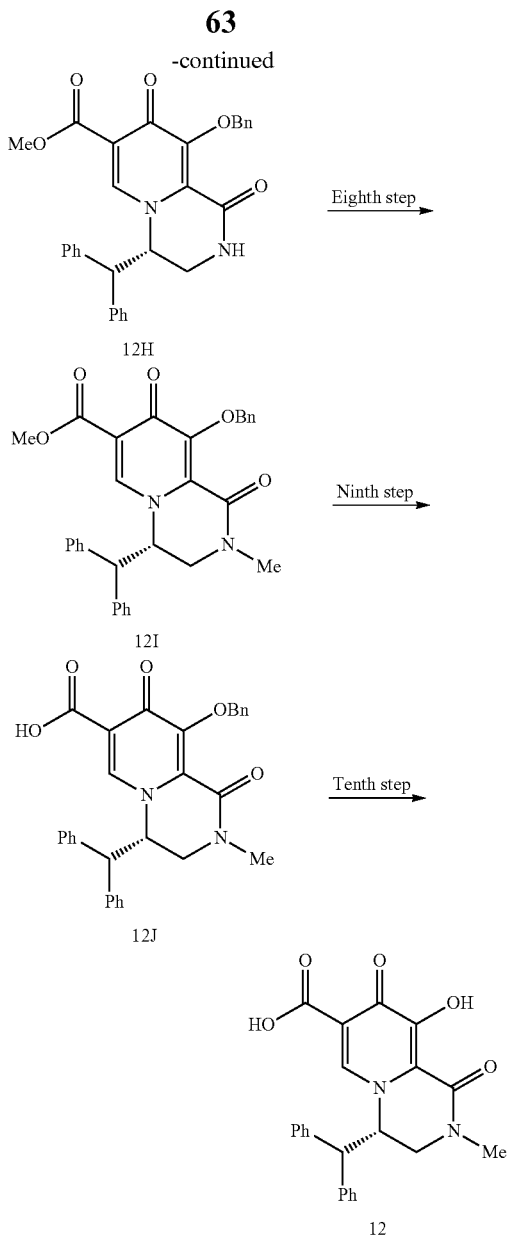

First Step

Compound 12A (1.53 g, 5.80 mmol) was dissolved in THF (6 ml) and water (6 ml), potassium carbonate (2.41 g, 17.4 mmol) was added, the mixture was stirred, and benzyl chloroformate (1.09 g, 6.38 mmol) was added dropwise at 0° C. After stirring at 0° C. for 10 minutes, the mixture was stirred at room temperature for 2 hours. The reaction solution was poured into an aqueous sodium bicarbonate solution, followed by extraction with ethyl acetate. The extract was washed with 1N hydrochloric acid and saturated sodium chloride water, and dried with sodium sulfate. The solvent was distilled off to obtain 2.32 g of Compound 12B as a colorless gummy substance.

$^1$H-NMR (CDCl$_3$) δ: 1.98 (1H, brs), 3.55 (1H, m), 3.75 (1H, m), 4.20 (1H, d, J=10.5 Hz), 4.58 (1H, m), 4.83 (1H, brs), 5.07 (2H, s), 7.16-7.39 (15H, m).

Second Step

Compound 12B (1.94 g, 5.37 mmol), triphenylphosphine (2.11 g, 8.05 mmol) and phthalimide (948 mg, 6.44 mmol) were added to THF (20 ml), and diisopropyl azodicarboxylate (2.2M in toluene, 3.66 ml, 8.05 mmol) was added dropwise at room temperature. After stirring at room temperature for 4 hours, the solvent was distilled off under reduced pressure. The resulting crude product was purified by silica gel column chromatography (n-hexane-ethyl acetate, 1:1, v/v) to obtain 2.39 g of Compound 12C as a colorless solid.

$^1$H-NMR (CDCl$_3$) δ: 3.73 (2H, m), 4.05 (1H, d, J=10.1 Hz), 4.70 (1H, d, J=9.6 Hz), 4.77 (2H, d, J=7.2 Hz) 5.02 (1H, m), 7.03-7.42 (15H, m), 7.68 (2H, dd, J=5.7, 2.1 Hz), 7.78 (2H, dd, J=5.7, 2.1 Hz).

Third Step

Compound 12C (2.39 g, 4.87 mmol) was added to THF (20 ml) and methanol (20 ml), hydrazine hydrate (4.88 g, 97.4 mmol) was added, and the mixture was stirred at 50° C. for 4 hours. The white precipitate was removed by filtration, followed by washing with methanol. The filtrate was distilled off under reduced pressure, and the resulting crude product was purified by amino column chromatography (chloroform-methanol, 99:1, v/v) to obtain 1.41 g of Compound 12D as a colorless solid.

$^1$H-NMR (CDCl$_3$) δ: 2.63 (1H, dd, J=13.2, 5.8 Hz), 2.86 (1H, d, J=9.9 Hz), 4.07 (1H, d, J=10.4 Hz), 4.53 (1H, m), 4.81 (1H, m), 5.00 (2H, d, 8.4 Hz), 7.20-7.36 (10H, m).

Fourth Step

Compound 12D (1.41 g, 3.91 mmol) was dissolved in THF (15 ml), and Boc$_2$O (896 mg, 4.11 mmol) was added at room temperature. After stirring for 1.5 hours, the solvent was concentrated under reduced pressure. The resulting crude product was purified by silica gel column chromatography (n-hexane-ethyl acetate, 1.1, v/v) to obtain 1.77 g of Compound 12E as a colorless solid.

$^1$H-NMR (CDCl$_3$) δ: 1.41 (9H, s), 3.23 (2H, brm), 3.97 (1H, d, J=9.8 Hz), 4.58-4.80 (3H, m), 5.00 (2H, d, J=9.8 Hz), 7.15-7.29 (10H, m).

Fifth Step

Compound 12E (1.73 g, 3.76 mmol) and palladium active carbon (10%, wet, 200 mg) were added to methanol (20 ml), and the mixture was stirred at room temperature for 1 hour under a hydrogen atmosphere. After filtration with Celite, the solvent was concentrated under reduced pressure to obtain 1.01 g of a colorless oily substance 12F.

$^1$H-NMR (CDCl$_3$) δ: 1.44 (9H, s), 2.82 (1H, m), 3.31 (1H, m), 3.73 (2H, d, J=6.9 Hz), 4.98 (1H, s), 7.18-7.39 (10H, m).

Sixth Step

Dimethyl 3-(benzyloxy)-4-oxo-4H-pyran-2,5-dicarboxylate (974 mg, 3.06 mmol) and 12F (999 mg, 3.06 mmol) were added to toluene (10 ml), and the mixture was stirred at 110° C. for 5 hours. After the solvent was distilled off under reduced pressure, the resulting crude product was purified by silica gel column chromatography (chloroform-methanol, 98:2, v/v) to obtain 1.51 g of Compound 12G as a pale yellow solid.

$^1$H-NMR (CDCl$_3$) δ: 1.36 (9H, s), 3.40 (1H, m), 3.53 (1H, m), 3.82 (3H, s), 3.91 (3H, s), 4.29 (1H, d, J=11.3 Hz), 4.78 (1H, m), 4.82 (1H, m), 5.11 (1.9H, d, J=7.5 Hz), 7.10-7.38 (10H, m), 8.27 (1H, s).

Seventh Step

To Compound 12G (1.45 g, 2.31 mmol) was added 4N HCl (ethyl acetate solution, 20 ml), and the mixture was stirred at room temperature for 1.5 hours. After the solvent was distilled off under reduced pressure, an aqueous saturated sodium bicarbonate solution was added, and the mixture was stirred at room temperature for 1.5 hours. This was extracted with chloroform, and dried with sodium sulfate. After the solvent was distilled off under reduced pressure, the resulting crude product was purified by silica gel column chromatography (chloroform-methanol, 95.5, v/v) to obtain 1.01 g of Compound 12H as a colorless solid.

$^1$H-NMR (CDCl$_3$) δ: 3.40 (1H, dd, J=13.6, 6.6 Hz), 3.78 (3H, s), 3.80 (1H, m), 4.37 (1H, d, J=11.6 Hz), 4.59 (1H, d, J=11.0 Hz), 5.43 (2H, d, J=10.2 Hz), 5.93 (1H, d, J=5.8 Hz), 7.03-7.21 (5H, m), 7.37 (9H, m), 7.63 (2H, m).

Eighth Step

Compound 12H (50 mg, 0.10 mmol) was dissolved in DMF (1 ml), and cesium carbonate (165 mg, 0.50 mmol) was added. After stirring at room temperature for 30 minutes, iodomethane (0.032 ml, 0.50 mmol) was added, and the mixture was stirred at room temperature for 3.5 hours. The reaction solution was poured into water, and this was extracted with ethyl acetate, and dried with sodium sulfate. After the solvent was distilled off under reduced pressure, the resulting crude product was purified by silica gel column chromatography (chloroform-methanol, 95:5, v/v) to obtain 49 mg of Compound 12I as a colorless solid.

Ninth Step

Compound 12I (49 mg, 0.096 mmol) was dissolved in THF (0.5 ml) and methanol (0.5 ml), a 2N aqueous sodium hydroxide solution (0.24 ml, 0.48 mmol) was added at room temperature, and this was stirred as it was for 1.5 hours. 1N hydrochloric acid was added, and this was extracted with ethyl acetate, and dried with sodium sulfate. After the solvent was distilled off under reduced pressure, 54 mg of Compound 12J was obtained as a colorless solid.

MS: m/z=481 [M+H]$^+$.

Tenth Step

Trifluoroacetic acid (1 ml) was added to Compound 12J obtained in Ninth step, and mixture was stirred at room temperature for 1 hour. After concentration under reduced pressure, an aqueous sodium bicarbonate solution and 2N hydrochloric acid were used to adjust a pH to 3, and this was extracted with chloroform, and dried with sodium sulfate. After the solvent was distilled off under reduced pressure, chloroform-methanol-ethyl ether were added, and the precipitated solid was filtered off to obtain 26 mg of Compound 12 as a colorless solid.

$^1$H-NMR (DMSO-d6) δ: 3.01 (3H, s), 3.26 (1H, t, J=14.4 Hz), 4.23 (1H, dd, J=13.5, 3.8 Hz), 4.57 (1H, d, J=11.6 Hz), 5.78 (1H, d, J=11.3 Hz), 7.16-7.70 (10H, m), 8.00 (1H, s), 13.00 (1H, s), 15.10 (1H, s).

MS: m/z=405 [M+H]$^+$.

Example 13

[Chemical formula 76]

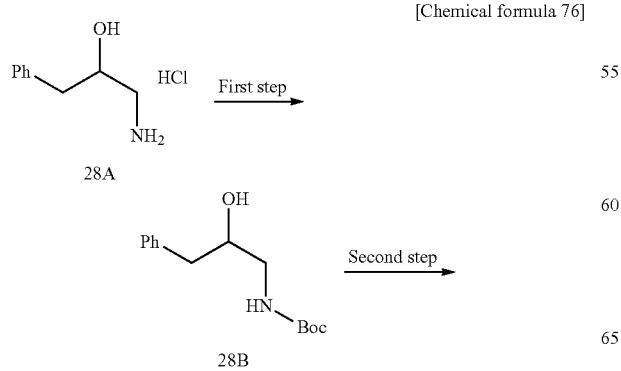

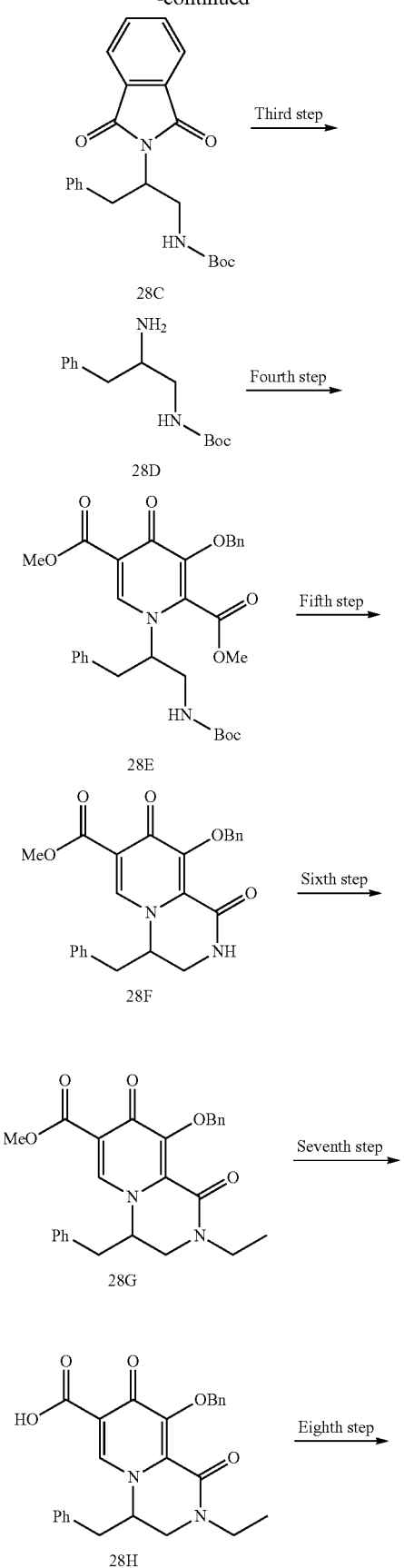

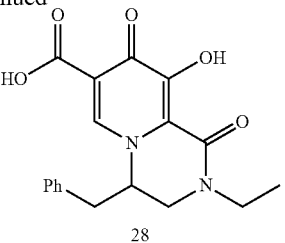

28

First Step

Compound 28A (3.20 g, 17.1 mmol) was added to THF (20 ml), triethylamine (2.60 ml, 18.8 mmol) was added, and the mixture was stirred at room temperature for 10 minutes. Boc$_2$O (4.09 g, 18.8 mmol) was added at room temperature, and the mixture was stirred as it was for 2 hours. The solvent was distilled off under reduced pressure, and water was added, followed by extraction with ethyl acetate. The organic layer was washed with saturated sodium chloride water, and dried with sodium sulfate. The solvent was distilled off under reduced pressure to obtain 5.17 g of Compound 28b as a colorless solid.

$^1$H-NMR (CDCl$_3$) δ: 1.52 (9H, s), 2.77 (2H, m), 3.03-3.12 (1H, m), 3.38 (1H, m), 3.90-3.98 (1H, m), 4.93 (1H, brs), 7.20-7.35 (5H, m).

Second Step

Compound 28B (4.29 g, 17.1 mmol), triphenylphosphine (5.37 g, 20.5 mmol) and phthalimide (2.76 g, 18.8 mmol) were added to THF (60 ml), and diethyl azodicarboxylate (2.2M in toluene, 11.6 ml, 25.6 mmol) was added dropwise at room temperature. After stirring at room temperature for 1 hour, the solvent was distilled off under reduced pressure. The resulting crude product was purified by silica gel column chromatography (n-hexane-ethyl acetate, 2:1, v/v) to obtain 6.13 g of Compound 28C as a colorless solid.

$^1$H-NMR (CDCl$_3$) δ: 1.30 (9H, s), 3.14 (1H, dd, J=13.8, 6.2 Hz), 3.39 (2H, m), 3.87 (1H, m), 4.67 (1H, m), 4.81 (1H, brs), 7.16-7.19 (5H, m), 7.66 (2H, dd, J=5.3, 3.1 Hz), 7.75 (2H, dd, J=5.7, 3.0 Hz).

Third Step

Compound 28C (1.00 g, 2.63 mmol) was added to THF (7 ml) and methanol (7 ml), hydrazine hydrate (2.63 g, 52.6 mmol) was added, and the mixture was stirred at 50° C. for 2 hours. The white precipitate was removed by filtration, followed by washing with methanol. After the filtrate was distilled off under reduced pressure, the resulting crude product was purified by amino column chromatography (chloroform-methanol, 99:1, v/v) to obtain 249 mg of Compound 28D as a colorless solid.

$^1$H-NMR (CDCl$_3$) δ: 1.44 (9H, s), 1.95 (2H, brs), 2.55-3.31 (5H, m), 5.06 (1H, brs), 7.18-7.33 (5H, m).

Fourth Step

Dimethyl 3-(benzyloxy)-4-oxo-4H-pyran-2,5-dicarboxylate (313 mg, 0.983 mmol) and 28D (246 mg, 0.983 mmol) were added to toluene (3 ml), and the mixture was stirred at 100° C. for 2.5 hours. After the solvent was distilled off under reduced pressure, the resulting crude product was purified by silica gel column chromatography (chloroform-methanol, 98.2, v/v) to obtain 320 mg of Compound 28E as a pale yellow gummy substance.

$^1$H-NMR (CDCl$_3$) δ: 1.42 (9H, s), 3.07 (2H, m), 3.56 (2H, m), 3.68 (3H, s), 3.95 (3H, s), 4.26 (1H, m), 4.86 (1H, s), 5.18 (1H, d, J=10.8 Hz), 5.22 (1H, d, J=10.8 Hz), 7.01 (2H, m), 7.24-7.38 (8H, m), 8.22 (1H, s).

MS: m/z=551 [M+H]$^+$.

Fifth Step

To Compound 28E (315 mg, 0.572 mmol) was added to 4N HCl (ethyl acetate solution, 5 ml), and the mixture was stirred at room temperature for 30 minutes. The solvent was distilled off under reduced pressure, an aqueous saturated sodium bicarbonate solution was added, and this was extracted with chloroform, and dried with sodium sulfate. After the solvent was distilled off under reduced pressure, the resulting crude product was purified by silica gel column chromatography (chloroform-methanol, 95:5, v/v) to obtain 210 mg of Compound 28F as a colorless solid.

$^1$H-NMR (CDCl$_3$) δ: 3.07-3.15 (2H, m), 3.34 (1H, dd, J=13.2, 6.0 Hz), 3.74 (2H, m), 3.86 (3H, s), 4.12 (1H, m), 5.27 (1H, d, J=10.1 Hz), 5.47 (1H, d, J=10.1 Hz), 6.76 (1H, d, J=6.4 Hz), 7.04 (2H, m), 7.32 (6H, m), 7.62 (2H, dd, J=7.7, 1.4 Hz), 7.70 (1H, s).

MS: m/z=419 [M+H]$^+$.

Sixth Step

Compound 28F (50 mg, 0.12 mmol) was dissolved in DMF (1 ml), and cesium carbonate (195 mg, 0.597 mmol) was added. After stirring at room temperature for 30 minutes, iodoethane (0.048 ml, 0.60 mmol) was added, and the mixture was stirred at room temperature for 3.5 hours. The reaction solution was poured into water, and this was extracted with ethyl acetate, and dried with sodium sulfate. After the solvent was distilled off under reduced pressure, the resulting crude product was purified by silica gel column chromatography (chloroform-methanol, 95:5, v/v) to obtain 47 mg of Compound 28G as a colorless solid.

$^1$H-NMR (CDCl$_3$) δ: 1.22 (3H, t, J=7.2 Hz), 3.00-3.15 (2H, m), 3.28 (1H, dd, J=13.6, 1.6 Hz), 3.48 (1H, m), 3.75 (1H, m), 3.85 (3H, s), 3.88 (1H, dd, J=13.3, 3.2 Hz), 4.15 (1H, m), 5.25 (1H, d, J=9.9 Hz), 5.50 (1H, d, J=9.9 Hz), 7.04 (2H, m), 7.29-7.38 (6H, m), 7.60 (1H, s), 7.68 (2H, m).

MS: m/z=447 [M+H]$^+$.

Seventh Step

Compound 28G (47 mg, 0.11 mmol) was dissolved in THF (0.5 ml) and methanol (0.5 ml), a 2N aqueous sodium hydroxide solution (0.26 ml, 0.53 mmol) was added at room temperature, and the mixture was stirred as it was for 1 hour. 1N hydrochloric acid was added, and this was extracted with ethyl acetate, and dried with sodium sulfate. The solvent was distilled off under reduced pressure to obtain 40 mg of Compound 28H as a colorless solid.

MS: m/z=433 [M+H]$^+$.

Eighth Step

Trifluoroacetic acid (1 ml) was added to Compound 28H obtained in Seventh step, and the mixture was stirred at room temperature for 1 hour. After concentration under reduced pressure, a pH was adjusted to 3 with an aqueous sodium bicarbonate solution and 2N hydrochloric acid, and this was extracted with chloroform, and dried with sodium sulfate. After the solvent was distilled off under reduced pressure, chloroform-methanol-ethyl ether were added, and the precipitated solid was filtered off to obtain 17 mg of Compound 28 as a colorless solid.

$^1$H-NMR (DMSO-d6) δ: 1.17 (3H, t, J=7.2 Hz), 3.08 (2H, m), 3.51-3.63 (3H, m), 4.08 (1H, dd, J=13.6, 3.9 Hz), 5.03 (1H, brs), 7.21 (5H, m), 8.07 (1H, s), 12.98 (1H, s), 15.07 (1H, brs).

MS: m/z=343 [M+H]$^+$.

Example 14

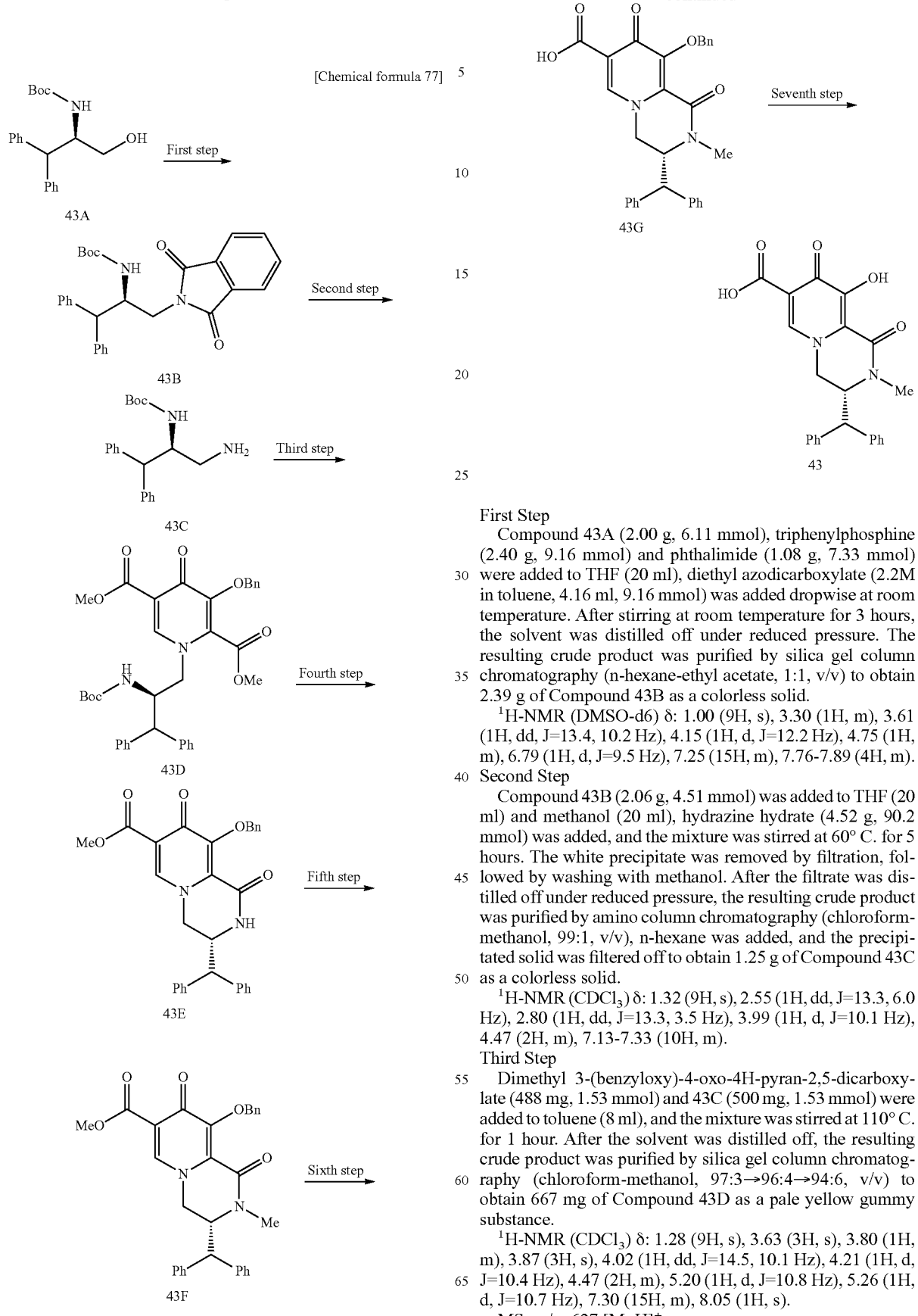

First Step

Compound 43A (2.00 g, 6.11 mmol), triphenylphosphine (2.40 g, 9.16 mmol) and phthalimide (1.08 g, 7.33 mmol) were added to THF (20 ml), diethyl azodicarboxylate (2.2M in toluene, 4.16 ml, 9.16 mmol) was added dropwise at room temperature. After stirring at room temperature for 3 hours, the solvent was distilled off under reduced pressure. The resulting crude product was purified by silica gel column chromatography (n-hexane-ethyl acetate, 1:1, v/v) to obtain 2.39 g of Compound 43B as a colorless solid.

$^1$H-NMR (DMSO-d6) δ: 1.00 (9H, s), 3.30 (1H, m), 3.61 (1H, dd, J=13.4, 10.2 Hz), 4.15 (1H, d, J=12.2 Hz), 4.75 (1H, m), 6.79 (1H, d, J=9.5 Hz), 7.25 (15H, m), 7.76-7.89 (4H, m).

Second Step

Compound 43B (2.06 g, 4.51 mmol) was added to THF (20 ml) and methanol (20 ml), hydrazine hydrate (4.52 g, 90.2 mmol) was added, and the mixture was stirred at 60° C. for 5 hours. The white precipitate was removed by filtration, followed by washing with methanol. After the filtrate was distilled off under reduced pressure, the resulting crude product was purified by amino column chromatography (chloroform-methanol, 99:1, v/v), n-hexane was added, and the precipitated solid was filtered off to obtain 1.25 g of Compound 43C as a colorless solid.

$^1$H-NMR (CDCl$_3$) δ: 1.32 (9H, s), 2.55 (1H, dd, J=13.3, 6.0 Hz), 2.80 (1H, dd, J=13.3, 3.5 Hz), 3.99 (1H, d, J=10.1 Hz), 4.47 (2H, m), 7.13-7.33 (10H, m).

Third Step

Dimethyl 3-(benzyloxy)-4-oxo-4H-pyran-2,5-dicarboxylate (488 mg, 1.53 mmol) and 43C (500 mg, 1.53 mmol) were added to toluene (8 ml), and the mixture was stirred at 110° C. for 1 hour. After the solvent was distilled off, the resulting crude product was purified by silica gel column chromatography (chloroform-methanol, 97:3→96:4→94:6, v/v) to obtain 667 mg of Compound 43D as a pale yellow gummy substance.

$^1$H-NMR (CDCl$_3$) δ: 1.28 (9H, s), 3.63 (3H, s), 3.80 (1H, m), 3.87 (3H, s), 4.02 (1H, dd, J=14.5, 10.1 Hz), 4.21 (1H, d, J=10.4 Hz), 4.47 (2H, m), 5.20 (1H, d, J=10.8 Hz), 5.26 (1H, d, J=10.7 Hz), 7.30 (15H, m), 8.05 (1H, s).

MS: m/z=627 [M+H]$^+$.

Fourth Step

To Compound 43D (664 mg, 1.06 mmol) was added 4N HCl (ethyl acetate solution, 10 ml), and the mixture was stirred at room temperature for 1 hour. After the solvent was distilled off under reduced pressure, THF and an aqueous saturated sodium bicarbonate solution were added, and the mixture was stirred for 2.5 hours. This was extracted with chloroform, and dried with sodium sulfate. After the solvent was distilled off under reduced pressure, methylene chloride-ethyl ether were added, and the precipitated solid was filtered off to obtain 458 mg of Compound 43E as a colorless solid.

$^1$H-NMR (CDCl$_3$) δ: 3.86 (3H, m), 3.92 (3H, s), 4.41-4.48 (1H, m), 5.32 (1H, d, J=10.8 Hz), 5.42 (1H, d, J=10.1 Hz), 5.92 (1H, s), 7.21-7.39 (13H, m), 7.59 (2H, m), 7.89 (1H, s).

MS: m/z=495 [M+H]$^+$.

Fifth Step

Compound 43E (50 mg, 0.10 mmol) was dissolved in DMF (1 ml), and cesium carbonate (165 mg, 0.51 mmol) was added. After stirring at room temperature for 30 minutes, iodomethane (0.025 ml, 0.40 mmol) was added, and the mixture was stirred at room temperature for 1 hour. The reaction solution was poured into water, and this was extracted with ethyl acetate, and dried with sodium sulfate. After the solvent was distilled off under reduced pressure, the resulting crude product was purified by silica gel column chromatography (chloroform-methanol, 97:3→95:5, v/v) to obtain 60 mg of Compound 43F as a colorless solid.

$^1$H-NMR (CDCl$_3$) δ: 2.57 (3H, s), 3.75 (2H, d, J=11.3 Hz), 3.93 (3H, s), 4.20-4.29 (2H, m), 5.25 (1H, d, J=9.9 Hz), 5.57 (1H, d, J=9.9 Hz), 7.15-7.41 (13H, m), 7.63 (1H, s), 7.72-7.76 (2H, m).

Sixth Step

Compound 43F obtained in Fifth step was dissolved in THF (0.5 ml) and methanol (0.5 ml), a 2N aqueous sodium hydroxide solution (0.25 ml, 0.50 mmol) was added at room temperature, and the mixture was stirred as it was for 1 hour. 1N hydrochloric acid was added, and this was extracted with ethyl acetate, and dried with sodium sulfate. After the solvent was distilled off under reduced pressure, Compound 43G was obtained as a colorless gummy substance.

Seventh Step

Trifluoroacetic acid (2 ml) was added to Compound 43G obtained in Sixth step, and the mixture was stirred at room temperature for 1 hour. After concentration under reduced pressure, a pH was adjusted to 3 with an aqueous sodium bicarbonate solution and 2N hydrochloric acid, and this was extracted with chloroform, and dried with sodium sulfate. After the solvent was distilled off under reduced pressure, chloroform-ethyl ether were added, and the precipitated solid was filtered off to obtain 27 mg of Compound 43 as a colorless solid.

$^1$H-NMR (DMSO-d6) δ: 2.53 (3H, s), 4.26 (1H, d, J=10.9 Hz), 4.35 (1H, d, J=13.3 Hz), 4.58 (1H, dd, J=13.8, 3.5 Hz), 5.06 (1H, d, J=10.9 Hz), 7.36 (10H, m), 8.36 (1H, s), 12.58 (1H, s), 15.62 (1H, s).

MS: m/z=405 [M+H]$^+$.

Example 15

[Chemical formula 78]

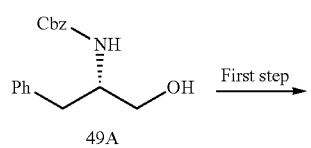
49A

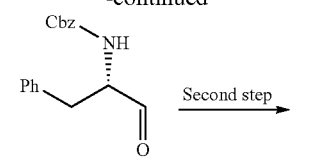
49B

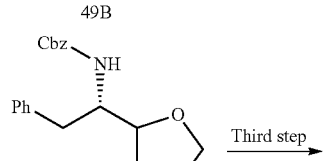
49C

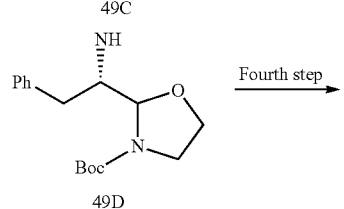
49D

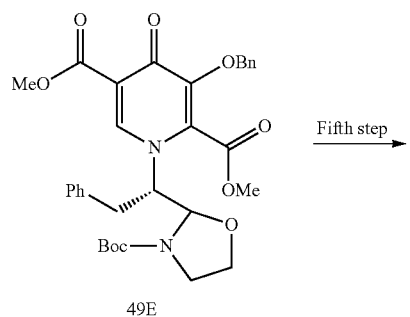
49E

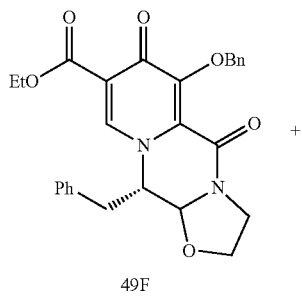
49F

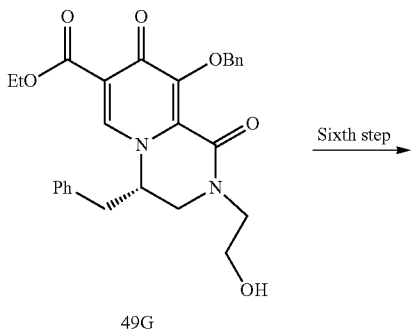
49G

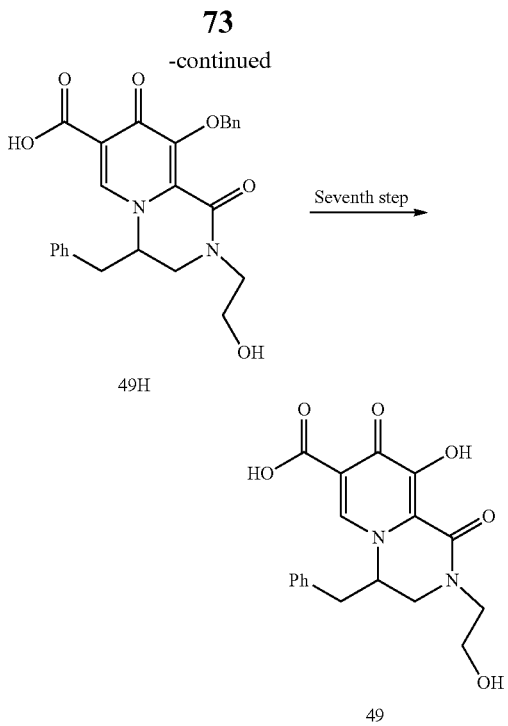

49H

49

First Step

A solution of Compound 49A (2.97 g, 10.4 mmol) in methylene chloride (20 ml) was added dropwise to Dess-Martin Periodinane (0.3M, methylene chloride solution, 52.0 ml, 15.6 mmol) at 0° C. After stirring at room temperature for 3 hours, this was poured into a 1N aqueous sodium hydroxide solution, followed by extraction with ethyl ether. The organic layer was washed with a 1N aqueous sodium hydroxide solution and saturated sodium chloride water, and dried with magnesium sulfate. After the solvent was distilled off under reduced pressure, 2.08 g of Compound 49B was obtained as a white solid.

$^1$H-NMR (CDCl$_3$) δ: 3.13 (2H, d, J=6.6 Hz), 4.53 (1H, q, J=6.7 Hz), 5.12 (2H, s), 5.28 (1H, brs), 7.26 (10H, m), 9.64 (1H, s).

Second Step

Compound 49B (700 mg, 2.47 mmol), 2-aminoethanol (166 mg, 2.72 mmol) and sodium sulfate (1.76 g, 12.4 mmol) were added to toluene (20 ml), and the mixture was stirred at room temperature for 1 hour. Boc$_2$O (0.631 ml, 2.72 mmol) was added at room temperature, and the mixture was stirred as it was for 18 hours. The reaction solution was filtered, and the filtrate was concentrated under reduced pressure. The resulting crude product was purified by silica gel column chromatography (n-hexane-ethyl acetate, 1:1, v/v) to obtain 893 mg of 49C as a colorless gummy substance.

Third Step

Compound 49C (890 mg, 2.09 mmol) and palladium-active carbon (10%, wet, 200 mg) were added to ethanol (20 ml), and the mixture was stirred at room temperature for 2 hours. After filtration with Celite, the solvent was concentrated under reduced pressure to obtain 656 mg of 49D as a colorless oily substance.

$^1$H-NMR (CDCl$_3$) δ: 1.40 (9H, s), 2.65-2.86 (2H, m), 3.32 (2H, m), 3.80 (2H, m), 4.03-4.12 (1H, m), 4.86 (1H, brs), 7.22 (5H, m).

Fourth Step

Dimethyl 3-(benzyloxy)-4-oxo-4H-pyran-2,5-dicarboxylate (610 mg, 2.09 mmol) and 49D (664 mg, 2.09 mmol) were added to toluene (6 ml), and the mixture was stirred at 100° C. for 4 hours. After the solvent was distilled off under reduced pressure, the resulting crude product was purified by silica gel column chromatography (n-hexane-ethyl acetate, 1:1, v/v) to obtain 884 mg of Compound 49E as a pale yellow gummy substance.

MS: m/z=593 [M+H]$^+$.

Fifth Step

To Compound 49E (860 mg, 1.45 mmol) was added 4N HCl (ethyl acetate solution, 10 ml). After stirring at room temperature for 30 minutes, the solvent was distilled off under reduced pressure. Subsequently, toluene (10 ml) and 2-aminoethanol (0.175 ml, 2.90 mmol) were added, and the mixture was stirred at 80° C. for 30 minutes. After the solvent was distilled off under reduced pressure, the resulting crude product was purified by silica gel column chromatography (chloroform-methanol, 99:1→95:5→90:10, v/v) to obtain 157 mg of Compound 49F as a colorless gummy substance and 217 mg of Compound 49G as a yellow solid.

49F: $^1$H-NMR (CDCl$_3$) δ: 2.48 (1H, dd, J=14.0, 11.4 Hz), 3.22 (1H, dd, J=14.1, 3.3 Hz), 3.69 (1H, m), 3.77 (3H, s), 3.83-3.95 (1H, m), 4.08 (1H, m), 4.29 (1H, m), 4.41 (1H, m), 5.34 (2H, m), 5.48 (1H, d, J=10.1 Hz), 6.86 (2H, m), 7.20-7.39 (7H, m), 7.64 (2H, m)

49G: $^1$H-NMR (DMSO-d6) δ: 3.70 (2H, t, J=5.3 Hz), 3.73 (3H, s), 3.86 (2H, t, J=5.3 Hz), 4.14 (2H, s), 4.98 (1H, t, J=5.0 Hz), 5.06 (2H, s), 6.98 (1H, s), 7.35 (8H, m), 7.62 (2H, d, J=7.1 Hz), 8.34 (1H, d, J=0.8 Hz).

Sixth Step

Compound 49G (214 mg, 0.465 mmol) was dissolved in THF (4 ml), ethanol (2 ml) and methylene chloride (2 ml), a 2N aqueous sodium hydroxide solution (1.16 ml, 2.32 mmol) was added at room temperature, and the mixture was stirred as it was for 2.5 hours. 1N hydrochloric acid was added, and this was extracted with chloroform, and dried with sodium sulfate. The solvent was distilled off under reduced pressure to obtain 158 mg of Compound 49H as a yellow solid.

$^1$H-NMR (DMSO-d6) δ: 3.70 (2H, q, J=5.2 Hz), 3.89 (2H, t, J=5.3 Hz), 4.22 (2H, s), 4.97 (1H, t, J=5.6 Hz), 5.12 (2H, s), 7.23-7.41 (9H, m), 7.60 (2H, m), 8.54 (1H, s).

Seventh Step

Compound 49H (50.0 mg, 0.112 mmol) and palladium-active carbon (10%, wet, 12 mg) were added to methanol (1 ml) and DMF (3 ml), and the mixture was stirred at room temperature for 5 hours under a hydrogen atmosphere. After filtration with Celite, the solvent was concentrated under reduced pressure. Chloroform-methanol-ethyl ether were added, and the precipitated solid was filtered off to obtain 9.0 mg of Compound 49 as a colorless solid.

$^1$H-NMR (DMSO-d6) δ: 3.10 (2H, m), 3.51-3.69 (4H, m), 4.10 (1H, d, J=10.7 Hz), 4.94 (2H, m), 7.11-7.26 (5H, m), 8.03 (1H, s), 12.94 (1H, brs), 15.30 (1H, brs).

MS: m/z=359 [M+H]$^+$.

Example 16

[Chemical formula 79]

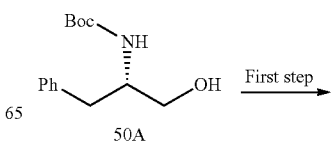

50A

First step

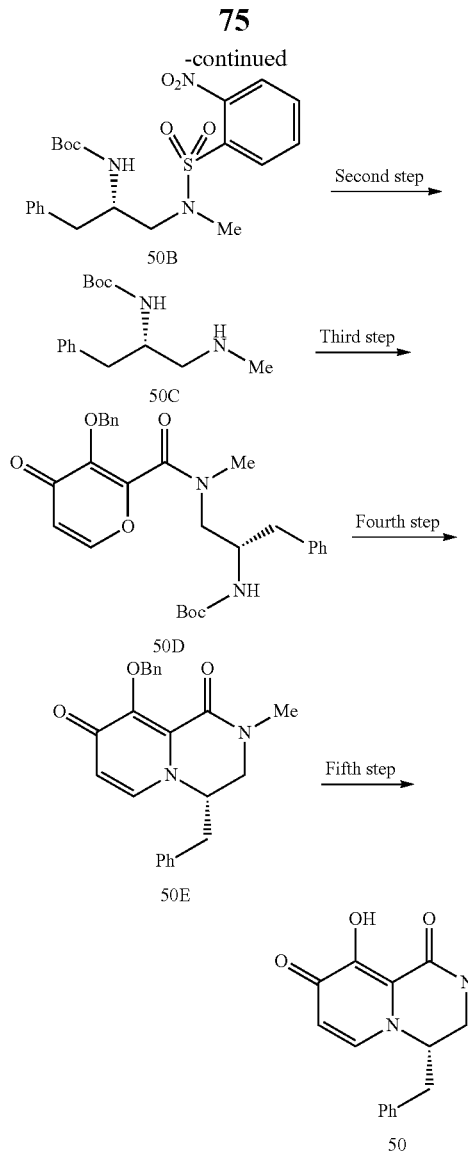

First Step

Compound 50A (1.00 g, 3.98 mmol), triphenylphosphine (1.15 g, 4.48 mmol) and N-methyl-2-nitrobenzenesulfonamide (860 mg, 3.98 mmol) were added to THF (10 ml), and diethyl azodicarboxylate (2.2M in toluene, 1.99 ml, 4.38 mmol) was added dropwise at room temperature. After stirring at room temperature for 3 hours, the solvent was distilled off under reduced pressure. The resulting crude product was purified by silica gel column chromatography (n-hexane-ethyl acetate, 1:1, v/v) to obtain 710 mg of Compound 50B as a colorless gummy substance.

Second Step

Compound 50B (458 mg, 1.02 mmol) was dissolved in acetonitrile, potassium carbonate (422 mg, 3.06 mmol) and benzenethiol (0.126 ml, 1.22 mmol) were added, and the mixture was stirred at room temperature for 5 hours. The reaction solution was poured into a 1N aqueous sodium hydroxide solution, and this was extracted with methylene chloride, and dried with sodium sulfate. The resulting crude product was purified by amino column chromatography (chloroform-methanol, 95:5, v/v) to obtain 147 mg of Compound 50C as a colorless oily substance.

$^1$H-NMR (CDCl$_3$) δ: 1.36 (9H, s), 2.40 (3H, s), 2.51-2.89 (4H, m), 3.90 (1H, s), 4.69 (1H, s), 7.17-7.31 (5H, m).

Third Step

Compound 50C (140 mg, 0.530 mmol) and 3-(benzyloxy)-4-oxo-4H-pyran-2-carboxylic acid (WO 2006/116764, 119 mg, 0.482 mmol) were added to THF (3 ml), 1-(3-dimethylaminopropyl)-3-ethylcarbodiimide hydrochloride (111 mg, 0.578 mmol) and 1-hydroxybenzotriazole (65.1 mg, 0.482 mmol) were added, and the mixture was stirred at room temperature for 18 hours. The reaction solution was poured into an aqueous sodium bicarbonate solution, and this was extracted with ethyl acetate, and dried with sodium sulfate. The resulting crude product was purified by silica gel column chromatography (chloroform-methanol, 97:3, v/v) to obtain 219 mg of Compound 50D as a colorless solid.

MS: m/z=493 [M+H]$^+$.

Fourth Step

To Compound 50D (216 mg, 0.439 mmol) was added 4N HCl (ethyl acetate solution, 3 ml). After the mixture was stirred at room temperature for 1 hour, the solvent was distilled off under reduced pressure. Subsequently, ethanol (4 ml) and an aqueous saturated sodium carbonate solution (3 ml) were added, and mixture was stirred at 60° C. for 2 hours. Water was added, and this was extracted with ethyl acetate, and dried with sodium sulfate. The resulting crude product was purified by amino column chromatography (chloroform-methanol, 95:5, v/v) to obtain 108 mg of Compound 50E as a pale yellow gummy substance.

$^1$H-NMR (CDCl$_3$) δ: 3.00 (2H, m), 3.13 (3H, s), 3.18 (1H, m), 3.88 (1H, dd, J=13.5, 3.4 Hz), 4.00-4.07 (1H, m), 5.26 (1H, d, J=10.2 Hz), 5.46 (1H, d, J=10.1 Hz), 6.25 (1H, d, J=7.5 Hz), 6.73 (1H, d, J=7.5 Hz), 6.99-7.02 (2H, m), 7.28-7.37 (6H, m), 7.63-7.67 (2H, m).

Fifth Step

Trifluoroacetic acid (2 ml) was added to Compound 50E (105 mg, 0.280 mmol), and the mixture was stirred at room temperature for 30 minutes. After concentration under reduced pressure, a pH was adjusted to 6 with an aqueous sodium bicarbonate solution and 2N hydrochloric acid, and this was extracted with chloroform, and dried with sodium sulfate. After the solvent was distilled off under reduced pressure, methylene chloride-methanol-ethyl ether were added, and the precipitated solid was filtered off to obtain 29 mg of Compound 50 as a colorless solid.

$^1$H-NMR (DMSO-d6) δ: 2.99 (3H, s), 3.26-3.47 (3H, m), 4.07 (1H, d, J=11.1 Hz), 4.80 (1H, m), 6.43 (1H, d, J=6.9 Hz), 7.11-7.29 (5H, m), 7.50 (1H, d, J=6.9 Hz).

MS: m/z=285 [M+H]$^+$.

Example 17

[Chemical formula 80]

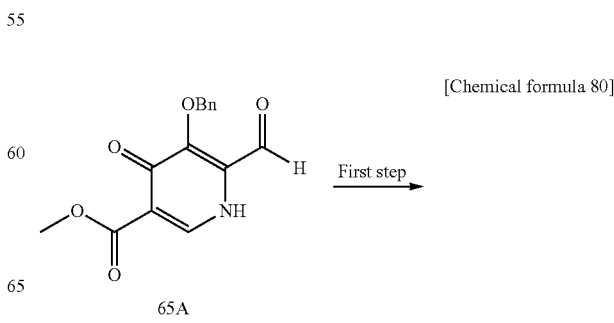

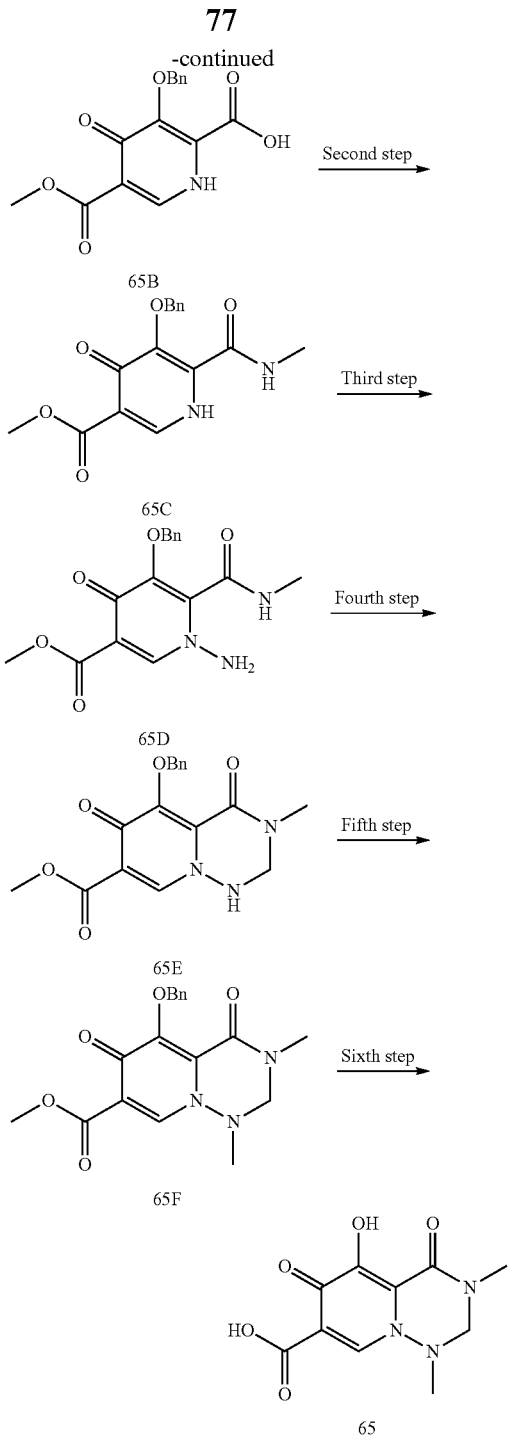

First Step

A solution of Compound 65A (WO 2006/088173, 20.0 g, 69.6 mmol) in THF (1.1 L) was retained at 25° C. on a water bath, and a solution of sodium chlorite (25.2 g, 278 mmol) and amidosulfuric acid (27.0 g, 278 mmol) in water (378 mL) was added dropwise over 30 minutes. The reaction solution was stirred at the same temperature for 1 hour, and concentrated under reduced pressure. To the residue were added ice water (100 mL) and diethyl ether (100 mL), and the precipitated solid was filtered. The resulting crude purified product was washed with water and diethyl ether to obtain 20.3 g of Compound 65B as a white solid.

$^1$H-NMR (DMSO-d6) δ: 3.74 (3H, s), 5.11 (2H, s), 7.31-7.38 (3H, m), 7.48 (2H, d, J=7.2 Hz), 8.11 (1H, s), 12.07 (1H, brs).

Second Step

Compound 65B (2.0 g, 6.59 mmol) was dissolved in DMF (340 mL), and HATU (2.76 g, 7.25 mmol), methylamine (2 mol/L THF solution, 3.63 mL, 7.25 mmol), and triethylamine (9.89 mmol) were added, and the mixture was stirred at room temperature for 5 hours. The reaction solution was dispensed to ethyl acetate and water. The ethyl acetate layer was separated, and the aqueous layer was extracted with ethyl acetate once. The combined extracts were washed with water and saturated sodium chloride water, and dried. The solvent was distilled off to obtain 1.66 g of a crude purified product of Compound 65C as a white solid.

$^1$H-NMR (DMSO-d6) δ: 3.38 (3H, brs), 3.75 (3H, s), 5.37 (2H, s), 7.34-7.44 (5H, m), 8.10 (1H, s), 8.38 (1H, s), 11.84 (1H, brs).

Third Step

Potassium carbonate (1.04 g, 7.59 mmol) and O-(2,4-dinitrophenyl)hydroxylamine (831 mg, 4.17 mmol) were added to a solution of Compound 65C (1.2 g, 3.79 mmol) in DMF (20 mL), and the mixture was stirred at room temperature for 3 hours. Water was added to the reaction solution, and the precipitated solid was filtered off and washed with water to obtain 1.0 g of a crude purified product of Compound 65D.

$^1$H-NMR (DMSO-d6) δ: 3.74 (3H, s), 3.83 (3H, brs), 5.05 (2H, s), 6.46 (2H, brs), 7.31-7.38 (5H, m), 8.20 (1H, s), 8.52 (1H, brs).

Fourth Step

Paraformaldehyde (109 mg, 3.62 mmol) and acetic acid (0.017 ml, 0.302 mmol) were added to a solution of Compound 65D (1.0 g, 3.02 mmol) in DMF (10 mL) at room temperature, and the mixture was stirred at 105° C. for 2 hours. The reaction solution was cooled to 0° C., cesium carbonate (3.44 g, 10.6 mmol) was added, and the mixture was stirred at room temperature for 1 hour. Water was added to the reaction solution, and this was dispensed to ethyl acetate and water. The organic layer was washed with saturated sodium chloride water, and dried. The solvent was distilled off to obtain 120 mg of Compound 65E.

MS: m/z=344 [M+H]$^+$.

Fifth Step

Cesium carbonate (81.4 mg, 0.25 mmol) and methylamine (2 mol/L THF solution, 0.125 ml, 0.25 mmol) were added to a solution of Compound 65E (17.0 mg, 0.05 mmol) in DMF (1 mL), and the mixture was stirred at room temperature for 5 hours. The reaction solution was filtered, and the filtrate was taken and purified by LCMS to obtain Compound 65F.

MS: m/z=358 [M+H]$^+$.

Sixth Step

A 2N aqueous sodium hydroxide solution (0.2 mL) was added to a solution of Compound 65F in DMF (0.5 mL), and the mixture was stirred at room temperature for 2 hours Ion-exchange resin DOWEX (50W-X8) was added to the reaction solution, and this was filtered, and washed with DMF. After the filtrate was concentrated, trifluoroacetic acid (0.5 mL) was added, and the mixture was stirred at 80° C. for 4 hours. After the reaction solution was concentrated, water and chloroform were added, and the organic layer was separated. The organic layer was concentrated, and taken and purified by LCMS to obtain 6.47 mg of Compound 65.

MS: m/z=254 [M+H]$^+$.

Example 18

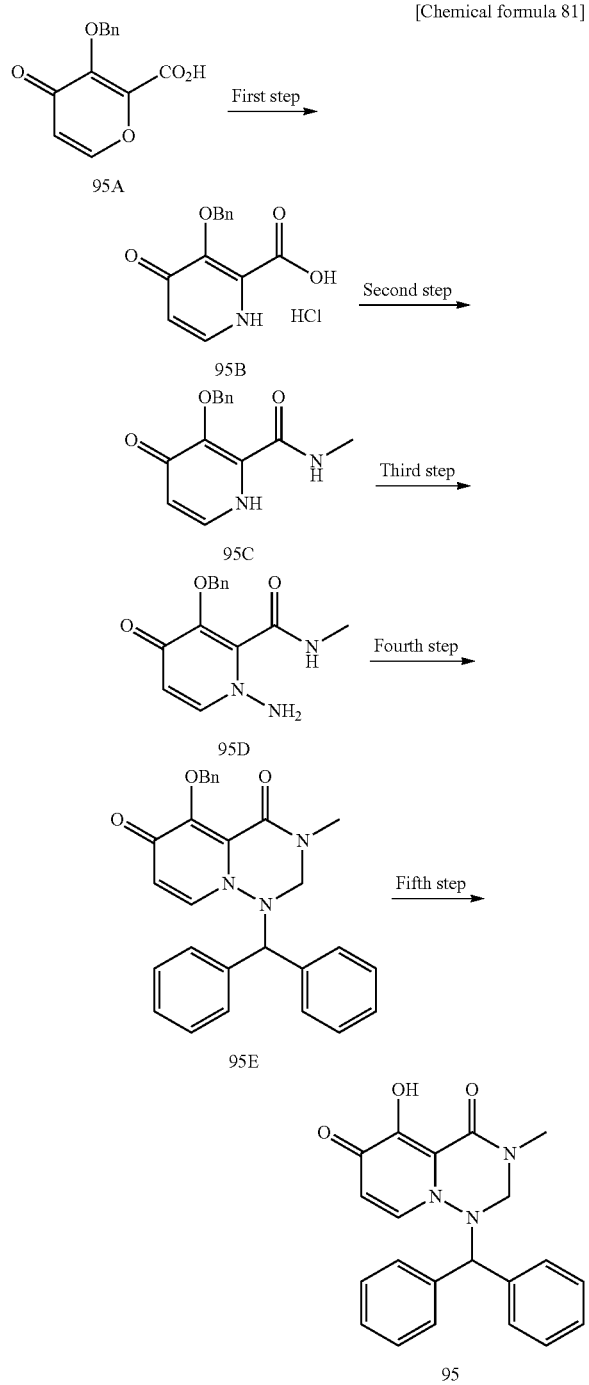

First Step

Compound 95A (WO2006/116764, 1 g, 4.06 mmol) was dissolved in 28% aqueous ammonia, and the solution was stirred at room temperature for 12 hours. After the reaction solution was concentrated, the resulting residue was neutralized with 2N hydrochloric acid, and the precipitated solid was suspended in ethyl acetate, filtered off, and dried to obtain 1.14 g (yield 100%) of Compound 95B.

$^1$H-NMR (DMSO-d6) δ: 5.14 (2H, s), 7.31 (1H, d, J=6.6 Hz), 7.34-7.41 (3H, m), 7.45-7.51 (2H, m), 8.17 (1H, d, J=6.6 Hz).

Second Step

WSC HCl (3.06 g, 15.98 mmol) and HOBt (1.58 g, 11.7 mmol) were added to a solution of Compound 95B (3.00 g, 10.65 mmol) in DMF (10 ml) at room temperature, the mixture was stirred for 10 minutes, and a methylamine 33 wt. % ethanol solution (1.50 g, 15.98 mmol) was added dropwise. After the reaction solution was stirred at the same temperature for 2 hours, and water was added, followed by extraction with chloroform five times. The extract was dried with sodium sulfate, the solvent was distilled off, and the resulting oil product was purified by subjecting to silica gel chromatography. From a fraction eluting with ethyl acetate-MeOH (6:4, v/v), 2.62 g (yield 95%) of Compound 95C was obtained as a solid.

$^1$H-NMR (CDCl$_3$) δ: 2.77 (3H, d, J=4.8 Hz), 5.49 (2H, s), 6.57 (1H, d, J=6.9 Hz), 7.25-7.43 (5H, m), 7.48 (1H, t, J=6.0 Hz), 8.23 (1H, brs), 9.77 (1H, brs).

Third Step

Potassium carbonate (4.20 g, 30.42 mmol) was suspended in a solution of Compound 95C (2.62 g, 10.14 mmol) in DMF (10 ml) at room temperature, the suspension was stirred for 5 minutes, O-(2,4-dinitrophenyl)hydroxylamine (3.03 g, 15.21 mmol) was added, and the mixture was stirred at the same temperature for 3 hours. Water was added to the reaction solution, this was extracted with chloroform five times, and the extract was dried with sodium sulfate. After the solvent was distilled off, the resulting oil product was purified by subjecting to silica gel chromatography. From a faction eluting with ethyl acetate-MeOH (6:4, v/v), 1.41 g (yield 51%) of Compound 95D was obtained as a solid.

$^1$H-NMR (CDCl$_3$) δ: 2.62 (3H, d, J=5.1 Hz), 5.06 (2H, s), 5.22 (2H, s), 6.18 (1H, d, J=7.8 Hz), 7.25-7.36 (5H, m), 5.89 (1H, d, J=7.8 Hz), 7.57 (1H, q, J=5.1 Hz).

Fourth Step

Paraformaldehyde (109.9 mg, 3.66 mmol) and acetic acid (22 mg, 0.37 mmol) were added to a solution of Compound 95D (1.0 g, 3.66 mmol) in toluene (10 ml), and the mixture was heated and stirred at 100° C. for 40 minutes. After cooling, the solvent was distilled off, the residue was dissolved in DMF (10 ml) without purification, cesium carbonate (3.58 g, 10.98 mmol) was added under ice cooling, and the mixture was stirred for 10 minutes. Benzhydryl bromide (1.36 g, 5.49 mmol) was added to the reaction solution, the mixture was stirred at room temperature for 3 hours, and water was added, followed by extraction with ethyl acetate three times. The extract was washed with water three times, and dried with sodium sulfate. The solvent was distilled off, and the resulting oil product was purified by subjecting to silica gel chromatography. From a fraction eluting with ethyl acetate-MeOH (9:1, v/v), 1.26 g (yield 71%) of Compound 95E was obtained as a solid.

$^1$H-NMR (CDCl$_3$) δ: 2.91 (3H, s), 4.26 (1H, d, J=13.2 Hz), 4.77 (1H, d, J=13.2 Hz), 5.12 (1H, s), 5.42 (1H, J=13.2 Hz), 5.45 (1H, d, J=13.2 Hz), 5.82 (1H, J=7.5 Hz), 6.71 (1H, d, J=7.5 Hz), 7.10-7.23 (5H, m), 7.27-7.46 (6H, m), 7.52 (2H, d, J=6.9 Hz), 7.60-7.64 (2H, m).

Fifth Step

Compound 95E (100 mg, 0.221 mmol) was dissolved in trifluoroacetic acid (2 ml) and the solution was stirred at room temperature for 1 hour. The solvent was distilled off, and the residue was dissolved in dichloromethane (2 ml), and neutralized with an aqueous saturated sodium bicarbonate solution. The resulting solution was made acidic with an aqueous citric acid solution, and the organic layer was separated. The aqueous layer was extracted with dichloromethane once, and the combined organic layers were washed with water, and dried with sodium sulfate. After the solvent was distilled off, the resulting solid was washed with diisopropyl ether to obtain 50 mg (yield 63%) of Compound 95.

$^1$H-NMR (CDCl$_3$) δ: 2.95 (3H, s), 4.36 (1H, d, J=13.2 Hz), 4.95 (1H, d, J=13.2 Hz), 5.22 (1H, s), 5.71 (1H, d, J=7.8 Hz), 6.75 (1H, d, J=7.8 Hz), 7.21 (5H, br s), 7.33-7.47 (4H, m), 7.55 (2H, d, J=6.6 Hz).

Example 19 distilled off, diisopropyl ether was added to the residue, and the precipitated solid was filtered off to obtain 42 mg (yield 29%) of Compound 107.

$^1$H-NMR (CDCl$_3$) δ: 0.953 (3H, d, J=3.9 Hz), 1.12 (3H, d, J=4.2 Hz), 4.51 (1H, 13.5 Hz), 4.83 (1H, d, J=13.5 Hz), 4.83-4.92 (1H, m), 5.18 (1H, s), 5.74 (1H, d, J=7.8 Hz), 6.73 (1H, d, J=7.8 Hz), 6.90 (1H, d, J=7.5 Hz), 7.12 (2H, dd, J=7.2 Hz, 8.1 Hz), 7.19-7.22 (1H, m), 7.37-7.41 (3H, m), 7.55 (1H, s).

Example 20

[Chemical formula 82]

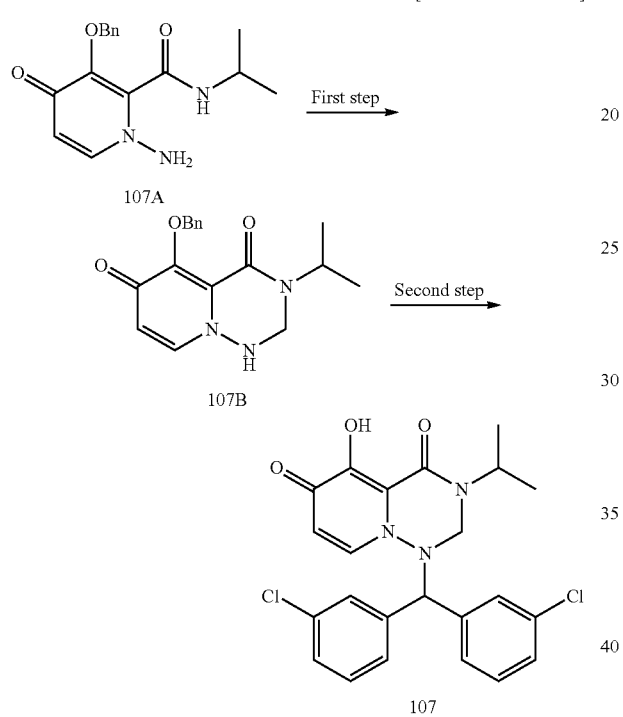

[Chemical formula 83]

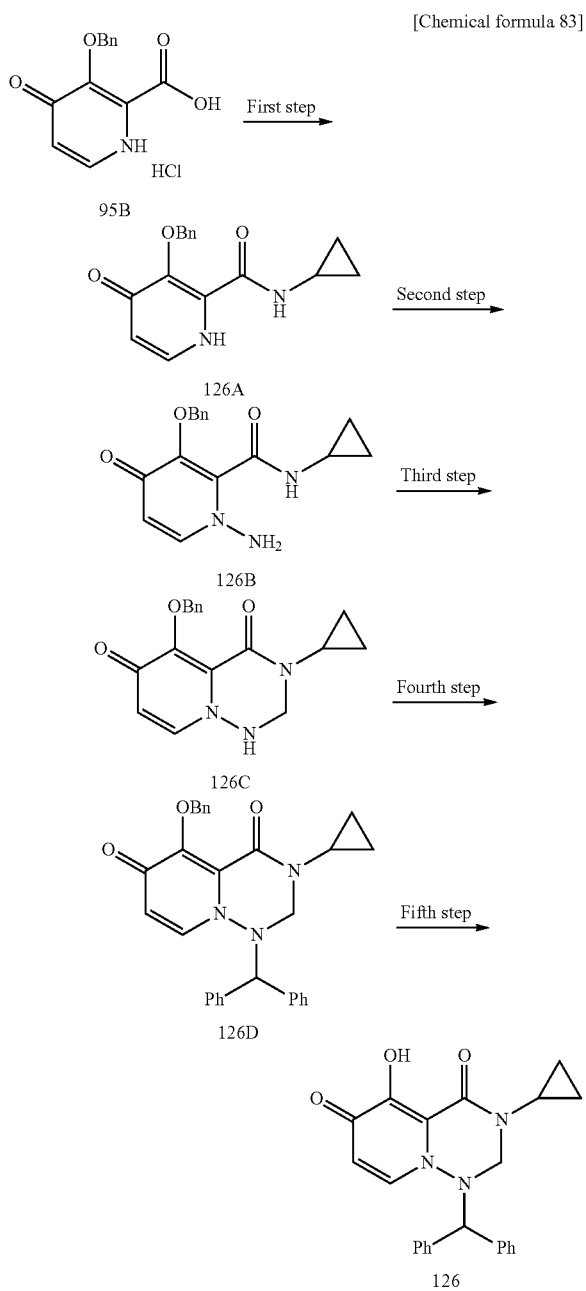

First Step

Paraformaldehyde (299 mg, 9.96 mmol) and acetic acid (1 ml) were added to a solution of Compound 107A (3.0 g, 9.96 mmol) synthesized according to the synthetic method of Compound 95D in DMF (30 ml), and the mixture was heated and stirred at 120° C. for 4 hours. After the solvent was distilled off, ethyl acetate-diisopropyl ether were added to the residue, and the precipitated solid was filtered off to obtain 2.85 g (yield 91%) of Compound 107B.

$^1$H-NMR (CDCl$_3$) δ: 1.19 (6H, J=6.6 Hz), 4.34 (2H, J=7.5 Hz), 4.72-4.86 (1H, m), 5.30 (2H, s), 5.49 (1H, t, J=7.5 Hz), 6.36 (1H, d, J=7.8 Hz), 7.26-7.35 (4H, m), 7.37 (1H, d, J=7.8 Hz), 7.55-7.58 (2H, m).

Second Step

To a solution of Compound 107B (100 mg, 0.319 mmol) in acetic acid (2 ml) were added 96% sulfuric acid (0.5 ml) and bis(3-chlorophenyl)methanol (242.3 mg, 0.957 mmol) at room temperature, and the mixture was stirred at 80° C. for 2 hours. After the reaction solution was cooled to room temperature, water was added, followed by extraction with ethyl acetate three times. The organic layer was washed with water once, and dried with sodium sulfate. After the solvent was First Step Compound 95B (1.00 g, 3.55 mmol) and cyclopropanamine (0.492 ml, 7.10 mmol) were added to pyridine (20 ml), 1-hydroxybenzotriazole (544 mg, 3.55 mmol) and 1-(3-dimethylaminopropyl)-3-ethylcarbodiimide hydrochloride (1.36 g, 7.10 mmol) were sequentially added, and the mixture was stirred at room temperature for 18 hours. The solvent was distilled off under reduced pressure, and the resulting crude product was purified by silica gel column chromatography (chloroform methanol, 95:5, v/v) and, subsequently, amino column chromatography (chloroform-methanol, 99:1, v/v) to obtain 1.19 g of Compound 126A as a colorless solid.

$^1$H-NMR (CDCl$_3$) δ: 0.22 (1H, m), 0.70 (2H, m), 2.76-2.83 (1H, m), 5.50 (2H, s), 6.59 (1H, dd, J=7.0, 1.9 Hz), 7.44 (5H, d, J=0.7 Hz), 7.53 (1H, dd, J=6.9, 6.2 Hz), 8.30 (1H, brs), 9.71 (1H, brs).

Second Step

Compound 126A (1.19 g, 4.19 mmol) was dissolved in DMF (15 ml), potassium carbonate (2.90 g, 20.1 mmol) was added, and the mixture was stirred at room temperature for 30 minutes. O-(2,4-dinitrophenyl)hydroxylamine (1.67 g, 8.38 mmol) was added, and the mixture was stirred at room temperature for 18 hours. Chloroform was added to the reaction solution, the precipitated yellow precipitate was filtered to remove, and the filtrate was concentrated under reduced pressure. The resulting crude product was purified by amino column chromatography (chloroform-methanol, 97:3→95:5, v/v) to obtain 851 mg of Compound 126B as a yellow solid.

$^1$H-NMR (CDCl$_3$) δ: 0.41-0.46 (2H, m), 0.76 (2H, m), 2.73-2.81 (1H, m), 5.19 (2H, s), 5.61 (2H, s), 6.26 (1H, d, J=7.2 Hz), 7.38 (5H, s), 7.44 (1H, d, J=7.8 Hz), 7.70 (1H, s).

Third Step

Compound 126B (847 mg, 2.83 mmol) and paraformaldehyde (255 mg, 8.49 mmol) were added to ethanol (12 ml), and the mixture was stirred at 140° C. for 30 minutes under microwave irradiation, the resulting solution was concentrated under reduced pressure, the resulting crude product was purified by silica gel column chromatography (chloroform-methanol, 97:3→95:5→90:10, v/v) and, subsequently, amino column chromatography (chloroform-methanol, 97:3, v/v) methylene chloride-ethyl ether were added, and the precipitated solid was filtered off to obtain 665 mg of Compound 126C as a colorless solid.

$^1$H-NMR (CDCl$_3$) δ: 0.61-0.66 (2H, m), 0.87 (2H, m), 2.68-2.76 (1H, m), 4.32 (2H, d, J=7.9 Hz), 5.28 (2H, s), 6.33 (1H, d, J=7.7 Hz), 6.45 (1H, t, J=7.7 Hz), 7.33 (3H, m), 7.38 (1H, d, J=7.7 Hz), 7.52 (2H, m).

Fourth Step

Compound 126C (100 mg, 0.321 mmol) was dissolved in DMF (0.5 ml), cesium carbonate (314 mg, 0.964 mmol) and (bromomethylene)dibenzene (119 mg, 0.482 mmol) were added at 0° C., and the mixture was stirred at room temperature for 2 hours. The reaction solution was poured into water, this was extracted with ethyl acetate, and the organic layer was washed with water, and dried with sodium sulfate. The solvent was distilled off under reduced pressure, and the resulting crude product was purified by silica gel column chromatography (chloroform-methanol, 97:3→95:5, v/v) to obtain 124 mg of Compound 126D as a colorless gummy substance.

$^1$H-NMR (CDCl$_3$) δ: 0.37-0.47 (2H, m), 0.74 (2H, m), 2.63-2.68 (1H, m), 4.35 (1H, d, J=13.4 Hz), 4.65 (1H, d, J=13.4 Hz), 5.07 (1H, s), 5.40 (1H, d, J=10.7 Hz), 5.47 (1H, d, J=10.5 Hz), 5.79 (1H, d, J=7.6 Hz), 6.67 (1H, d, J=7.8 Hz), 7.04-7.62 (15H, m).

Fifth Step

Trifluoroacetic acid (2 ml) was added to Compound 126D obtained in Fourth step, and the mixture was stirred at room temperature for 1.5 hours. After concentrated under reduced pressure, a pH was adjusted to 6 with an aqueous sodium bicarbonate solution and 2N hydrochloric acid, and this was extracted with chloroform and dried with sodium sulfate. After the solvent was distilled off under reduced pressure, methylene chloride-ethyl ether were added, and the precipitated solid was filtered off to obtain 52 mg of Compound 126 as a colorless solid.

$^1$H-NMR (DMSO-d6) δ: −0.19−−0.06 (1H, m), 0.44-0.54 (1H, m), 0.82 (2H, m), 2.62-2.69 (1H, m), 4.21 (1H, d, J=13.3 Hz), 5.11 (1H, d, J=13.1 Hz), 5.32 (1H, s), 5.47 (1H, t, J=11.1 Hz), 7.13 (1H, d, J=7.6 Hz), 7.23 (3H, m), 7.28-7.47 (8H, m), 7.69 (2H, t, J=8.5 Hz).

MS: m/z=388 [M+H]$^+$.

Example 21

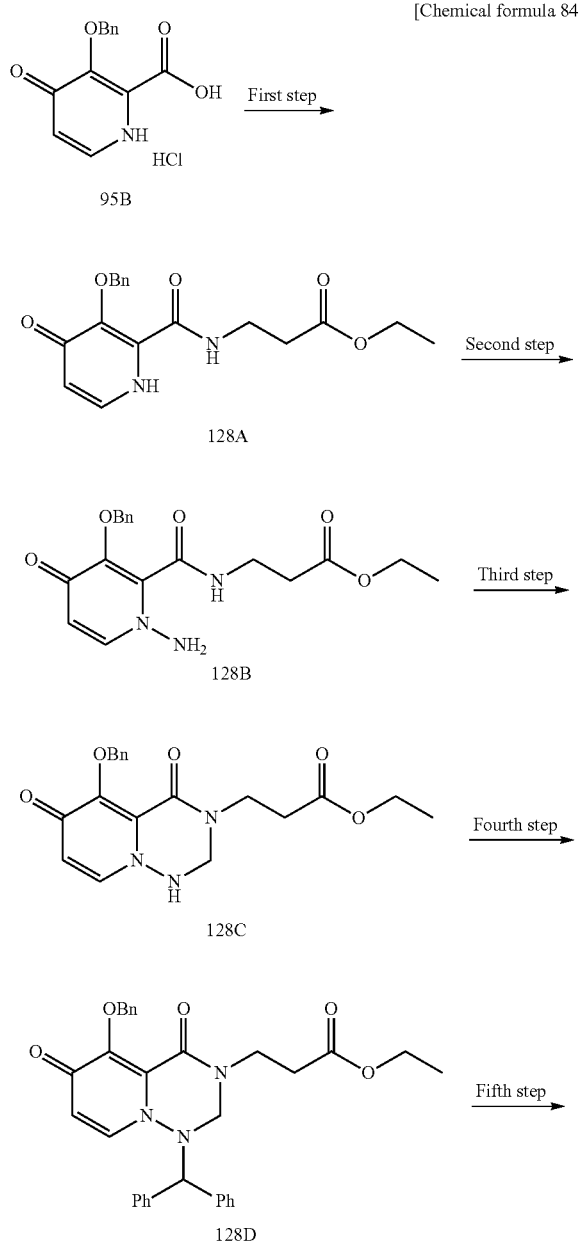

[Chemical formula 84]

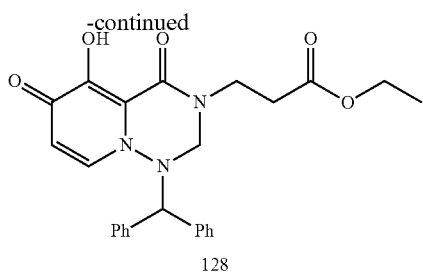

128

First Step

Compound 95B (2.40 g, 8.52 mmol) and ethyl 3-aminopropanoate hydrochloride (2.62 g, 17.0 mmol) were added to pyridine (30 ml), 1-hydroxybenzotriazole (1.31 g, 8.52 mmol) and 1-(3-dimethylaminopropyl)-3-ethylcarbodiimide hydrochloride (3.27 g, 17.0 mmol) were sequentially added, and the mixture was stirred at room temperature for 2 hours. The solvent was distilled off under reduced pressure, and the resulting crude product was purified by amino column chromatography (chloroform-methanol, 95:5, v/v) to obtain 1.90 g of Compound 128A as a colorless solid.

$^1$H-NMR (CDCl$_3$) δ: 1.29 (3H, t, J=7.1 Hz), 2.48 (2H, t, J=6.4 Hz), 3.58 (2H, q, J=6.3 Hz), 4.17 (2H, q, J=7.1 Hz), 5.59 (2H, s), 6.57 (1H, dd, J=7.1, 1.6 Hz), 7.37-7.52 (6H, m), 8.73 (1H, brs), 9.72 (1H, brs).

Second Step

Compound 128A (2.58 g, 7.49 mmol) was dissolved in DMF (30 ml), potassium carbonate (5.18 g, 37.5 mmol) was added, and the mixture was stirred at room temperature for 30 minutes. O-(2,4-dinitrophenyl)hydroxylamine (2.98 g, 15.0 mmol) was added, and the mixture was stirred at room temperature for 20 hours. Chloroform was added to the reaction solution, the precipitated yellow precipitate was filtered to remove, and the filtrate was concentrated under reduced pressure. The resulting crude product was purified by amino column chromatography (chloroform-methanol, 97:3→95:5, v/v) and, subsequently, silica gel column chromatography (chloroform-methanol, 95:5→92:8, v/v) to obtain 1.67 g of Compound 128B as a yellow solid.

$^1$H-NMR (CDCl$_3$) δ: 1.26 (3H, t, J=7.2 Hz), 2.42 (2H, t, J=6.6 Hz), 3.43 (2H, q, J=6.4 Hz), 4.12 (2H, q, J=7.1 Hz), 5.13 (2H, s), 5.53 (2H, s), 6.21 (1H, d, J=7.6 Hz), 7.33 (5H, s), 7.39 (1H, d, J=7.6 Hz), 7.85 (1H, t, J=5.6 Hz).

Third Step

Compound 128B (1.66 g, 4.62 mmol) and paraformaldehyde (416 mg, 13.9 mmol) were added to ethanol (20 ml), and the mixture was stirred at 140° C. for 30 minutes under microwave irradiation. The reaction solution was concentrated under reduced pressure, and the resulting crude product was purified by amino column chromatography (chloroform-methanol, 99:1→95:5, v/v) to obtain 1.57 g of Compound 128C as a colorless solid.

$^1$H-NMR (CDCl$_3$) δ: 1.27 (3H, t, J=7.2 Hz), 2.70 (2H, t, J=5.7 Hz), 3.57 (2H, t, J=5.8 Hz), 4.13 (2H, q, J=7.1 Hz), 4.50 (2H, d, J=7.9 Hz), 5.27 (2H, s), 5.87 (1H, t, J=7.8 Hz), 6.32 (1H, d, J=7.6 Hz), 7.31 (4H, m), 7.54 (2H, m).

Fourth Step

Compound 128C (1.00 g, 2.69 mmol) was dissolved in DMF (10 ml), cesium carbonate (2.63 g, 8.08 mmol) and (bromomethylene)dibenzene (998 mg, 4.04 mmol) were added at 0° C., and the mixture was stirred at room temperature for 18 hours. The reaction solution was poured into water, this was extracted with ethyl acetate, and the organic layer was washed with water, and dried with sodium sulfate. The solvent was distilled off under reduced pressure, and the resulting crude product was purified by silica gel column chromatography (chloroform-methanol, 98:2, v/v) to obtain 500 mg of Compound 128D as a colorless gummy substance.

$^1$H-NMR (CDCl$_3$) δ: 1.25 (3H, t, J=7.3 Hz), 2.46 (1H, m), 2.70-2.80 (1H, m), 2.87-2.96 (1H, m), 4.11 (2H, q, J=7.3 Hz), 4.12 (1H, m), 4.48 (1H, d, J=13.7 Hz), 4.85 (1H, d, J=13.7 Hz), 5.10 (1H, s), 5.47 (2H, s), 5.83 (1H, d, J=8.0 Hz), 6.73 (1H, d, J=8.0 Hz), 7.37 (15H, m).

Fifth Step

Trifluoroacetic acid (1 ml) was added to Compound 128D (40 mg, 0.074 mmol), and the mixture was stirred at room temperature for 1 hour. After concentrated under reduced pressure, a pH was adjusted to 6 with an aqueous sodium bicarbonate solution and 2 N hydrochloric acid, and this was extracted with chloroform, and dried with sodium sulfate. After the solvent was distilled off under reduced pressure, methylene chloride-ethyl ether were added, and the precipitated solid was filtered off to obtain 20 mg of Compound 128 as a colorless solid.

$^1$H-NMR (DMSO-d6) δ: 1.16 (3H, t, J=7.1 Hz), 2.45-2.58 (3H, m), 3.70 (1H, m), 4.02 (2H, q, J=7.1 Hz), 4.39 (1H, d, J=13.4 Hz), 5.09 (1H, d, J=13.3 Hz), 5.48 (1H, d, J=3.2 Hz), 5.51 (1H, s), 7.19-7.38 (7H, m), 7.45 (2H, t, J=7.3 Hz), 7.69 (2H, d, J=7.2 Hz).

MS: m/z=448 [M+H]$^+$.

Example 22

[Chemical formula 85]

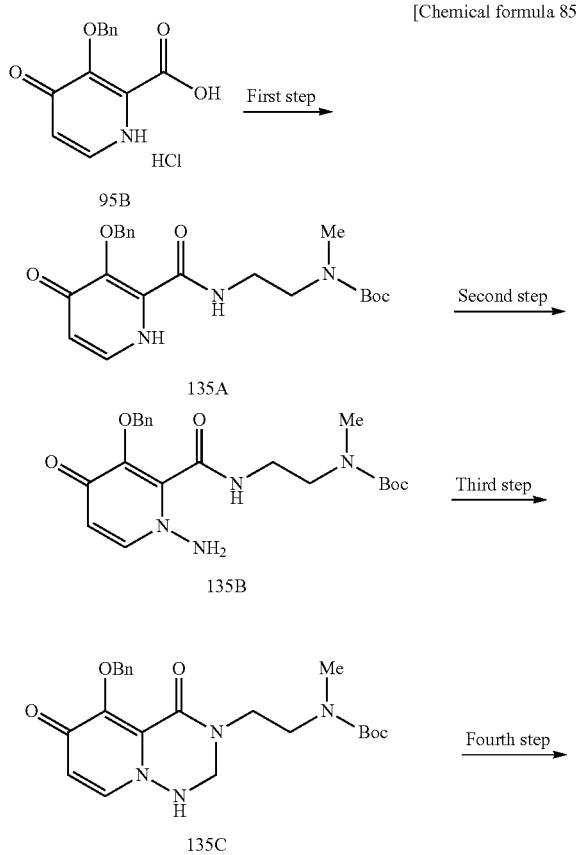

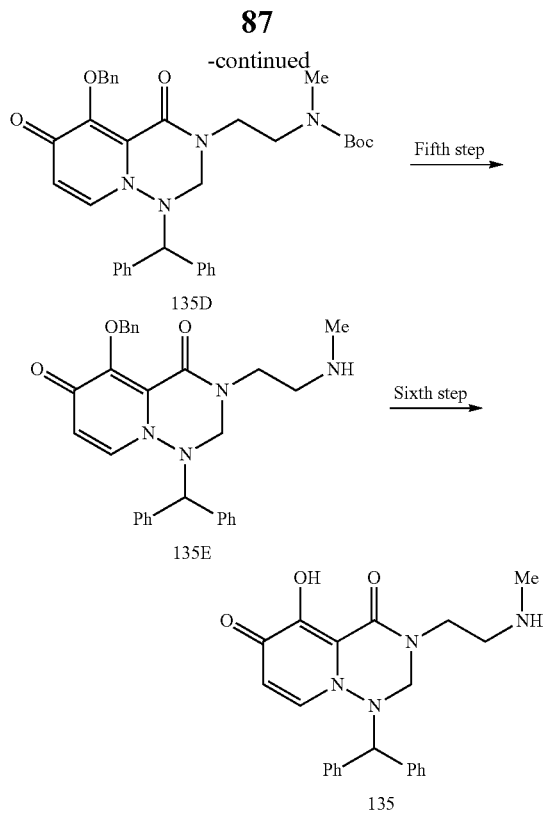

First Step

Compound 95B (1.50 g, 5.32 mmol) and tert-butyl 2-aminoethyl(methyl)carbamate (1.86 g, 10.7 mmol) were added to pyridine (20 ml), 1-hydroxybenzotriazole (815 mg, 5.32 mmol) and 1-(3-dimethylaminopropyl)-3-ethylcarbodiimide hydrochloride (2.04 g, 10.7 mmol) were sequentially added, and the mixture was stirred at room temperature for 2 hours. The reaction solution was poured into 1N hydrochloric acid, this was extracted with ethyl acetate, and dried with sodium sulfate. The solvent was distilled off under reduced pressure, and the resulting crude product was purified by amino column chromatography (chloroform-methanol, 95:5, v/v) and, subsequently, silica gel column chromatography (chloroform-methanol, 95:5, v/v) to obtain 1.63 g of Compound 135A as a colorless gummy substance.

$^1$H-NMR (CDCl$_3$) δ: 1.44 (9H, s), 2.82 (3H, s), 3.28 (4H, m), 5.59 (2H, s), 6.57 (1H, d, J=6.0 Hz), 7.46 (6H, m), 8.46 (1H, m), 9.68 (1H, brs).

Second Step

Compound 135A (1.05 g, 2.62 mmol) was dissolved in DMF (15 ml), potassium carbonate (1.81 g, 13.1 mmol) was added, and the mixture was stirred at room temperature for 30 minutes. O-(2,4-dinitrophenyl)hydroxylamine (1.04 g, 5.23 mmol) was added, and the mixture was stirred at room temperature for 18 hours. Chloroform was added to the reaction solution, the precipitated yellow precipitate was filtered to remove, and the filtrate was concentrated under reduced pressure. The resulting crude product was purified by amino column chromatography (chloroform methanol, 97:3→95:5, v/v) to obtain 887 mg of Compound 135B as a pale yellow solid.

$^1$H-NMR (CDCl$_3$) δ: 1.44 (9H, s), 2.84 (3H, s), 3.38 (4H, m), 5.33 (2H, s), 5.68 (1H, brs), 5.80 (1H, brs), 6.35 (1H, d, J=7.6 Hz), 6.74 (1H, brs), 7.39 (5H, brm), 7.52 (1H, t, J=9.5 Hz).

Third Step

Compound 135B (880 mg, 2.11 mmol) and paraformaldehyde (190 mg, 6.34 mmol) were added to ethanol (18 ml), and the mixture was stirred at 140° C. for 30 minutes under microwave irradiation. The reaction solution was concentrated under reduced pressure, and the resulting crude product was purified by silica gel column chromatography (chloroform-methanol, 97:3→95:5→90:10, v/v) and, subsequently, amino column chromatography (chloroform-methanol, 97:3, v/v) to obtain 721 mg of Compound 135C as a colorless solid.

$^1$H-NMR (CDCl$_3$) δ: 1.29 (9H, s), 2.95 (3H, s), 4.38 (2H, brs), 5.33 (2H, brs), 6.36 (1H, d, J=7.6 Hz), 6.85 (1H, t, J=7.4 Hz), 7.33 (4H, m), 7.55 (2H, m).

MS: m/z=429 [M+H]$^+$.

Fourth Step

Compound 135C (720 mg, 1.68 mmol) was dissolved in DMF (3.5 ml), cesium carbonate (1.64 g, 5.04 mmol) and (bromomethylene)dibenzene (623 mg, 2.52 mmol) were added at 0° C., and the mixture was stirred at room temperature for 18 hours. The reaction solution was poured into water, this was extracted with ethyl acetate, and the organic layer was washed with water, and dried with sodium sulfate. The solvent was distilled off under reduced pressure, and the resulting crude product was purified by silica gel column chromatography (chloroform-methanol, 97:3→95:5, v/v) to obtain 732 mg of Compound 135D.

Fifth Step

To Compound 135D (727 mg, 1.22 mmol) was added 4N HCl (ethyl acetate solution, 10 ml). After stirring at room temperature for 1 hour, the solvent was distilled off under reduced pressure. An aqueous saturated sodium bicarbonate solution was added, and this was extracted with chloroform, and dried with sodium sulfate. The solvent was distilled off under reduced pressure, methylene chloride-ethyl ether were added to the resulting crude product, and the precipitated solid was filtered off to obtain 575 mg of Compound 135E as a colorless solid.

Sixth Step

Trifluoroacetic acid (2 ml) was added to Compound 135E (50 mg, 0.10 mmol) and the mixture was stirred at room temperature for 1.5 hours. After concentrated under reduced pressure, a pH was adjusted to 6 with an aqueous sodium bicarbonate solution and an aqueous ammonium chloride solution, and this was extracted with chloroform, and dried with sodium sulfate. After the solvent was distilled off under reduced pressure, methylene chloride-ethyl ether were added, and the precipitated solid was filtered to obtain 15 mg of Compound 135 as a colorless solid.

$^1$H-NMR (DMSO-d6) δ: 2.40 (3H, s), 2.80 (1H, s), 3.12 (3H, m), 3.87 (1H, m), 4.37 (1H, d, J=13.6 Hz), 5.10 (1H, d, J=13.4 Hz), 5.52 (1H, s), 5.53 (1H, d, J=5.5 Hz), 7.15-7.70 (11H, m).

MS: m/z=405 [M+H]$^+$.

Example 23

[Chemical formula 86]

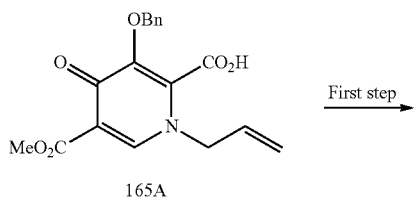

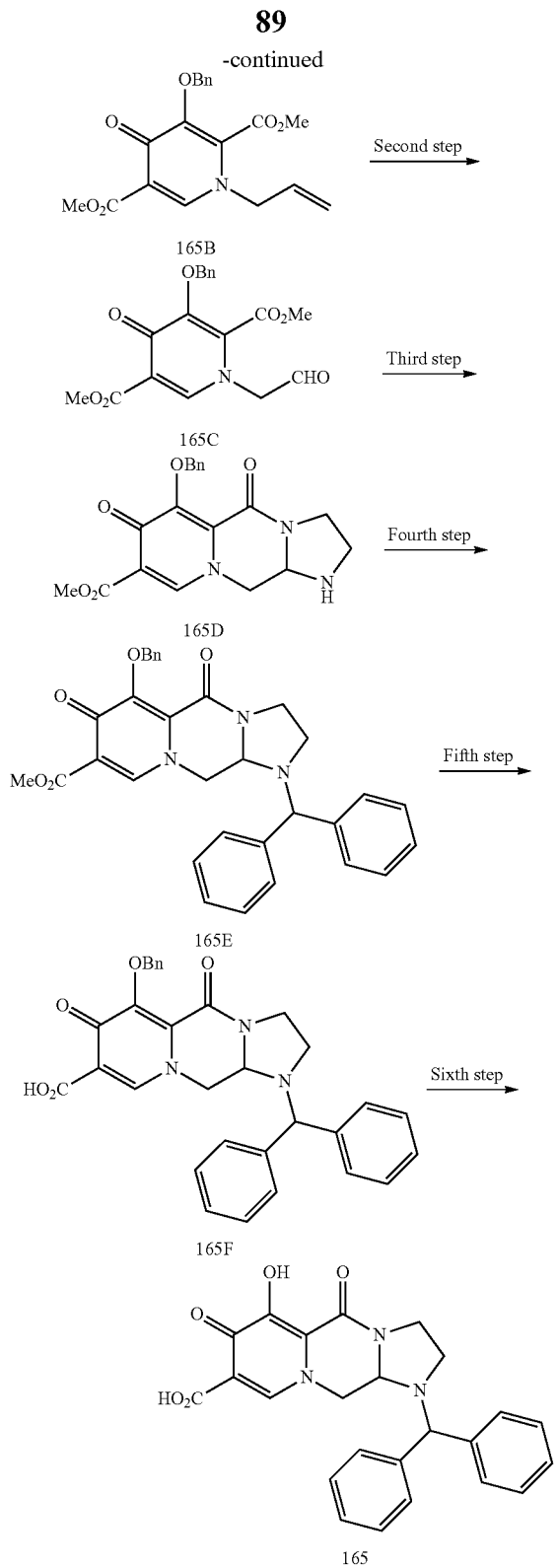

First Step

Potassium carbonate (17.9 g, 129 mmol) and methyl iodide (8.03 mL, 129 mmol) were sequentially added to a solution of Compound 165A (WO 2006/088173, 37.0 g, 108 mmol) in DMF (370 mL) at room temperature, and the mixture was stirred for 1.5 hours. The reaction solution was added to a solution of ammonium chloride (20.8 g, 390 mmol) in water (1110 mL) under ice-cooling, and the precipitated solid was filtered off, and washed with water to obtain a crude product (33 g). The aqueous layer was salted out with sodium chloride, extracted with ethyl acetate, and dried with sodium sulfate. The solvent was distilled off under reduced pressure, and a crude product (9 g) was obtained from the resulting residue. The crude products were combined, and purified by silica gel column chromatography (ethyl acetate/n-hexane=50%→100%) to obtain Compound 165B (36.5 g, 95%) as a white solid.

Second Step

Potassium osmate dihydrate (1.13 g, 3.06 mmol), sodium periodate (87.3 g, 408 mmol) and water (365 mmol) were sequentially added to a solution of Compound 165B (36.5 g, 102 mmol) in 1,4-dioxane (548 mL) at room temperature, and the mixture was stirred for 6 hours. The reaction solution was extracted with methylene chloride, and dried with sodium sulfate. The solvent was distilled off under reduced pressure, and the resulting residue was purified by silica gel column chromatography (ethyl acetate/n-hexane=50%→100%) to obtain Compound 165C (33.0 g, 90%) as a brown foam.

Third Step

Ethylenediamine (0.247 mL, 3.66 mmol) and acetic acid (0.0210 mL, 0.366 mmol) were sequentially added to a suspension of Compound 165C (1.38 g, 3.66 mmol) in toluene (25 mL) at room temperature, and the mixture was stirred for 1 hour, and further stirred at 50° C. for 17 hours. The precipitated solid was filtered off, and washed with ether to obtain Compound 165D (1.11 g, 100%) as a pale yellow solid.

$^1$HNMR (DMSO-$d_6$) δ: 3.05 (2H, m), 3.26 (1H, m), 3.63 (2H, m), 3.75 (3H, s), 3.87 (1H, m), 4.52 (1H, dd, J=3.3, 12.6 Hz), 4.69 (1H, m), 4.99 (1H, d, J=10.4 Hz), 5.15 (1H, d, J=10.4 Hz), 7.35 (3H, m), 7.54 (2H, m), 8.41 (1H, s).

Fourth Step

Bromodiphenylmethane (2.26 g, 9.14 mmol) was added to a suspension of Compound 165D (2.77 g, 7.50 mmol), potassium carbonate (2.23 g, 16.1 mmol) and sodium iodide (102 mg, 0.680 mmol) in acetonitrile (30 mL) at room temperature, and the mixture was stirred at 90° C. for 7 hours. The reaction solution was poured into hydrochloric acid (2 N, 10 mL) and ice (20 g), and this was extracted with chloroform (100 mL×2), and dried with sodium sulfate. The solvent was distilled off under reduced pressure, and the resulting residue was purified by silica gel column chromatography (chloroform/methanol=0%→5%) to obtain Compound 165E (2.72 g, 68%) as a pale yellow solid.

Fifth Step

An aqueous sodium hydroxide solution (2 N, 10 mL) was added to a solution of Compound 165E (2.72 g, 5.08 mmol) in ethanol (30 mL) at room temperature, and the mixture was stirred for 3 days. Hydrochloric acid (1 N, 20 mL) was added to the reaction solution at room temperature (pH=1), and this was extracted with chloroform (100 mL×2), and dried with sodium sulfate. The solvent was distilled off under reduced pressure, and the resulting residue was purified by silica gel column chromatography (chloroform/methanol=0%→10%) to obtain Compound 165F (1.77 g, 67%) as a pale yellow solid.

$^1$HNMR (DMSO-$d_6$) δ: 2.63 (1H, m), 3.16 (1H, m), 3.49 (1H, m), 3.73 (1H, m), 4.12 (2H, m), 4.56 (1H, m), 5.04 (1H, s), 5.09 (1H, d, J=10.7 Hz), 5.19 (1H, d, J=10.7 Hz), 7.28-7.53 (15H, m), 8.32 (1H, s), 8.39 (1H, s).

Sixth Step

A solution of Compound 165F (1.77 g, 3.39 mmol) and lithium chloride (0.515 g, 12.2 mmol) in N,N'-dimethylimidazolidinone (20 mL) was stirred at 90° C. for 1 hour. Water (10 mL), hydrochloric acid (2 N, 10 mL) and water (10 mL)

were sequentially added to the reaction solution at room temperature. The precipitated solid was filtered off, and washed with ether, DMF-water were added, and the precipitated solid was filtered off to obtain Compound 165 (599 mg, 41%) as a white solid.

$^1$HNMR (DMSO-d$_6$) δ: 2.60 (1H, m), 3.20 (1H, m), 3.64 (2H, m), 4.00 (2H, m), 4.55 (1H, m), 5.01 (1H, s), 7.28-7.47 (10H, m), 8.16 (1H, s), 11.97 (1H, brs).

MS: m/z=432 [M+H]$^+$.

Example 24

[Chemical formula 87]

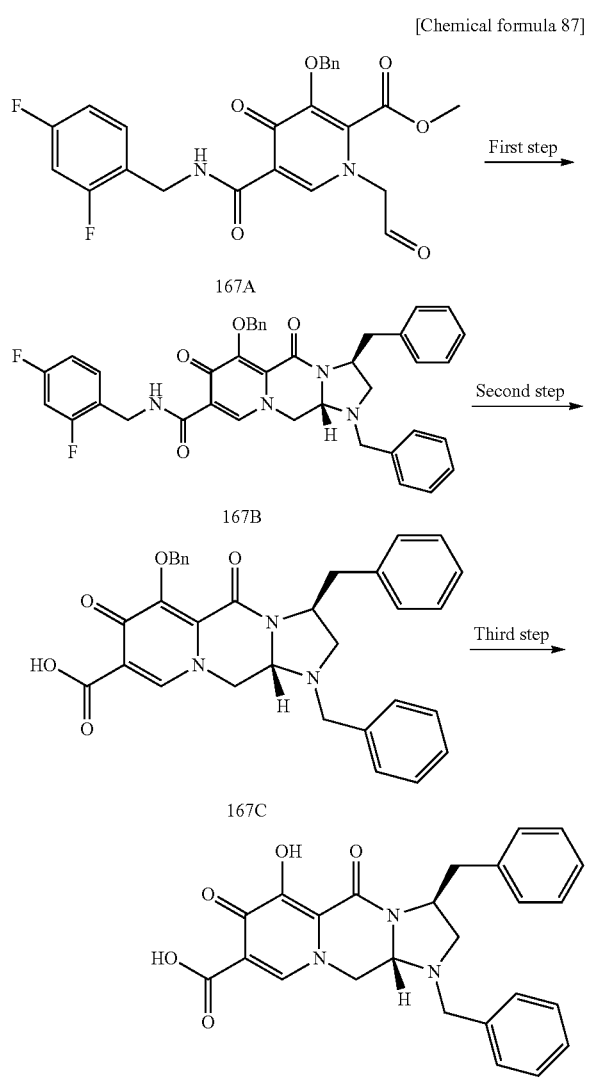

First Step (S)—N1-benzyl-3-phenylpropan-1,2-diamine (Journal of the American Chemical Society; English; 127; 30; 2005; 10504, 1.83 g, 7.61 mmol) and acetic acid (0.5 ml) were added to a solution of Compound 167A (WO 2006/11674, 3.58 g, 7.61 mmol) in xylene (30 ml), and the mixture was refluxed for 2 hours. After cooling to room temperature, the solvent was distilled off, and the resulting oil product was purified by subjecting to silica gel chromatography. The column was eluted initially with n-hexane-ethyl acetate (9:1, v/v) and, then, n-hexane-ethyl acetate (1:1, v/v). The objective fraction was concentrated to obtain 349 mg (yield 7%) of Compound 167B.

$^1$HNMR (CDCl$_3$) δ: 2.54 (1H, t, J=9.6 Hz), 2.77 (1H, dd, J=9.0 Hz, 13.2 Hz), 3.31 (1H, dd, J=6.9 Hz, 9.6 Hz), 3.43-3.78 (5H, m), 4.04-4.15 (1H, m), 4.42-4.48 (1H, m), 4.62 (2H, d, J=6.0 Hz), 5.29 (1H, d, J=10.5 Hz), 5.43 (1H, d, J=10.5 Hz), 6.77-6.85 (2H, m), 7.19-7.39 (14H, m), 7.60 (2H, d, J=6.3 Hz), 8.05 (1H, s).

Second Step

Boc$_2$O (3 ml) and DMAP (180 mg, 1.47 mmol) were added to a solution of Compound 167B (968 mg, 1.47 mmol) in MeCN (10 ml), and the mixture was heated to reflux for 5 hours. A 2N aqueous sodium hydroxide solution was added to the reaction solution to stop the reaction, and this was neutralized using 2N hydrochloric acid, followed by extraction with ethyl acetate three times. After the extract was washed with an aqueous saturated sodium chloride solution, the solvent was distilled off, and the resulting oil product was purified by silica gel chromatography. The column was eluted initially with n-hexane-ethyl acetate (6:4, v/v) and, then only ethyl acetate. The objective fraction was concentrated to obtain 349 mg (yield 45%) of 167C as a solid.

$^1$HNMR (CDCl$_3$) δ: 2.54 (1H, t=9.0 Hz), 2.76 (1H, dd, J=9.3 Hz, 16.5 Hz), 3.31 (1H, dd, J=6.9 Hz, 9.6 Hz), 3.45 (1H, dd, J=3.3 Hz, 12.6 Hz), 3.51-3.78 (4H, m), 4.04-4.13 (1H, m), 4.42-4.52 (1H, m), 4.61 (2H, d, J=6.0 Hz), 2.79 (1H, d, J=10.2 Hz), 5.29 (1H, d, J=10.2 Hz), 5.43 (1H, d, J=10.2 Hz), 6.76-7.39 (11H, m), 7.60 (2H, d, J=6.6 Hz), 8.05 (1H, s), 10.42 (1H, t, J=5.7 Hz).

Third Step

Compound 167C (150 mg, 0.280 mmol) was dissolved in trifluoroacetic acid (2 ml), and the solution was stirred at room temperature for 1 hour. The solvent was distilled off, the residue was dissolved in dichloromethane (2 ml), and the solution was neutralized with an aqueous saturated sodium bicarbonate solution. The resulting solution was made acidic with an aqueous citric acid solution, and the organic layer was separated. The aqueous layer was extracted with dichloromethane once, and the combined organic layers were washed with water, and dried with sodium sulfate. The solvent was distilled off, and the resulting solid was washed with diisopropyl ether to obtain 71 mg (yield 57%) of Compound 167.

$^1$HNMR (CDCl$_3$) δ: 2.65 (1H, dd, J=8.4 Hz, 9.6 Hz), 2.97 (1H, dd, J=9 Hz, 13.5 Hz), 3.43 (1 J, dd, J=7.2 Hz, 9.6 Hz), 3.55 (1H, dd, J=3.0 Hz, 13.2 Hz), 3.61-3.80 (4H, m), 4.15 (1H, dd, J=4.2 Hz, 9.9 Hz), 4.51-4.60 (1H, m), 7.15-7.18 (2H, m), 7.28-7.38 (8H, m), 8.02 (1H, s), 12.04 (1H, s).

Example 25

[Chemical formula 88]

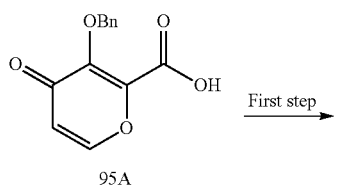

First Step

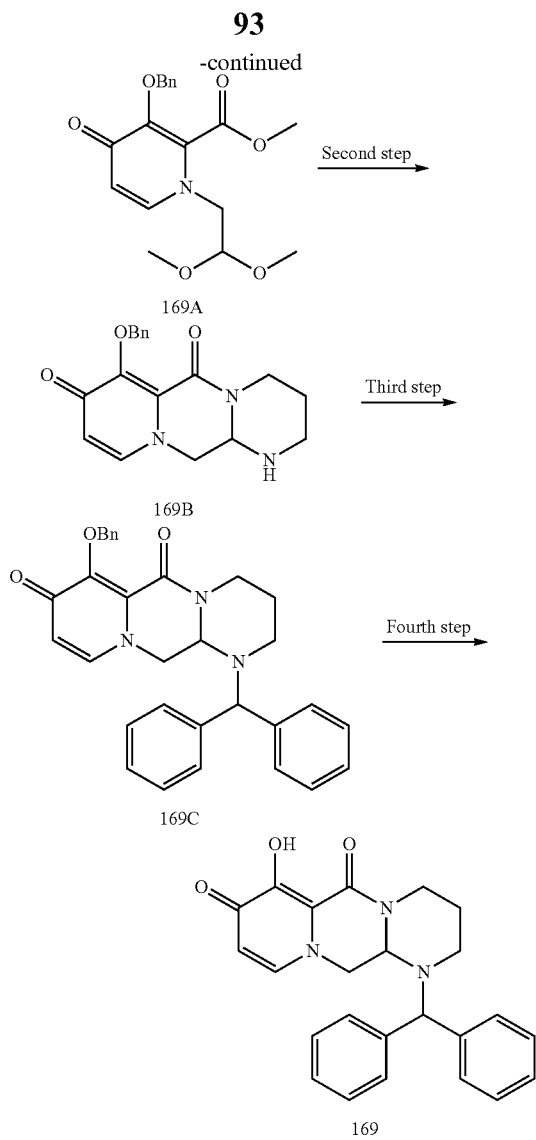

First Step 2,2-Dimethoxyethanamine (0.49 ml, 4.47 mmol) was added to a solution of Compound 95A (WO 2006/116764, 500 mg, 2.03 mmol) in ethanol (5 mL), and the mixture was stirred at 80° C. for 3 hours. After the reaction solution was allowed to cool, acetic acid (0.27 ml, 4.69 mmol) was added at room temperature, followed by concentration under reduced pressure. The resulting residue was dissolved in DMF (5 mL), and DBU (0.66 mL, 4.4 mmol) and, subsequently, methyl iodide (1.02 mL, 16.2 mmol) were added under a nitrogen atmosphere, and the mixture was stirred at room temperature for 3 hours. An aqueous saturated sodium bicarbonate solution, and ethyl acetate were added to the reaction solution, the ethyl acetate layer was separated, and the aqueous layer was extracted with ethyl acetate. Sodium sulfate was added to the combined extracts, this was filtered, and concentrated, and the resulting residue was purified by subjecting to silica gel chromatography. The column was eluted with chloroform-methanol (9:1), and the objective fraction was concentrated to obtain 258 mg of Compound 169A as a brown oil.

$^1$H-NMR (CDCl$_3$) δ: 3.37 (6H, s), 3.80 (3H, s), 3.87 (2H, d, J=4.8 Hz), 4.46 (1H, t, J=4.8 Hz), 5.30 (2H, s), 6.75 (1H, d, J=6.0 Hz), 7.30-7.41 (6H, m).

Second Step

Formic acid (31 mL) and, subsequently, water (5 mL) were added to Compound 169A (1.00 g, 2.88 mmol) and the mixture was stirred at 70° C. for 6.5 hours. Water and ethyl acetate were added to the reaction mixture, the ethyl acetate layer was separated, and the aqueous layer was extracted with ethyl acetate. The combined extracts were washed with an aqueous saturated sodium bicarbonate solution, sodium sulfate was added, this was filtered, and concentrated, and the resulting residue was purified by subjecting to silica gel chromatography. The column chromatography was eluted with ethyl acetate-methanol, and the objective fraction was concentrated to obtain a mixture of aldehyde hydrate and methylacetyl as a colorless transparent oil product. The resulting oil product was dissolved in dichloromethane (5 mL), 1,3-diaminopropane dihydrochloride (354 mg, 2.41 mmol) and, subsequently, acetic acid (0.069 ml, 1.2 mmol) were added, and the mixture was stirred at room temperature for 6 hours. The reaction solution was diluted with dichloromethane, and the insolubles were filtered, and concentrated under reduced pressure to obtain a crude purified product of Compound 169B.

MS: m/z=326.20 [M+H]$^+$.

Third Step

Potassium carbonate (498 mg, 3.61 mmol) and, subsequently, bromomethylenedibenzene (890 mg, 3.61 mmol) were added to a solution of Compound 169B (391 mg, 1.20 mmol) in acetonitrile (4 mL). After the reaction solution was stirred at 90° C. for 2 hours, water, ethyl acetate and brine were added to the reaction solution, the ethyl acetate layer was separated, and the aqueous layer was extracted with ethyl acetate once. The combined extracts were dried with magnesium sulfate, filtered, and concentrated. The resulting residue was purified by subjecting to silica gel column chromatography. The column was eluted with ethyl acetate-methanol, and the objective fraction was concentrated to obtain 106 mg of Compound 169C as an orange solid.

MS: m/z=492.15 [M+H]$^+$.

Fourth Step

Lithium chloride (27.2 mg, 0.641 mmol) was added to a solution of Compound 169C (105 mg, 0.214 mmol) in DMI (2 mL), and the mixture was stirred at 90° C. for 3 hours. Lithium chloride (27.2 mg, 0.641 mmol) was further added, and the mixture was stirred at 90° C. for 1 hour. The reaction solution was concentrated under reduced pressure, and the resulting residue was purified using a LCMS collection apparatus. The eluted solvent was distilled off, diethyl ether was added to the residue, and the precipitated solid was filtered off. Washing and drying with diethyl ether afforded 27 mg of Compound 169.

$^1$H-NMR (CD$_3$OD) δ: 1.63 (1H, dd, J=13.4, 2.8 Hz), 1.84 (1H, br s), 2.55-2.64 (1H, m), 2.90-3.10 (2H, m), 4.30 (1H, dd, J=14.5, 4.0 Hz), 4.52 (4H, dd, J=14.5, 3.8 Hz), 4.63-4.75 (4H, m), 5.16 (1H, s), 6.16 (1H, d, J=7.2 Hz), 6.78 (1H, d, J=7.2 Hz), 7.16-7.32 (10H, m).

MS: m/z=402.10 [M+H]$^+$.

Example 26

[Chemical formula 89]

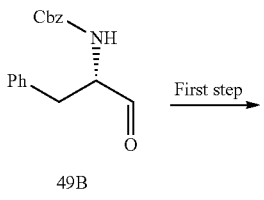

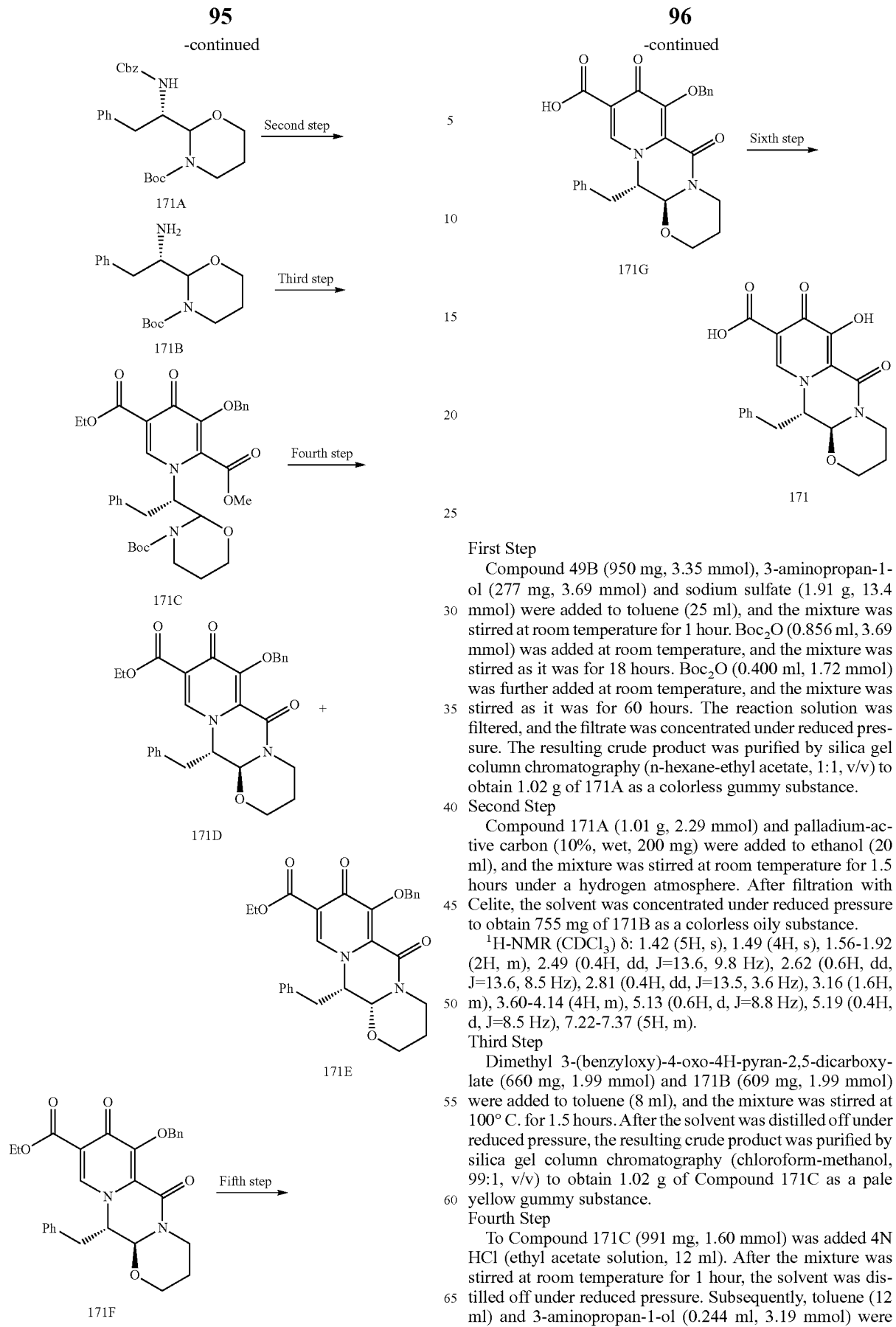

First Step

Compound 49B (950 mg, 3.35 mmol), 3-aminopropan-1-ol (277 mg, 3.69 mmol) and sodium sulfate (1.91 g, 13.4 mmol) were added to toluene (25 ml), and the mixture was stirred at room temperature for 1 hour. Boc$_2$O (0.856 ml, 3.69 mmol) was added at room temperature, and the mixture was stirred as it was for 18 hours. Boc$_2$O (0.400 ml, 1.72 mmol) was further added at room temperature, and the mixture was stirred as it was for 60 hours. The reaction solution was filtered, and the filtrate was concentrated under reduced pressure. The resulting crude product was purified by silica gel column chromatography (n-hexane-ethyl acetate, 1:1, v/v) to obtain 1.02 g of 171A as a colorless gummy substance.

Second Step

Compound 171A (1.01 g, 2.29 mmol) and palladium-active carbon (10%, wet, 200 mg) were added to ethanol (20 ml), and the mixture was stirred at room temperature for 1.5 hours under a hydrogen atmosphere. After filtration with Celite, the solvent was concentrated under reduced pressure to obtain 755 mg of 171B as a colorless oily substance.

$^1$H-NMR (CDCl$_3$) δ: 1.42 (5H, s), 1.49 (4H, s), 1.56-1.92 (2H, m), 2.49 (0.4H, dd, J=13.6, 9.8 Hz), 2.62 (0.6H, dd, J=13.6, 8.5 Hz), 2.81 (0.4H, dd, J=13.5, 3.6 Hz), 3.16 (1.6H, m), 3.60-4.14 (4H, m), 5.13 (0.6H, d, J=8.8 Hz), 5.19 (0.4H, d, J=8.5 Hz), 7.22-7.37 (5H, m).

Third Step

Dimethyl 3-(benzyloxy)-4-oxo-4H-pyran-2,5-dicarboxylate (660 mg, 1.99 mmol) and 171B (609 mg, 1.99 mmol) were added to toluene (8 ml), and the mixture was stirred at 100° C. for 1.5 hours. After the solvent was distilled off under reduced pressure, the resulting crude product was purified by silica gel column chromatography (chloroform-methanol, 99:1, v/v) to obtain 1.02 g of Compound 171C as a pale yellow gummy substance.

Fourth Step

To Compound 171C (991 mg, 1.60 mmol) was added 4N HCl (ethyl acetate solution, 12 ml). After the mixture was stirred at room temperature for 1 hour, the solvent was distilled off under reduced pressure. Subsequently, toluene (12 ml) and 3-aminopropan-1-ol (0.244 ml, 3.19 mmol) were added, and the mixture was stirred at 80° C. for 10 minutes.

After the solvent was distilled off under reduced pressure, the resulting crude product was purified by silica gel column chromatography (chloroform-methanol, 99:1→95:5→90:10, v/v) to obtain 341 mg of Compound 171D as a yellow gummy substance and 338 mg of Compound 171E as a colorless solid.

171D: $^1$H-NMR (CDCl$_3$) δ: 1.29 (3H, t, J=7.1 Hz), 1.51 (1H, d, J=13.7 Hz), 1.97 (1H, m), 2.91 (1H, dd, J=13.8, 9.8 Hz), 2.99-3.10 (2H, m), 3.90 (1H, td, J=12.1, 2.5 Hz), 4.12 (2H, m), 4.25 (2H, m), 4.83 (2H, m), 5.33 (1H, d, J=10.1 Hz), 5.51 (1H, d, J=10.1 Hz), 6.88 (2H, m), 7.23-7.40 (7H, m), 7.68 (2H, m)

171E: $^1$H-NMR (CDCl$_3$) δ: 1.19 (3H, t, J=7.2 Hz), 1.82-1.99 (2H, m), 2.73 (1H, dd, J=14.0, 11.3 Hz), 3.13 (1H, m), 3.35 (1H, dd, J=14.0, 3.4 Hz), 3.63 (1H, m), 3.90-4.26 (4H, m), 4.43 (1H, d, J=13.6 Hz), 5.27 (1H, t, J=3.5 Hz), 5.31 (2H, s), 6.78 (2H, dd, J=6.3, 3.2 Hz), 7.01 (1H, d, J=7.0 Hz), 7.18 (3H, t, J=3.1 Hz), 7.28-7.39 (3H, m), 7.67 (2H, m).

Fifth Step

Compound 171D (329 mg, 0.673 mmol) was dissolved in ethanol (2 ml) and THF (4 ml), a 2N aqueous sodium hydroxide solution (1.69 ml, 3.38 mmol) was added, the mixture was stirred at room temperature for 1 hour. To the reaction solution was added 2N hydrochloric acid, and this was extracted with ethyl acetate, and dried with sodium sulfate. The solvent was concentrated under reduced pressure to obtain 215 mg of Compound 171F as a colorless solid.

MS: m/z=461 [M+H]$^+$.

Sixth Step

Trifluoroacetic acid (2 ml) was added to Compound 171F (50 mg, 0.11 mmol), and the mixture was stirred at room temperature for 1 hour. After concentration under reduced pressure, a pH was adjusted to 6 with an aqueous sodium bicarbonate solution and 2N hydrochloric acid, and this was extracted with chloroform, and dried with sodium sulfate. After the solvent was distilled off under reduced pressure, chloroform-methanol-ethyl ether were added, and the precipitated solid was filtered off to obtain 24 mg of Compound 171 as a colorless solid.

$^1$H-NMR (DMSO-d6) δ: 1.63 (1H, d, J=12.6 Hz), 1.83 (1H, m), 2.96-3.29 (3H, m), 4.05 (2H, m), 4.55 (1H, dd, J=13.2, 4.4 Hz), 5.08 (1H, dd, J=9.2, 5.4 Hz), 5.30 (1H, s), 7.19 (5H, m), 8.09 (1H, s), 12.84 (1H, brs).

MS: m/z=371 [M+H]$^+$.

Example 27

[Chemical formula 90]

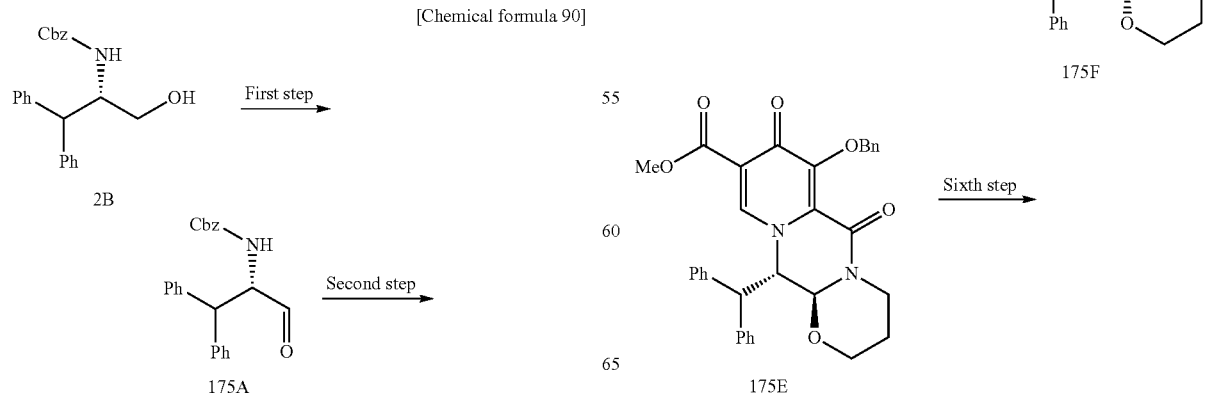

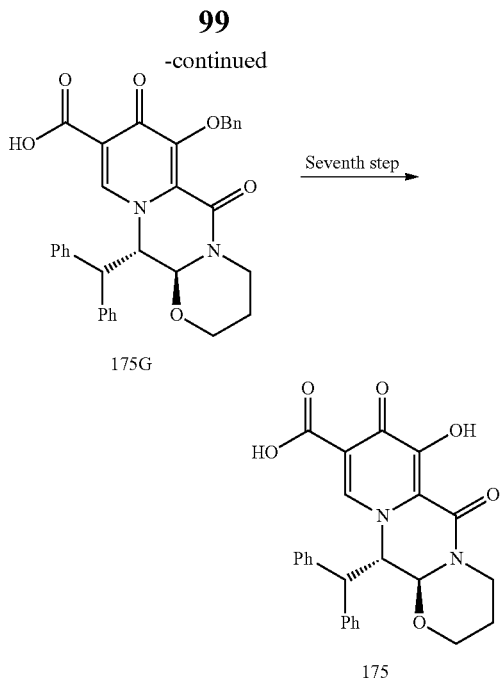

175G

175

First Step

A solution of Compound 2b (1.98 g, 5.48 mmol) in methylene chloride (10 ml) was added dropwise to Dess-Martin Periodinane (0.3M, methylene chloride solution, 25.0 ml, 7.50 mmol) at 0° C. After stirring at room temperature for 3 hours, the mixture was poured into a 1N aqueous sodium hydroxide solution, and this was extracted with ethyl ether. The organic layer was washed with 1N aqueous sodium hydroxide solution and saturated sodium chloride water, and dried with magnesium sulfate. After the solvent was distilled off under reduced pressure, this was purified by silica gel column chromatography (n-hexane-ethyl acetate, 2:1, v/v) to obtain 1.73 g of Compound 175A.

$^1$H-NMR (CDCl$_3$) δ: 4.55 (1H, d, J=7.3 Hz), 5.09 (2H, s), 5.14 (2H, m), 7.22-7.35 (15H, m), 9.62 (1H, s).

Second Step

Compound 175A (1.30 g, 4.59 mmol), 3-aminopropan-1-ol (379 mg, 5.05 mmol) and sodium sulfate (3.26 g, 22.4 mmol) were added to toluene (40 ml), and the mixture was stirred at room temperature for 1 hour. Boc$_2$O (1.17 ml, 5.05 mmol) was added at room temperature, and the mixture was stirred as it was for 18 hours. Boc$_2$O (1.17 ml, 5.05 mmol) and sodium sulfate (3.26 g, 22.4 mmol) were added, and the mixture was stirred for 60 hours. The reaction solution was filtered, and the filtrate was concentrated under reduced pressure. The resulting crude product was purified by silica gel column chromatography (n-hexane-ethyl acetate, 1:1, v/v) to obtain 635 mg of 175B as a colorless solid.

Third Step

Compound 175B (632 mg, 1.22 mmol) and palladium-active carbon (10%, wet, 100 mg) were added to ethanol (10 ml) and THF (5 ml), and the mixture was stirred at room temperature for 3 hours. After filtration with Celite, the solvent was concentrated under reduced pressure to obtain 502 mg of 175C as a colorless oily substance.

$^1$H-NMR (CDCl$_3$) δ: 1.45 (9H, s), 1.77 (2H, m), 3.18-3.27 (1H, m), 3.43-3.51 (1H, m), 4.04 (4H, m), 4.92 (1H, d, J=4.7 Hz), 7.28 (10H, m).

Fourth Step

Dimethyl 3-(benzyloxy)-4-oxo-4H-pyran-2,5-dicarboxylate (390 mg, 1.22 mmol) and 175C (468 mg, 1.22 mmol) were added to toluene (5 ml), and the mixture was stirred at 100° C. for 2 hours. After the solvent was distilled off under reduced pressure, the resulting crude product was purified by silica gel column chromatography (n-hexane-ethyl acetate, 1:1, v/v) to obtain 391 mg of Compound 175D as a pale yellow gummy substance.

Fifth Step

To Compound 175D (388 mg, 0.568 mmol) was added 4N HCl (ethyl acetate solution, 4 ml). After stirring at room temperature for 1 hour, the solvent was distilled off under reduced pressure. Subsequently, toluene (4 ml) and 3-aminopropan-1-ol (0.0870 ml, 1.14 mmol) were added, and the mixture was stirred at 80° C. for 5 hours. After the solvent was distilled off under reduced pressure, the resulting crude product was purified by silica gel column chromatography (chloroform-methanol, 98:2, v/v) to obtain 57 mg of Compound 175E as a yellow gummy substance and 44 mg of Compound 175F as a brown gummy substance.

175E: $^1$H-NMR (CDCl$_3$) δ: 1.91-2.00 (2H, m), 2.87 (1H, m), 3.78 (3H, s), 3.87-4.15 (3H, m), 4.61 (1H, d, J=12.1 Hz), 4.78 (2H, m), 5.33 (1H, d, J=10.2 Hz), 5.63 (1H, d, J=10.2 Hz), 6.95 (2H, m), 7.13-7.53 (12H, m), 7.76 (2H, m)

175F: $^1$H-NMR (CDCl$_3$) δ: 1.83-1.97 (2H, m), 3.12-3.22 (1H, m), 3.50 (1H, m), 3.85 (3H, s), 3.90 (1H, m), 4.34-4.40 (1H, m), 4.74 (1H, d, J=8.6 Hz), 4.84-4.89 (1H, m), 5.09 (1H, d, J=3.3 Hz), 5.15 (1H, d, J=9.9 Hz), 5.26 (1H, d, J=9.6 Hz), 7.08-7.50 (13H, m), 7.65-7.77 (3H, m).

Sixth Step

Compound 175E (57 mg, 0.10 mmol) was dissolved in THF (0.5 ml) and ethanol (0.5 ml), a 2N aqueous sodium hydroxide solution (0.25 ml, 0.50 mmol) was added at room temperature, and the mixture was stirred as it was for 1 hour. To the mixture was added 1N hydrochloric acid, and this was extracted with chloroform, and dried with sodium sulfate. The solvent was distilled off under reduced pressure, and the resulting crude product was purified by silica gel column chromatography (chloroform-methanol, 98:2, v/v) to obtain Compound 175G.

Seventh Step

Trifluoroacetic acid (1 ml) was added to Compound 175G obtained in Sixth step, and the mixture was stirred at room temperature for 1 hour. After concentration under reduced pressure, a pH was adjusted to 3 with an aqueous sodium bicarbonate solution and 2N hydrochloric acid, and this was extracted with chloroform, and dried with sodium sulfate. After the solvent was distilled off under reduced pressure, chloroform-methanol-ethyl ether were added, and the precipitated solid was filtered off to obtain 11 mg of Compound 175 as a colorless solid.

$^1$H-NMR (DMSO-d6) δ: 1.50 (1H, d, J=13.1 Hz), 1.79 (1H, m), 3.17 (1H, m), 3.86 (1H, t, J=11.0 Hz), 4.03 (1H, dd, J=10.8, 4.1 Hz), 4.46 (1H, d, J=12.0 Hz), 4.53 (1H, dd, J=12.7, 4.2 Hz), 4.84 (1H, s), 5.85 (1H, d, J=11.7 Hz), 7.22 (7H, m), 7.44 (2H, t, J=7.6 Hz), 7.65 (2H, d, J=7.3 Hz), 8.14 (1H, s), 12.75 (1H, s), 15.33 (1H, brs).

MS: m/z=447 [M+H]$^+$.

Example 28

Measurement of Powder X-Ray Diffraction Pattern

The powder X-ray diffraction measurement of the crystal obtained in each Example was performed under the following measurement condition according to a method of powder X-ray diffraction measurement described in a general test method of Japanese Pharmacopoeia.

(Apparatus)
D-8-Discover manufactured by Bruker
(Operation Method)
A sample was measured under the following conditions.
Measurement method: reflection method
Kind of light source: Cu tube
Wavelength used: CuKα-ray
Tube current: 40 mA
Tube voltage: 40 Kv
Sample plate: glass
X-ray incident angle: 3° and 12°

Test Example 1

Measurement of Cap-Dependant Endonuclease (CEN) Inhibitory Activity

1) Preparation of Substrate
30merRNA (5'-pp-[m2'-O]GAA UAU(-Cy3) GCA UCA CUA GUA AGC UUU GCU CUA-BHQ2-3': manufactured by Japan Bioservice) in which G at a 5' end is diphosphate-modified, a hydroxy group at 2' position is methoxylation-modified, U sixth from a 5' end is labelled with Cy3, and a 3' end is labelled with BHQ2 was purchased, and a cap structure was added using ScriptCap system manufactured by EPI-CENTRE (a product was m7G [5']-ppp-[5'] [m2'-O]GAA UAU(-Cy3) GCA UCA CUA GUA AGC UUU GCU CUA(-BHQ2)-3'). This was separated and purified by denatured polyacrylamide gel electrophoresis, and used as a substrate.

2) Preparation of Enzyme
RNP was prepared from a virus particle using standard method (Reference Document: VIROLOGY (1976) 73, p 327-338 OLGA M. ROCHOVANSKY). Specifically, A/WSN/33 virus ($1 \times 10^3$ PFU/mL, 200 µL) was innoculated in a 10 days old embryonated chicken egg. After incubation at 37° C. for 2 days, the allantoic fluid of the chicken egg was recovered. A virus particle was purified by ultracentrifugation using 20% sucrose, solubilized using TritonX-100 and lysolecithin, and an RNP fraction (50-70% glycerol fraction) was collected by ultracentrifugation using a 30-70% glycerol density gradient, and was used as an enzyme solution (containing approximately 1 nM PB1·PB2·PA complex).

3) Enzymatic Reaction
An enzymatic reaction solution (2.54) (composition: 53 mM Tris-hydrochloride (pH 7.8), 1 mM $MgCl_2$, 1.25 mM dithiothreitol, 80 mM NaCl, 12.5% glycerol, enzyme solution 0.154) was dispensed into a 384-well plate made of polypropylene. Then, 0.5 µL of a test substance solution which had been serially diluted with dimethyl sulfoxide (DMSO) was added to the plate. As a positive control (PC) or a negative control (NC), 0.5 µL of DMSO was added to the plate respectively. Each plate was mixed well. Then, 2 µL of a substrate solution (1.4 nM substrate RNA, 0.05% Tween20) was added to initiate a reaction. After room temperature incubation for 60 minutes, 1 µL of the reaction solution was collected and added to 10 µL of a Hi-Di formamide solution (containing GeneScan 120 Liz Size Standard as a sizing marker: manufactured by Applied Biosystem (ABI)) in order to stop the reaction. For NC, the reaction was stopped in advance by adding EDTA (4.5 mM) before initiation of the reaction (all concentrations described above are final concentrations).

3) Measurement of Inhibition Ratio ($IC_{50}$ Value)
The solution for which the reaction was stopped was heated at 85° C. for 5 minutes, rapidly cooled on ice for 2 minutes, and analyzed with an ABI PRIZM 3730 genetic analyzer. A peak of the cap-dependent endonuclease product was quantitated by analysis software ABI Genemapper, a CEN reaction inhibition ratio (%) of a test compound was obtained by setting fluorescent intensities of PC and NC to be 0% inhibition and 100% inhibition, respectively, an $IC_{50}$ value was obtained using curve fitting software (XLfit2.0: Model 205 (manufactured IDBS etc.)). The $IC_{50}$ values of test substances are shown in Table 1.

Test Example 2

CPE Inhibitory Effect Confirming Assay

<Material>
2% FCS E-MEM (prepared by adding kanamycin and FCS to MEM (Minimum Essential Medium) (Invitrogen))
0.5% BSA E-MEM (prepared by adding kanamycin and BSA to MEM (Minimum Essential Medium) (Invitrogen))
HBSS (Hanks' Balanced Salt Solution)
MDBK Cell
Cells were adjusted to the appropriate cell number ($3 \times 10^5$/mL) with 2% FCS E-MEM.
MDCK Cell
After washing with HBSS two times, cells were adjusted to the appropriate cell number ($5 \times 10^5$/mL) with 0.5% BSA E-MEM.
Trypsin Solution
Trypsin from porcine pancreas (SIGMA) was dissolved in PBS(−), and filtrated with a 0.45 µm filter.
EnVision (Perkin Elmer)
WST-8 Kit (Kishida Chemical Co., Ltd.)
10% SDS solution
<Operation Procedure>
Dilution and Dispensation of Test Sample
As a culture medium, 2% FCS E-MEM was used at the use of MDBK cells, and 0.5% BSA E-MEM was used at the use of MDCK cells. Hereinafter, for diluting virus, cells and a test sample, the same culture medium was used.
A test sample was diluted with a culture medium to a appropriate concentration in advance, and then 2 to 5-fold serial dilution on a 96 well plate (50 µL/well) was prepared. Two plate, one for measuring anti-Flu activity and the aother for measuring cytotoxity, were prepared. Each assay was performed triplicate for each drug.
At the use of MDCK cells, trypsin was added to the cells to be a final concentration of 3 µg/mL only for measuring anti-Flu activity.
Dilution and Dispensation of Influenza Virus
An influenza virus was diluted with a culture medium to a appropriate concentration in advance, and each 50 µL/well was dispensed on a 96-well plate containing a test substance.
Each 50 µL/well of a culture medium was dispensed on a plate containing a test substance for measuring cytotoxity.
Dilution and Dispensation of Cell
Each 100 µL/well of cells which had been adjusted to the appropriate cell number was dispensed on a 96 well plate containing a test substance. This was mixed with a plate mixer, and incubated in a $CO_2$ incubator for 3 days for measuring anti-Flu activity and measuring cytotoxity.
Dispensation of WST 8
The cells in 96-well plate which had been incubated for 3 days was observed visually under a microscope, and appearance of the cells, the presence or absence of a crystal of test substance were checked. The supernatant was removed so that the cells were not absorbed from the plate.
WST-8 Kit was diluted 10-fold with a culture medium, and each 100 µL was dispensed into each well. After mixing with a plate mixer, cells were incubated in a $CO_2$ incubator for 1 to 3 hours.

After incubation, regarding the plate for measuring anti-Flu activity, each 10 μL/well of a 10% SDS solution was dispensed in order to inactivate a virus.

Measurement of Absorbance

After the 96-well plate was mixed, absorbance was measured with EnVision at two wavelengths of 450 nm/620 nm.

<Calculation of Each Measurement Item Value>

The value was calculated using Microsoft Excel or a program having the equivalent calculation and processing ability, based on the following calculation equation.

Calculation of effective concentration to achieve 50% CPE inhibition (EC50)

$$EC50 = 10^Z$$

$$Z = (50\% - \text{High} \%)/(\text{High} \% - \text{Low} \%) \times \{\log(\text{High conc.}) - \log(\text{Low conc.})\} + \log(\text{High conc.})$$

$IC_{50}$ values of test substances are shown in Table 1.

TABLE 1

| Examle No. | Compound No | CEN IC$_{50}$ (μM) | CPE IC$_{50}$ (μM) |
|---|---|---|---|
| 14 | 43 | 0.078 | 1.41 |
| 21 | 128 | 0.063 | 0.416 |
| 27 | 175 | 0.132 | 0.102 |

The test substances exhibited the high cap-dependent endonuclease (CEN) inhibitory activity, and exhibited the high CPE inhibitory effect. These substances can be medicaments useful as a therapeutic agent and/or prophylactic agent of a symptom and/or a disease induced by infection with influenza virus.

Therefore, it can be said that the substance and production method of the present invention are an intermediate substance and a production method useful for efficiently producing substances which can be used as a medicament.

The invention claimed is:

1. A method of producing a compound shown by formula (X4) or a salt thereof, comprising the steps of:

(Step B)

reacting a compound shown by formula (X2):

[Chemical formula 1]

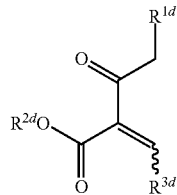

(X2)

(wherein $R^{1d}$ is halogen, lower alkyloxy, or carbocyclyl lower alkyloxy, $R^{2d}$ is hydrogen or lower alkyl, $R^{3d}$ is hydrogen, lower alkyl optionally substituted by substituent E, $N(R^{3e})_2$, or —$OR^{3e}$, $R^{3e}$s are each independently lower alkyl optionally substituted by substituent E, or may be taken together to form a heterocycle, and wavy line is E form and/or Z form or the mixture thereof, Substituent E: halogen, cyano, hydroxy, carboxy, formyl, amino, oxo, nitro, lower alkyl, halogeno lower alkyl, lower alkyloxy, carbocyclyl optionally substituted by substituent F, heterocyclyl optionally substituted by substituent F, carbocyclyl lower alkyloxy optionally substituted by substituent F, heterocyclyl lower alkyloxy optionally substituted by substituent F, carbocyclyl lower alkylthio optionally substituted by substituent F, heterocyclyl lower alkylthio optionally substituted by substituent F, carbocyclyl lower alkylamino optionally substituted by substituent F, heterocyclyl lower alkylamino optionally substituted by substituent F, carbocyclyloxy optionally substituted by substituent F, heterocyclyloxy optionally substituted by substituent F, carbocyclylcarbonyl optionally substituted by substituent F, heterocyclylcarbonyl optionally substituted by substituent F, carbocyclylaminocarbonyl optionally substituted by substituent F, heterocyclylaminocarbonyl optionally substituted by substituent F, halogeno lower alkyloxy, lower alkyloxy lower alkyl, lower alkyloxy lower alkyloxy, lower alkylcarbonyl, lower alkyloxycarbonyl, lower alkyloxycarbonylamino, lower alkylamino, lower alkylcarbonylamino, lower alkylaminocarbonyl, lower alkylsulfonyl, and lower alkylsulfonylamino;

Substituent F: halogen, hydroxy, carboxy, amino, oxo, nitro, lower alkyl, halogeno lower alkyl, lower alkyloxy, and amino protective group)

with a compound shown by formula (V2):

[Chemical formula 2]

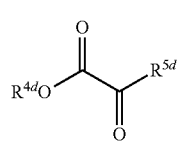

(V2)

(wherein $R^{4d}$ is lower alkyl, $R^{5d}$ is hydrogen, halogen, lower alkyloxy optionally substituted by substituent E, or —O—SO$_2$—$R^{5e}$, $R^{5e}$ is lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl optionally substituted by substituent E, and substituent E is defined above)

to obtain a compound shown by formula (X3):

[Chemical formula 3]

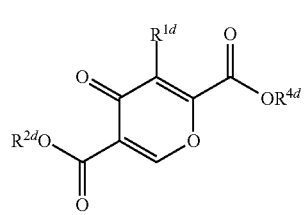

(X3)

(wherein each symbol is defined above); and (Step C)
reacting the compound shown by formula (X3) with a compound shown by formula (V3):

[Chemical formula 4]

(V3)

(wherein $R^{6d}$ is lower alkyl optionally substituted by substituent E, lower alkenyl optionally substituted by substituent E, amino optionally substituted by substituent E, lower alkylamino optionally substituted by substituent E, carbocyclyl optionally substituted by substituent E, or heterocyclyl optionally substituted by substituent E, and substituent E is defined above)
to obtain a compound shown by formula (X4):

[Chemical formula 5]

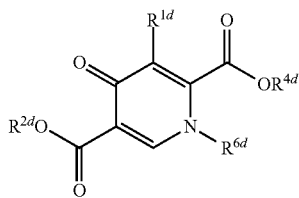
(X4)

(wherein each symbol is defined above).

2. A method according to claim 1, wherein Step B and Step C are continuously performed.

3. A method of producing a compound shown by formula (XA4), or a salt thereof:

[Chemical formula 9]

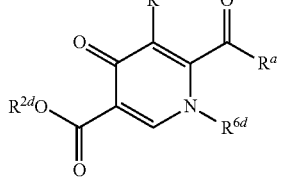
(XA4)

(wherein $R^a$ is hydrogen, hydroxy, lower alkylamino optionally substituted by substituent E, lower alkenylamino optionally substituted by substituent E, lower alkynylamino optionally substituted by substituent E, carbocyclyl lower alkylamino optionally substituted by substituent E, or heterocyclyl lower alkyl amino optionally substituted by substituent E, and
each symbol is defined above)
comprising the step of,
reacting a compound shown by formula (X2):

[Chemical formula 6]

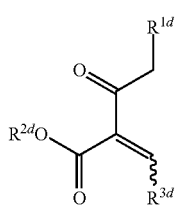
(X2)

(wherein each symbol is defined above)

with a compound shown by formula (VA2):

[Chemical formula 7]

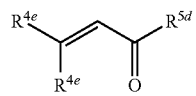
(VA2)

(wherein $R^{4e}$s are each independently hydrogen, lower alkyl optionally substituted by substituent E, carbocyclyl optionally substituted by substituent E, or heterocyclyl optionally substituted by substituent E, and
$R^{5d}$ and substituent E are defined above); and
reacting with a compound shown by formula (V3):

(V3)

(wherein $R^6$ is defined above).

4. A method of producing a compound shown by formula (X4) or formula (XA4), or a salt thereof:

[Chemical formula 15]

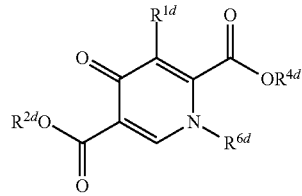
(X4)

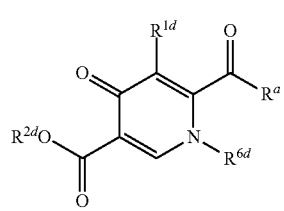
(XA4)

(wherein each symbol is defined in claim 1 or claim 3)
comprising the step of,
reacting a compound shown by formula (X3) or formula (XA3):

[Chemical formula 13]

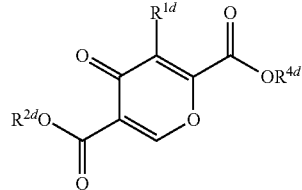
(X3)

-continued

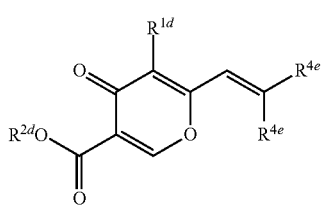
(XA3)

(wherein each symbol is defined in claim 1)
or the derivative of formula (XA3) with a compound shown by formula (V3):

[Chemical formula 14]

 (V3)

(wherein each symbol is defined in claim 1).

5. A method of producing a compound shown by formula (X4') or formula
(XA4'), or a salt thereof:

[Chemical formula 19]

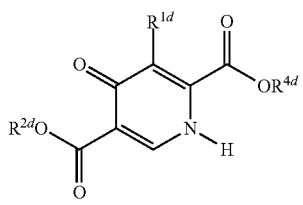
(X4')

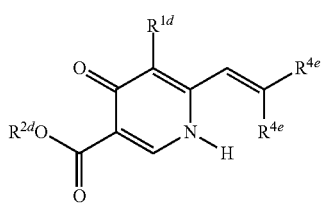
(XA4')

(wherein each symbol is defined in claim 1)
comprising reacting a compound shown by formula (X2):

[Chemical formula 16]

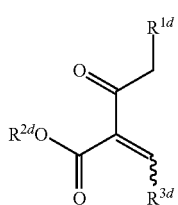
(X2)

(wherein each symbol is defined in claim 1) with a compound shown by formula (V2) or formula (VA2):

[Chemical formula 17]

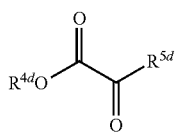
(V2)

-continued

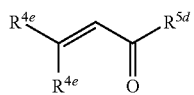
(VA2)

(wherein each symbol is defined in claim 1)
and a compound shown by formula (V2'):

[Chemical formula 1]

 (V2')

(wherein Xd– is counter anion of ammonium cation).

6. A method of producing a compound shown by formula (X4) or formula
(XA4), or a salt thereof:

[Chemical formula 22]

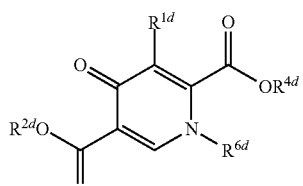
(X4)

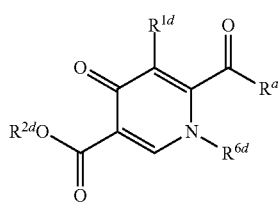
(XA4)

(wherein each symbol is defined in claim 1 or claim 3)
comprising the step of:
reacting the compound shown by formula (X4') or formula (XA4'):

[Chemical formula 20]

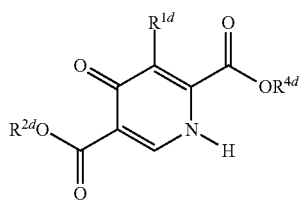
(X4')

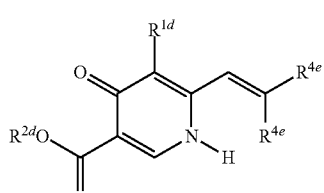
(XA4')

(wherein each symbol is defined in claim 1)
obtained in the production method as defined in claim 5, or the derivative of formula ((A4') with a compound shown by formula (V3'):

[Chemical formula 21]

$$R^{6d}\text{-}L^d \quad (V3')$$

(wherein $R^{6d}$ is defined in claim 1, $L^d$ is a leaving group, and Ph is a phenyl group).

7. A method according to claim 1, 2, 3 or 5, wherein the compound shown by formula (X2) is obtained by reacting a compound shown by formula (X1):

[Chemical formula 23]

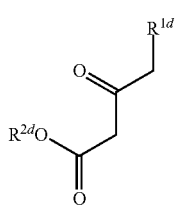

(X1)

(wherein each symbol is defined in claim 1) with a compound shown by formula (VI):

[Chemical formula 24]

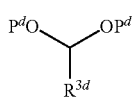

(VI)

(wherein $P^d$ is lower alkyl optionally substituted by substituent E, and $R^{3d}$ and substituent E are defined in claim 1).

8. A method according to claim 1, 2, 3 or 5, wherein the compound shown by formula (X2) is obtained by reacting a compound shown by formula (Z1):

[Chemical formula 25]

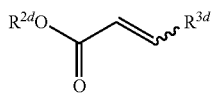

(Z1)

(wherein each symbol is defined in claim 1) with a compound shown by formula (Z2):

[Chemical formula 26]

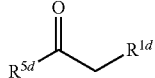

(Z2)

(wherein each symbol is defined in claim 1).

9. A compound shown by formula (X4), or a pharmaceutically acceptable salt thereof:

[Chemical formula 28]

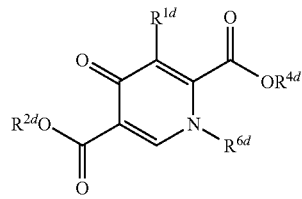

(X4)

wherein $R^{1d}$ is halogen, lower alkyloxy, or carbocyclyl lower alkyloxy, $R^{2d}$ is hydrogen or lower alkyl, $R^{4d}$ is lower alkyl, and $R^{6d}$ is lower alkyl optionally substituted by substituent E, lower alkenyl optionally substituted by substituent E, amino optionally substituted by substituent E, lower alkylamino optionally substituted by substituent E, carbocyclyl optionally substituted by substituent E, or heterocyclyl optionally substituted by substituent E;

further wherein the substituent E is chosen from halogen, cyano, hydroxy, carboxy, formyl, amino, oxo, nitro, lower alkyl, halogeno lower alkyl, lower alkyloxy, carbocyclyl optionally substituted by substituent F, heterocyclyl optionally substituted by substituent F, carbocyclyl lower alkyloxy optionally substituted by substituent F, heterocyclyl lower alkyloxy optionally substituted by substituent F, carbocyclyl lower alkylthio optionally substituted by substituent F, heterocyclyl lower alkylthio optionally substituted by substituent F, carbocyclyl lower alkylamino optionally substituted by substituent F, heterocyclyl lower alkylamino optionally substituted by substituent F, carbocyclyloxy optionally substituted by substituent F, heterocyclyloxy optionally substituted by substituent F, carbocyclylcarbonyl optionally substituted by substituent F, heterocyclylcarbonyl optionally substituted by substituent F, carbocyclylaminocarbonyl optionally substituted by substituent F, heterocyclylaminocarbonyl optionally substituted by substituent F, halogeno lower alkyloxy, lower alkyloxy lower alkyl, lower alkyloxy lower alkyloxy, lower alkylcarbonyl, lower alkyloxycarbonyl, lower alkyloxycarbonylamino, lower alkylamino, lower alkylcarbonylamino, lower alkylaminocarbonyl, lower alkylsulfonyl, and lower alkylsulfonylamino; and the substituent F is chosen from halogen, hydroxy, carboxy, amino, oxo, nitro, lower alkyl, halogeno lower alkyl, lower alkyloxy, and amino protective group.

10. A compound shown by formula (X4'), or a pharmaceutically acceptable salt thereof:

[Chemical formula 29]

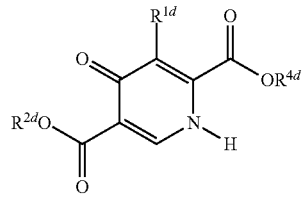

(X4')

wherein $R^{1d}$ is halogen, lower alkyloxy, or carbocyclyl lower alkyloxy, $R^{2d}$ is hydrogen or lower alkyl, and $R^{4d}$ is lower alkyl, further wherein the substituent E is chosen from halogen, cyano, hydroxy, carboxy, formyl, amino, oxo, nitro, lower alkyl, halogeno lower alkyl, lower alkyloxy, carbocyclyl optionally substituted by substituent F, heterocyclyl optionally substituted by substituent F, carbocyclyl lower alkyloxy optionally substituted by substituent F, heterocyclyl lower alkyloxy optionally substituted by substituent F, carbocyclyl lower alkylthio optionally substituted by substituent F, heterocyclyl lower alkylthio optionally substituted by substituent F, carbocyclyl lower alkylamino optionally substituted by substituent F, heterocyclyl lower alkylamino optionally substituted by substituent F, carbocyclyloxy optionally substituted by substituent F, heterocyclyloxy optionally substituted by substituent F, carbocyclylcarbonyl optionally substituted by substituent F, heterocyclylcarbonyl optionally substituted by substituent F, carbocyclylaminocarbonyl optionally substituted by substituent F, heterocyclylaminocarbonyl optionally substituted by substituent F, halogeno lower alkyloxy, lower alkyloxy lower alkyl, lower alkyloxy lower alkyloxy, lower alkylcarbonyl, lower alkyloxycarbonyl, lower alkyloxycarbonylamino, lower alkylamino, lower alkylcarbonylamino, lower alkylaminocarbonyl, lower alkylsulfonyl, and lower alkylsulfonylamino; and the substituent F is chosen from halogen, hydroxy, carboxy, amino, oxo, nitro, lower alkyl, halogeno lower alkyl, lower alkyloxy, and amino protective group.

* * * * *

UNITED STATES PATENT AND TRADEMARK OFFICE
CERTIFICATE OF CORRECTION

PATENT NO. : 8,865,907 B2  
APPLICATION NO. : 13/260063  
DATED : October 21, 2014  
INVENTOR(S) : Yukihito Sumino et al.

Page 1 of 1

It is certified that error appears in the above-identified patent and that said Letters Patent is hereby corrected as shown below:

In the Claims

Claim 1, col. 103, lines 56-57, "(wherein $R^{1d}$ is halogen, lower alkyloxy, or carbocyclyl lower alkyloxy" should read --(wherein $R^{1d}$ is halogen, lower alkyloxy,--.

Claim 3, col. 106, line 22, "(wherein $R^6$ is defined above)." should read --(wherein $R^{6d}$ is defined above).--.

Signed and Sealed this  
Tenth Day of March, 2015

Michelle K. Lee  
*Deputy Director of the United States Patent and Trademark Office*